US011793844B2

(12) United States Patent
Cheng et al.

(10) Patent No.: US 11,793,844 B2
(45) Date of Patent: Oct. 24, 2023

(54) VIRUS FOR TREATMENT OF TUMOR

(71) Applicants: XIAMEN UNIVERSITY, Xiamen (CN); YANG SHENG TANG COMPANY, LTD., Hangzhou (CN)

(72) Inventors: Tong Cheng, Xiamen (CN); Wei Wang, Xiamen (CN); Junkai Wan, Xiamen (CN); Wenkun Fu, Xiamen (CN); Xiangzhong Ye, Beijing (CN); Jun Zhang, Xiamen (CN); Ningshao Xia, Xiamen (CN)

(73) Assignees: XIAMEN UNIVERSITY, Xiamen (CN); YANG SHENG TANG COMPANY, LTD., Hangzhou (CN)

( * ) Notice: Subject to any disclaimer, the term of this patent is extended or adjusted under 35 U.S.C. 154(b) by 740 days.

(21) Appl. No.: 16/632,741

(22) PCT Filed: Jul. 18, 2018

(86) PCT No.: PCT/CN2018/096100

§ 371 (c)(1),
(2) Date: Jan. 21, 2020

(87) PCT Pub. No.: WO2019/015601

PCT Pub. Date: Jan. 24, 2019

(65) Prior Publication Data

US 2020/0254036 A1 Aug. 13, 2020

(30) Foreign Application Priority Data

Jul. 21, 2017 (CN) ......................... 201710600732.8

(51) Int. Cl.

| | |
|---|---|
| ***A61K 35/768*** | (2015.01) |
| ***A61P 35/00*** | (2006.01) |
| ***C12N 7/00*** | (2006.01) |
| ***C12N 15/86*** | (2006.01) |
| *A61K 48/00* | (2006.01) |
| *C07K 14/535* | (2006.01) |
| *C07K 16/28* | (2006.01) |
| *C12N 15/113* | (2010.01) |

(52) U.S. Cl.

CPC ............ *A61K 35/768* (2013.01); *A61P 35/00* (2018.01); *C12N 7/00* (2013.01); *C12N 15/86* (2013.01); *A61K 48/00* (2013.01); *C07K 14/535* (2013.01); *C07K 16/2818* (2013.01); *C07K 2317/622* (2013.01); *C12N 15/113* (2013.01); *C12N 2310/141* (2013.01); *C12N 2770/32321* (2013.01); *C12N 2770/32332* (2013.01); *C12N 2770/32343* (2013.01); *C12N 2770/32371* (2013.01)

(58) Field of Classification Search

CPC ....... A61K 35/768; A61K 48/00; A61P 35/00; C07K 14/535; C07K 16/2818; C07K 14/53; C07K 2317/622; C12N 7/00; C12N 15/86; C12N 15/113; C12N 2310/141; C12N 2770/32321; C12N 2770/32332; C12N 2770/32343

USPC ............. 424/204.1, 199.1, 216.1; 435/320.1; 536/24.1, 23.72

See application file for complete search history.

(56) References Cited

U.S. PATENT DOCUMENTS

| | | | | |
|---|---|---|---|---|
| 2010/0111873 | A1 | 5/2010 | Russell et al. | |
| 2016/0312314 | A1* | 10/2016 | Storch | C12Q 1/6806 |
| 2016/0355897 | A1 | 12/2016 | Nix et al. | |
| 2016/0376562 | A1 | 12/2016 | Venskus et al. | |
| 2017/0290893 | A1 | 10/2017 | Moss | |
| 2020/0016243 | A1 | 1/2020 | Moss | |
| 2020/0347466 | A1 | 11/2020 | Storch et al. | |
| 2021/0052708 | A1 | 2/2021 | Moss | |

FOREIGN PATENT DOCUMENTS

| | | | |
|---|---|---|---|
| CN | 105518128 | A | 4/2016 |
| JP | 2016-500108 | A | 1/2016 |
| JP | 2016-522805 | A | 8/2016 |
| JP | 2016-540505 | A | 12/2016 |
| WO | WO 2014/081937 | A2 | 5/2014 |
| WO | WO 2014/170389 | A1 | 10/2014 |
| WO | WO 2015/007788 | A1 | 1/2015 |
| WO | WO 2015077624 | A1 | 5/2015 |

(Continued)

OTHER PUBLICATIONS

Lau SK, Yip CC, Zhao PS, Chow WN, To KK, Wu AK, Yuen KY, Woo PC. Enterovirus D68 infections associated with severe respiratory illness in elderly patients and emergence of a novel clade in Hong Kong. Scientific reports. Apr. 28, 2016;6(1):1-9. (Year: 2016).*

Lu et al., "Poliovirus chimeras replicating under the translational control of genetic elements of hepatitis C virus reveal unusual properties of the internal ribosomal entry site of hepatitis C virus". Proc. Natl. Acad. Sci. Feb. 1996; vol. 93: 1412-1417. (Year: 1996).*

Waghmare et al., "Clinical disease due to enterovirus D68 in adult hematologic malignancy patients and hematopoietic cell transplant recipients". Blood. Jan. 15, 2015;125(11):1724-1729 (Year: 2015).*

(Continued)

*Primary Examiner* — Anne Marie S Wehbe
*Assistant Examiner* — Hanan Isam Abuzeineh
(74) *Attorney, Agent, or Firm* — Oblon, McClelland, Maier & Neustadt, L.L.P.

(57) ABSTRACT

Provided are an enterovirus D68 (EV-D68) or a modified form thereof, or a nucleic acid molecule comprising a genomic sequence or cDNA sequence of the EV-D68 or a modified form thereof, or a complementary sequence of the genomic sequence or cDNA sequence, or a pharmaceutical composition comprising the EV-D68 or a modified form thereof, or the nucleic acid molecule, and use of the EV-D68 or a modified form thereof, or the nucleic acid molecule in the manufacture of a pharmaceutical composition for treating a tumor.

6 Claims, 6 Drawing Sheets

Specification includes a Sequence Listing.

(56) References Cited

FOREIGN PATENT DOCUMENTS

WO WO 2016/044656 A1 3/2016

OTHER PUBLICATIONS

Ylä-Pelto et al., "TherapeuticUse of Native and Recombinant Enteroviruses". MDPI. Feb. 23, 2016; 8(57): 1-15. (Year: 2016).*

Brown et al., "Oncolytic Polio Virotherapy of Cancer". American Cancer Society Journals. Nov. 1, 2014; 120(21): 3277-3286. (Year: 2014).*

Gromeier et al., "Intergeneric poliovirus recombinants for the treatment of malignant glioma". PNAS. Jun. 6, 2000. 97(12): 6803-6808. (Year: 2000).*

Lau SK et al., "Enterovirus D68 Infections Associated with Severe Respiratory Illness in Elderly Patients and Emergence of a Novel Clade in Hong Kong". Sci Rep. Apr. 28, 2016; 6(1): 1-9 (Year: 2016).*

Ferguson et al., "Systemic Delivery of Oncolytic Viruses: Hopes and Hurdles". , Advances in Virology. Jan. 31, 2012. 2012; 1-14 (Year: 2012).*

Japanese Office Action dated Sep. 28, 2021 in Patent Application No. 2020-503013, (submitting English translation only), citing documents AA, AN-AS, AW and AX therein, 7 pages.

Jani Ylä-Pelto, et al., "Therapeutic Use of Native and Recombinant Enteroviruses" Viruses, No. 8, vol. 57, 2016, pp. 1-15.

Linda J. Berry, et al., "Potent Oncolytic Activity of Human Enteroviruses Against Human Prostate Cancer" The Prostate, vol. 68, 2008, pp. 557-587.

Extended European Search Report dated Mar. 29, 2021 in European Patent Application No. 18835927.7, citing documents AA-AE, AM and AV-AY therein, 9 pages.

Tie Gang Zhang, et al., "The Genomic Characterization of Enterovirus D68 from 2011 to 2015 in Beijing, China" Biomed. Environ. Sci., vol. 29, No. 9, XP055785724, 2016, pp. 675-677.

P. M. Chumakov, et al., "Oncolytic Enteroviruses" Molecular Biology, vol. 46, No. 5, XP035122625, Oct. 9, 2012, pp. 639-650.

Emily Jane Bek, et al., "The Pathogenesis and Prevention of Encephalitis due to Human Enterovirus 71" Current Infectious Disease Reports, vol. 14, No. 4, XP035079523, May 26, 2012, pp. 397-407.

Yuan-Pin Huang, et al., "Molecular and Epidemiological Study of Enterovirus D68 in Taiwan" Journal of Microbiology, Immunology and Infection, vol. 50, No. 4, XP085167237, Sep. 18, 2015, pp. 411-417.

International Search Report and Written Opinion dated Oct. 26, 2018, in PCT/CN2018/096100, citing documents AA-AB, AO-AP and AX therein, 20 pages.

Genbank, "Enterovirus D68 strain US/MO/14-18947, partial genome", KM851225, Dec. 1, 2014, 4 pages.

* cited by examiner

SEQUENCE LISTING

```
<160> NUMBER OF SEQ ID NOS: 20

<210> SEQ ID NO 1
<211> LENGTH: 7383
<212> TYPE: DNA
<213> ORGANISM: Artificial Sequence
<220> FEATURE:
<223> OTHER INFORMATION: cDNA sequence of wild type EV-D68 (EV-D68-WT)

<400> SEQUENCE: 1

taatacgact cactataggt taaaacagcc ttggggttgt tcccactcca agggcccacg     60

tggcggctag tactctggta cttcggtacc tttgtacgcc tgttttatct cccttcccaa    120

tgtaacttag aagttcttaa atcaatgctc aataggtggg gcgcaaacca gcgctctcat    180

gagcaagcac tcctgtctcc ccggtgaggt tgtataaact gttcccacgg ttgaaaacaa    240

cctatccgtt atccgctata gtacttcgag aaacctagta ccacctttgg attgttgacg    300

cgttgcgctc agcacactaa cccgtgtgta gcttgggtcg atgagtctgg acatacctca    360

ctggcgacag tggtccaggc tgcgttggcg gcctactcat ggtgaaagcc atgagacgct    420

agacatgaac aaggtgtgaa gagtctattg agctactata gagtcctccg gcccctgaat    480

gcggctaatc ctaaccatgg agcaagtgct cacaggccag tgagttgctt gtcgtaatgc    540

gcaagtccgt ggcggaaccg actactttgg gtgtccgtgt ttcacttttt acttttatga    600

ctgcttatgg tgacaatttg atattgttac catttagctt gtcaaatcaa ttgcaaaaga    660

tcctaaatct tatttatcaa cttgcatctt gataacttta atttgaaaat tttaacaatg    720

ggagctcagg ttactagaca acaaactggc actcatgaaa atgccaacat tgccacaaat    780
```

-continued

```
ggatctcata tcacatacaa tcagataaac ttttacaagg atagctatgc ggcttcagcc    840
agcaagcagg atttttcaca ggacccatca aaattcactg aaccagtagt ggaaggttta    900
aaagcagggg cgccagtttt gaaatctcct agtgctgagg catgtggcta cagtgataga    960
gtattacagc tcaaattagg aaattcagct attgtcaccc aggaagcagc gaactactgc   1020
tgcgcttatg gtgaatggcc caattactta ccagaccatg aagcagtagc cattgataaa   1080
cctacacaac cagaaactgc tacagataga ttctacactt tgaaatcagt caaatgggaa   1140
actggaagca caggatggtg gtggaaacta cccgatgcac tgaataatat aggcatgttt   1200
ggacagaatg tgcagcatca ctacctatat agatctggtt tcttgattca tgtgcagtgt   1260
aatgccacaa aattccatca aggtgcctta ttagtggtag caattccaga acatcagagg   1320
ggagcgcaca acaccaacac tagcccaggg tttgatgata taatgaaagg tgaagaagga   1380
gggaccttca atcatccata tgtccttgat gatggaacat cattggcttg tgcgacgata   1440
tttccacatc agtggataaa tctgagaacc aacaattcag caacaattgt tcttccctgg   1500
atgaatgctg ctccaatgga tttcccactt agacataatc agtggacgct agcaataata   1560
ccagtggtgc cattaggtac gcgtacaaca tcaagtatgg tcccaataac agtttcaatc   1620
gctccaatgt gttgtgagtt taatggactt agacacgcca ttactcaagg tgtcccaaca   1680
taccttttac caggctcggg acaattccta acaactgatg atcatagctc tgcaccagct   1740
ctcccgtgtt tcaacccaac tccagaaatg catatcccag ggcaggtccg taacatgcta   1800
gaagtggtcc aagtggaatc aatgatggag attaataaca cagaaagtgc agttggcatg   1860
gagcgtctta aggttgatat atcagcattg acagatgtcg atcaattgtt attcaacatt   1920
ccactggaca tacagttgga tggccactt agaaacactt tggtaggaaa catatctaga   1980
tattacactc attggtctgg atccctagaa atgacgttta tgttttgtgg cagcttcatg   2040
gcaacgggaa aattaatcct gtgctatact cctccaggtg gatcatgccc gacaaccaga   2100
gagaccgcca tgttaggtac acatattgtt tgggattttg gattacaatc tagtgtaacc   2160
ctgataatac cttggattag tggatcccac tacaggatgt ttaataatga tgctaagtca   2220
actaatgcca acgttggcta tgtcacttgt tttatgcaga ccaatctgat agtccccagt   2280
gaatcctctg acacgtgttc cttgataggg ttcatagcag caaaagatga tttctccctc   2340
agattaatga gagacagccc tgacattgga caactagacc atttacatgc agcagaggca   2400
gcctaccaga tcgagagcat catcaaaaca gcgaccgaca ctgtgaaaag tgagattaat   2460
gctgaacttg gtgtggtccc tagcttaaat gcagttgaaa caggtgcaac ttctaacact   2520
gaaccagaag aagccataca aactcgcaca gtgataaatc agcacggtgt atccgagact   2580
ctagtggaga attttctcag tagagcagct ttggtatcaa agagaagttt tgaatacaaa   2640
gatcatactt cgtctgcagc acaagcagac aagaactttt tcaaatggac aattaacacc   2700
agatcctttg tacagttaag aagaaaatta gaattattca catacccttag atttgatgct   2760
gagatcacta tactcacaac tgtagcagtg aatggtagtg gtaataatac atacgtgggt   2820
cttcctgact tgacactcca agcaatgttt gtacccactg gtgctcttac cccagaaaaa   2880
caggactcat tccactggca gtcaggcagt aatgctagtg tattctttaa aatctccgac   2940
cccccagcca gaataaccat accttttatg tgcattaact cagcatactc agttttttat   3000
gatggctttg ccggatttga gaaaaacggt ctgtatggaa taaatccagc tgacactatt   3060
ggtaacttat gtgttagaat agtgaatgaa caccaaccag ttggtttcac agtgaccgtt   3120
agggtttaca tgaagcctaa acacataaaa gcatgggcac cacgaccacc acgaactttg   3180
```

```
ccatatatga gtattgcaaa tgcaaattac aaaggtaaag aaagagcacc aaatgcgctc   3240
aatgctataa ttggcaatag agacagtgtc aaaaccatgc ctcataatat agtgaacact   3300
ggtccaggct tcggaggagt ttttgtaggg tctttcaaaa taatcaacta tcacttggcc   3360
actacagaag agagacagtc agctatctat gtggattggc aatcagacgt cttggttacc   3420
cccattgctg ctcatggaag gcaccaaata gcaagatgca agtgcaacac aggggtttac   3480
tattgtaggc acaaaaacag aagttacccg atttgctttg aaggcccagg gattcaatgg   3540
attgaacaaa atgaatatta cccagcaagg taccagacca atgtactatt ggcagttggt   3600
cctgcggaag caggagattg cggtggttta ctagtttgtc cacatggggt aatcggtctt   3660
cttacagcag gagggggtgg aattgtagct ttcactgata tcaggaattt gctatggtta   3720
gatactgatg ctatggaaca aggcattact gattatattc aaaatcttgg taatgccttt   3780
ggagcaggat ttacagaaac aatctctaat aaagccaagg aagtgcaaga tatgctaatt   3840
ggagagagtt cactattaga aaaattgtta aaagctctaa tcaaaatcat atcagcatta   3900
gtaattgtaa tcagaaactc agaagattta gtcacagtca cagccacact agcattgttg   3960
ggatgccatg attcaccatg gagctacttg aaacagaagg tatgttcata cttaggtatt   4020
ccttatgtac ctagacaggg tgaatcgtgg cttaagaaat tcacagaggc atgcaatgct   4080
cttagaggtc tggattggct atcgcaaaag atagataaat tcatcaactg gcttaaaacc   4140
aaaatattac cagaagctag ggagaaatat gaatttgtgc aaaggctcaa acagttaccg   4200
gtgatagaaa accaagttag tacaatcgag catagctgcc caacaacaga acaacaacag   4260
gccttattca acaacgtcca atactattca cactactgta gaaagtacgc accactttac   4320
gcagtggaag caaagagggt agtagctctt gaaaagaaaa taaacaacta catccagttc   4380
aagtccaaat ctcgcattga accggtttgt ttaataatac atggctctcc aggaactggc   4440
aagtcagtgg cttcaaattt aattgccagg gctatcacag agaaattggg gggggacatt   4500
tattccttgc ctccagaccc taaatatttt gatggataca aacagcaaac agtggtcctc   4560
atggatgatt taatgcaaaa tccagatggg aatgacatat ctatgttctg ccaaatggtc   4620
tccactgtag atttcatacc cccaatggct agtttggagg aaaaaggaac tctatacacc   4680
agtccatttt taatagctac taccaatgct ggctcaatac atgcaccaac tgtatcagac   4740
tcaaaggctt tgtcacgcag atttaaattt gacgtggaca ttgaagtcac agattcatac   4800
aaggactcaa ataaattgga tatgtcaagg gcagtcgaga tgtgcaaacc agatggctgt   4860
gcccccacca attacaaaag atgctgccca ttgatctgtg gaaaggctat ccaattcaga   4920
gatcgcagaa ctaatgcaag atccactatt gatatgctag taactgatat tataaaggaa   4980
tatagaacca gaaacagtac acaggataag ctggaagctc tgtttcaggg gcctccacag   5040
tttaaagaga tcaaaatttc agtcacccca gatacaccag ctcctgatgc tataaatgac   5100
cttcttaggt cagtggattc tcaagaagtt agggattatt gccaaaagaa aggatggatt   5160
gtagtacacc catcaaatga gctaatagta gaaaaacaca ttagtagagc ttttattact   5220
ctacaagcca ttgccacctt tgtatcaata gctggtgtag tttatgttat atacaaactt   5280
tttgctggca ttcagggtcc atacacagga atccccaatc ctaaacctaa agtaccctct   5340
ctcagaacag ctaaagtgca aggaccaggg ttcgattttg cacaagccat aatgaagaaa   5400
aataccgtca ttgcaaggac tgaaaagggt gagttcacca tgctgggtgt atatgatagg   5460
gtagcggtca tccccacaca cgcatctgtt ggagaaacca tttacattaa tgatgtagag   5520
```

```
actaaagttt tagatgcgtg tgcacttaga gacttgactg atacaaactt agagataacc   5580

atagtcaaat tagaccgtaa tcaaaaattt agagatatca gacattttct gcccagatat   5640

gaggatgatt acaatgacgc tgtgcttagc gtacatacat caaaattccc aaatatgtat   5700

atcccagttg gacaagtcac caattatggc ttcttgaacc taggtggtac accgacgcac   5760

cgcattttaa tgtataactt cccaacaaga gctggccagt gtggtggtgt ggtgacaact   5820

acaggtaagg tgataggaat acatgtaggt ggaaatggag ctcaaggatt tgcagcaatg   5880

ctactacact cttacttttc cgatacacaa ggtgagatag ttagtagtga aaagagtggg   5940

gtgtgcatta acgcaccggc aaagactaaa ctccaaccta gtgttttcca tcaagttttt   6000

gaaggttcaa aggaaccagc agttctcaat ccaaaagatc ctaggcttaa aacagatttc   6060

gaggaggcca ttttctcaaa gtacacaggt aacaaaatta tgttaatgga tgagtacatg   6120

gaagaggcag tggatcatta tgtggggtgt ttagaaccat tagacatcag tgtggatccc   6180

ataccccctgg aaagtgccat gtatggaatg gatggccttg aggcattaga cttaactacc   6240

agtgcaggat tcccttactt actacaaggg aagaagaaaa gggatatatt taatagacat   6300

actagagaca ccagtgaaat gacaaaaatg ttagagaaat atggagttga cctacctttt   6360

gtaacctttg taaaagatga gcttagatca agagaaaaag ttgaaaaagg gaaatcacgc   6420

ctgattgagg ccagttcctt gaatgactca gttgctatga gagttgcctt tggaaacctt   6480

tacgccacat ttcacaacaa tccaggtaca gcaactggta gtgcagttgg ttgtgatcca   6540

gatatatttt ggtcaaaaat ccctattttg ttagatggag aaatctttgc ttttgactac   6600

actggttatg atgctagttt gtcaccagtg tggtttgcct gcttaaagaa agttctaatt   6660

aagttaggtt acacacatca aacgtctttt atagattatt tgtgtcattc agtacattta   6720

tataaggaca aaaaatacat agttaatggt ggaatgccct ctggttcttc aggcaccagc   6780

atattcaaca ctatgatcaa caatataatc ataagaactt tattaattag ggtttacaaa   6840

ggcatagacc tggaccagtt caaaatgatt gcctatgggg atgatgttat tgctagctac   6900

ccacataaga ttgatccagg tttgctggca gaagcaggta aacagtatgg attagtaatg   6960

acgccagcag acaaaggaac cagttttatt gacacaaatt gggaaaatgt aactttctta   7020

aaaagatatt tcagagcaga tgatcaatac ccctttctca tacatccagt gatgccaatg   7080

aaagagatac atgaatctat tagatggact aaagatccca gaaacacaca ggatcatgtt   7140

aggtctttgt gctacctcgc atggcataat ggagaggagg cttataatga attttgcaga   7200

aaaatcagaa gtgtgcctgt gggaagagca ttgacactac ctgcatactc tagtcttaga   7260

cggaaatggt tagattcgtt ctagacaact ctaattgaaa cccaagttat agttactttc   7320

atttagaggt aaattttggt cacttggggg ccaaaaaaaa aaaaaaaaaa aaaaaaagtc   7380

gac                                                                7383
```

```
<210> SEQ ID NO 2
<211> LENGTH: 507
<212> TYPE: RNA
<213> ORGANISM: Artificial Sequence
<220> FEATURE:
<223> OTHER INFORMATION: RNA sequence of the internal ribosome entry
      site of HRV2

<400> SEQUENCE: 2

aacuuagaag uuuuucacaa agaccaauag ccgguaauca gccagauuac ugaaggucaa     60

gcacuucugu uuccccgguc aauguugaua ugcuccaaca gggcaaaaac aacugcgauc    120
```

-continued

```
guuaaccgca aagcgccuac gcaaagcuua guagcaucuu ugaaaucguu uggcuggucg    180

auccgccauu uccccuggua gaccuggcag augaggcuag aaauacccca cuggcgacag    240

uguucuagcc ugcguggcug ccugcacacc cuaugggugu gaagccaaac aauggacaag    300

gugugaagag ccccgugugc ucgcuuugag uccuccggcc ccugaaugug gcuaaccuua    360

acccugcagc uagagcacgu aacccaaugu guaucuaguc guaaugagca auugcgggau    420

gggaccaacu acuuugggug uccguguuuc acuuuuuccu uuauauuugc uuauggugac    480

aauauauaca auauauauau uggcacc                                        507


<210> SEQ ID NO 3
<211> LENGTH: 22
<212> TYPE: RNA
<213> ORGANISM: Artificial Sequence
<220> FEATURE:
<223> OTHER INFORMATION: RNA sequence of the target sequence of miR-133

<400> SEQUENCE: 3

acagcugguu gaaggggacc aa                                              22


<210> SEQ ID NO 4
<211> LENGTH: 22
<212> TYPE: RNA
<213> ORGANISM: Artificial Sequence
<220> FEATURE:
<223> OTHER INFORMATION: RNA sequence of the target sequence of miR-206

<400> SEQUENCE: 4

ccacacacuu ccuuacauuc ca                                              22


<210> SEQ ID NO 5
<211> LENGTH: 102
<212> TYPE: RNA
<213> ORGANISM: Artificial Sequence
<220> FEATURE:
<223> OTHER INFORMATION: RNA sequence of tandem sequence of miR-133
      target sequence and miR-206 target sequence

<400> SEQUENCE: 5

acagcugguu gaaggggacc aacgauacag cugguugaag gggaccaaac cgguccacac     60

acuuccuuac auuccaucac ccacacacuu ccuuacauuc ca                       102


<210> SEQ ID NO 6
<211> LENGTH: 435
<212> TYPE: DNA
<213> ORGANISM: Artificial Sequence
<220> FEATURE:
<223> OTHER INFORMATION: DNA sequence of GM-CSF gene

<400> SEQUENCE: 6

atgtggctgc agagcctgct gctcttgggc actgtggcct gcagcatctc tgcacccgcc     60

cgctcgccca gccccagcac gcagccctgg gagcatgtga atgccatcca ggaggcccgg    120

cgtctcctga acctgagtag agacactgct gctgagatga atgaaacagt agaagtcatc    180

tcagaaatgt ttgacctcca ggagccgacc tgcctacaga cccgcctgga gctgtacaag    240

cagggcctgc ggggcagcct caccaagctc aagggcccct tgaccatgat ggccagccac    300

tacaagcagc actgccctcc aaccccggaa acttcctgtg caacccagat tatcaccttt    360

gaaagtttca aagagaacct gaaggacttt ctgcttgtca tcccctttga ctgctgggag    420

ccagtccagg agtga                                                     435
```

<210> SEQ ID NO 7
<211> LENGTH: 795
<212> TYPE: DNA
<213> ORGANISM: Artificial Sequence
<220> FEATURE:
<223> OTHER INFORMATION: DNA sequence encoding Anti-PD-1 scFv

<400> SEQUENCE: 7
atgaagcacc tgtggttctt cctgctgctg gtggccgctc ctaggtgggt gctgtcccag 60
gtgcagctgg tgcagagcgg cgtggaggtg aagaagcccg gcgcttccgt gaaggtgtcc 120
tgcaaggcct ccggctacac cttcaccaac tactacatgt actgggtgag gcaggcccct 180
ggacagggac tggagtggat gggcggcatc aacccttcca acggcggcac caacttcaac 240
gagaagttca agaaccgggt gaccctgacc accgactcct ccaccaccac cgcctacatg 300
gagctgaagt ccctgcagtt tgacgacacc gccgtgtact actgcgccag gagggactac 360
cggttcgaca tgggcttcga ctactggggc cagggcacaa ccgtgaccgt gtccagcgga 420
ggtggcggat ctggaggggg tggtagcggt ggaggcggga gtgagatcgt gctgacccag 480
tcccctgcta cactgtccct gtcccccggc gagagggcta cactgagctg cagggcctcc 540
aagggcgtgt ccacctccgg ctactcctac ctgcactggt accagcagaa gcctggacag 600
gctcccaggc tgctgatcta cctggcctcc tacctggagt ccggcgtgcc tgctaggttt 660
tccggcagcg gcagcggcac cgatttcacc ctgaccatct cctccctgga gcccgaggac 720
ttcgccgtgt actactgcca gcactccagg gatctgcctc tgaccttcgg cggcggcacc 780
aaggtggaga tcaag 795

<210> SEQ ID NO 8
<211> LENGTH: 7306
<212> TYPE: DNA
<213> ORGANISM: Artificial Sequence
<220> FEATURE:
<223> OTHER INFORMATION: cDNA sequence of EV-D68-HRV2

<400> SEQUENCE: 8
taatacgact cactataggt taaaacagcc ttggggttgt tcccactcca agggcccacg 60
tggcggctag tactctggta cttcggtacc tttgtacgcc tgttttatct cccttcccaa 120
tgtaacttag aagaacttag aagtttttca caaagaccaa tagccggtaa tcagccagat 180
tactgaaggt caagcacttc tgtttccccg gtcaatgttg atatgctcca acagggcaaa 240
aacaactgcg atcgttaacc gcaaagcgcc tacgcaaagc ttagtagcat ctttgaaatc 300
gtttggctgg tcgatccgcc atttcccctg gtagacctgg cagatgaggc tagaaatacc 360
ccactggcga cagtgttcta gcctgcgtgg ctgcctgcac accctatggg tgtgaagcca 420
aacaatggac aaggtgtgaa gagccccgtg tgctcgcttt gagtcctccg gcccctgaat 480
gtggctaacc ttaaccctgc agctagagca cgtaacccaa tgtgtatcta gtcgtaatga 540
gcaattgcgg gatgggacca actactttgg gtgtccgtgt ttcacttttt cctttatatt 600
tgcttatggt gacaatatat acaatatata tattggcacc atgggagctc aggttactag 660
acaacaaact ggcactcatg aaaatgccaa cattgccaca aatggatctc atatcacata 720
caatcagata aacttttaca aggatagcta tgcggcttca gccagcaagc aggatttttc 780
acaggaccca tcaaaattca ctgaaccagt agtggaaggt ttaaaagcag gggcgccagt 840
tttgaaatct cctagtgctg aggcatgtgg ctacagtgat agagtattac agctcaaatt 900
aggaaattca gctattgtca cccaggaagc agcgaactac tgctgcgctt atggtgaatg 960

-continued

```
gcccaattac ttaccagacc atgaagcagt agccattgat aaacctacac aaccagaaac   1020
tgctacagat agattctaca ctttgaaatc agtcaaatgg gaaactggaa gcacaggatg   1080
gtggtggaaa ctacccgatg cactgaataa tataggcatg tttggacaga atgtgcagca   1140
tcactaccta tatagatctg gtttcttgat tcatgtgcag tgtaatgcca caaaattcca   1200
tcaaggtgcc ttattagtgg tagcaattcc agaacatcag aggggagcgc acaacaccaa   1260
cactagccca gggtttgatg atataatgaa aggtgaagaa ggagggacct tcaatcatcc   1320
atatgtcctt gatgatggaa catcattggc ttgtgcgacg atatttccac atcagtggat   1380
aaatctgaga accaacaatt cagcaacaat tgttcttccc tggatgaatg ctgctccaat   1440
ggatttccca cttagacata atcagtggac gctagcaata ataccagtgg tgccattagg   1500
tacgcgtaca acatcaagta tggtcccaat aacagtttca atcgctccaa tgtgttgtga   1560
gtttaatgga cttagacacg ccattactca aggtgtccca acataccttt taccaggctc   1620
gggacaattc ctaacaactg atgatcatag ctctgcacca gctctcccgt gtttcaaccc   1680
aactccagaa atgcatatcc cagggcaggt ccgtaacatg ctagaagtgg tccaagtgga   1740
atcaatgatg gagattaata acacagaaag tgcagttggc atggagcgtc ttaaggttga   1800
tatatcagca ttgacagatg tcgatcaatt gttattcaac attccactgg acatacagtt   1860
ggatgggcca cttagaaaca ctttggtagg aaacatatct agatattaca ctcattggtc   1920
tggatcccta gaaatgacgt ttatgttttg tggcagcttc atggcaacgg gaaaattaat   1980
cctgtgctat actcctccag gtggatcatg cccgacaacc agagagaccg ccatgttagg   2040
tacacatatt gtttgggatt ttggattaca atctagtgta accctgataa taccttggat   2100
tagtggatcc cactacagga tgtttaataa tgatgctaag tcaactaatg ccaacgttgg   2160
ctatgtcact tgttttatgc agaccaatct gatagtcccc agtgaatcct ctgacacgtg   2220
ttccttgata gggttcatag cagcaaaaga tgatttctcc ctcagattaa tgagagacag   2280
ccctgacatt ggacaactag accatttaca tgcagcagag gcagcctacc agatcgagag   2340
catcatcaaa acagcgaccg acactgtgaa aagtgagatt aatgctgaac ttggtgtggt   2400
ccctagctta aatgcagttg aaacaggtgc aacttctaac actgaaccag aagaagccat   2460
acaaactcgc acagtgataa atcagcacgg tgtatccgag actctagtgg agaattttct   2520
cagtagagca gctttggtat caaagagaag ttttgaatac aaagatcata cttcgtctgc   2580
agcacaagca gacaagaact tttcaaatg gacaattaac accagatcct ttgtacagtt   2640
aagaagaaaa ttagaattat tcacatacct tagatttgat gctgagatca ctatactcac   2700
aactgtagca gtgaatggta gtggtaataa tacatacgtg ggtcttcctg acttgacact   2760
ccaagcaatg tttgtaccca ctggtgctct taccccagaa aaacaggact cattccactg   2820
gcagtcaggc agtaatgcta gtgtattctt taaaatctcc gaccccccag ccagaataac   2880
catacctttt atgtgcatta actcagcata ctcagttttt tatgatggct ttgccggatt   2940
tgagaaaaac ggtctgtatg gaataaatcc agctgacact attggtaact tatgtgttag   3000
aatagtgaat gaacaccaac cagttggttt cacagtgacc gttagggttt acatgaagcc   3060
taaacacata aaagcatggg caccacgacc accacgaact ttgccatata tgagtattgc   3120
aaatgcaaat tacaaaggta aagaaagagc accaaatgcg ctcaatgcta taattggcaa   3180
tagagacagt gtcaaaacca tgcctcataa tatagtgaac actggtccag gcttcggagg   3240
agtttttgta gggtctttca aaataatcaa ctatcacttg gccactacag aagagagaca   3300
```

-continued

```
gtcagctatc tatgtggatt ggcaatcaga cgtcttggtt acccccattg ctgctcatgg   3360
aaggcaccaa atagcaagat gcaagtgcaa cacaggggtt tactattgta ggcacaaaaa   3420
cagaagttac ccgatttgct ttgaaggccc agggattcaa tggattgaac aaaatgaata   3480
ttacccagca aggtaccaga ccaatgtact attggcagtt ggtcctgcgg aagcaggaga   3540
ttgcggtggt ttactagttt gtccacatgg ggtaatcggt cttcttacag caggaggggg   3600
tggaattgta gctttcactg atatcaggaa tttgctatgg ttagatactg atgctatgga   3660
acaaggcatt actgattata ttcaaaatct tggtaatgcc tttggagcag gatttacaga   3720
aacaatctct aataaagcca aggaagtgca agatatgcta attggagaga gttcactatt   3780
agaaaaattg ttaaaagctc taatcaaaat catatcagca ttagtaattg taatcagaaa   3840
ctcagaagat ttagtcacag tcacagccac actagcattg ttgggatgcc atgattcacc   3900
atggagctac ttgaaacaga aggtatgttc atacttaggt attccttatg tacctagaca   3960
gggtgaatcg tggcttaaga aattcacaga ggcatgcaat gctcttagag gtctggattg   4020
gctatcgcaa aagatagata aattcatcaa ctggcttaaa accaaaatat taccagaagc   4080
tagggagaaa tatgaatttg tgcaaaggct caaacagtta ccggtgatag aaaaccaagt   4140
tagtacaatc gagcatagct gcccaacaac agaacaacaa caggccttat tcaacaacgt   4200
ccaatactat tcacactact gtagaaagta cgcaccactt tacgcagtgg aagcaaagag   4260
ggtagtagct cttgaaaaga aaataaacaa ctacatccag ttcaagtcca aatctcgcat   4320
tgaaccggtt tgtttaataa tacatggctc tccaggaact ggcaagtcag tggcttcaaa   4380
tttaattgcc agggctatca cagagaaatt ggggggggac atttattcct tgcctccaga   4440
ccctaaatat tttgatggat acaaacagca aacagtggtc ctcatggatg atttaatgca   4500
aaatccagat gggaatgaca tatctatgtt ctgccaaatg gtctccactg tagatttcat   4560
acccccaatg gctagtttgg aggaaaaagg aactctatac accagtccat ttttaatagc   4620
tactaccaat gctggctcaa tacatgcacc aactgtatca gactcaaagg ctttgtcacg   4680
cagatttaaa tttgacgtgg acattgaagt cacagattca tacaaggact caaataaatt   4740
ggatatgtca agggcagtcg agatgtgcaa accagatggc tgtgccccca ccaattacaa   4800
aagatgctgc ccattgatct gtggaaaggc tatccaattc agagatcgca gaactaatgc   4860
aagatccact attgatatgc tagtaactga tattataaag gaatatagaa ccagaaacag   4920
tacacaggat aagctggaag ctctgtttca ggggcctcca cagtttaaag agatcaaaat   4980
ttcagtcacc ccagatacac cagctcctga tgctataaat gaccttctta ggtcagtgga   5040
ttctcaagaa gttagggatt attgccaaaa gaaaggatgg attgtagtac acccatcaaa   5100
tgagctaata gtagaaaaac acattagtag agcttttatt actctacaag ccattgccac   5160
ctttgtatca atagctggtg tagtttatgt tatatacaaa ctttttgctg gcattcaggg   5220
tccatacaca ggaatcccca atcctaaacc taaagtaccc tctctcagaa cagctaaagt   5280
gcaaggacca gggttcgatt ttgcacaagc cataatgaag aaaaataccg tcattgcaag   5340
gactgaaaag ggtgagttca ccatgctggg tgtatatgat agggtagcgg tcatccccac   5400
acacgcatct gttggagaaa ccatttacat taatgatgta gagactaaag ttttagatgc   5460
gtgtgcactt agagacttga ctgatacaaa cttagagata accatagtca aattagaccg   5520
taatcaaaaa tttagagata tcagacattt tctgcccaga tatgaggatg attacaatga   5580
cgctgtgctt agcgtacata catcaaaatt cccaaatatg tatatcccag ttggacaagt   5640
caccaattat ggcttcttga acctaggtgg tacaccgacg caccgcattt taatgtataa   5700
```

```
cttcccaaca agagctggcc agtgtggtgg tgtggtgaca actacaggta aggtgatagg   5760

aatacatgta ggtggaaatg gagctcaagg atttgcagca atgctactac actcttactt   5820

ttccgataca caaggtgaga tagttagtag tgaaaagagt ggggtgtgca ttaacgcacc   5880

ggcaaagact aaactccaac ctagtgtttt ccatcaagtt tttgaaggtt caaaggaacc   5940

agcagttctc aatccaaaag atcctaggct taaaacagat ttcgaggagg ccattttctc   6000

aaagtacaca ggtaacaaaa ttatgttaat ggatgagtac atggaagagg cagtggatca   6060

ttatgtgggg tgtttagaac cattagacat cagtgtggat cccatacccc tggaaagtgc   6120

catgtatgga atggatggcc ttgaggcatt agacttaact accagtgcag gattccctta   6180

cttactacaa gggaagaaga aaagggatat atttaataga catactagag acaccagtga   6240

aatgacaaaa atgttagaga aatatggagt tgacctacct tttgtaacct ttgtaaaaga   6300

tgagcttaga tcaagagaaa aagttgaaaa agggaaatca cgcctgattg aggccagttc   6360

cttgaatgac tcagttgcta tgagagttgc ctttggaaac ctttacgcca catttcacaa   6420

caatccaggt acagcaactg gtagtgcagt tggttgtgat ccagatatat tttggtcaaa   6480

aatccctatt ttgttagatg gagaaatctt tgcttttgac tacactggtt atgatgctag   6540

tttgtcacca gtgtggtttg cctgcttaaa gaaagttcta attaagttag gttacacaca   6600

tcaaacgtct tttatagatt atttgtgtca ttcagtacat ttatataagg acaaaaaata   6660

catagttaat ggtggaatgc cctctggttc ttcaggcacc agcatattca acactatgat   6720

caacaatata atcataagaa ctttattaat tagggtttac aaaggcatag acctggacca   6780

gttcaaaatg attgcctatg ggatgatgt tattgctagc tacccacata agattgatcc   6840

aggtttgctg gcagaagcag gtaaacagta tggattagta atgacgccag cagacaaagg   6900

aaccagtttt attgacacaa attgggaaaa tgtaactttc ttaaaaagat atttcagagc   6960

agatgatcaa taccccttc tcatacatcc agtgatgcca atgaaagaga tacatgaatc   7020

tattagatgg actaaagatc ccagaaacac acaggatcat gttaggtctt tgtgctacct   7080

cgcatggcat aatggagagg aggcttataa tgaattttgc agaaaaatca gaagtgtgcc   7140

tgtgggaaga gcattgacac tacctgcata ctctagtctt agacggaaat ggttagattc   7200

gttctagaca actctaattg aaacccaagt tatagttact ttcatttaga ggtaaatttt   7260

ggtcacttgg gggccaaaaa aaaaaaaaaa aaaaaaaaaa gtcgac                7306
```

<210> SEQ ID NO 9
<211> LENGTH: 7485
<212> TYPE: DNA
<213> ORGANISM: Artificial Sequence
<220> FEATURE:
<223> OTHER INFORMATION: cDNA sequence of EV-D68-miR133&206T

<400> SEQUENCE: 9

```
taatacgact cactataggt taaaacagcc ttggggttgt tcccactcca agggcccacg     60

tggcggctag tactctggta cttcggtacc tttgtacgcc tgttttatct cccttcccaa    120

tgtaacttag aagttcttaa atcaatgctc aataggtggg gcgcaaacca gcgctctcat    180

gagcaagcac tcctgtctcc ccggtgaggt tgtataaact gttcccacgg ttgaaaacaa    240

cctatccgtt atccgctata gtacttcgag aaacctagta ccacctttgg attgttgacg    300

cgttgcgctc agcacactaa cccgtgtgta gcttgggtcg atgagtctgg acatacctca    360

ctggcgacag tggtccaggc tgcgttggcg gcctactcat ggtgaaagcc atgagacgct    420
```

```
agacatgaac aaggtgtgaa gagtctattg agctactata gagtcctccg gcccctgaat    480
gcggctaatc ctaaccatgg agcaagtgct cacaggccag tgagttgctt gtcgtaatgc    540
gcaagtccgt ggcggaaccg actactttgg gtgtccgtgt ttcacttttt acttttatga    600
ctgcttatgg tgacaatttg atattgttac catttagctt gtcaaatcaa ttgcaaaaga    660
tcctaaatct tatttatcaa cttgcatctt gataacttta atttgaaaat tttaacaatg    720
ggagctcagg ttactagaca acaaactggc actcatgaaa atgccaacat tgccacaaat    780
ggatctcata tcacatacaa tcagataaac ttttacaagg atagctatgc ggcttcagcc    840
agcaagcagg atttttcaca ggacccatca aaattcactg aaccagtagt ggaaggttta    900
aaagcagggg cgccagtttt gaaatctcct agtgctgagg catgtggcta cagtgataga    960
gtattacagc tcaaattagg aaattcagct attgtcaccc aggaagcagc gaactactgc   1020
tgcgcttatg gtgaatggcc caattactta ccagaccatg aagcagtagc cattgataaa   1080
cctacacaac cagaaactgc tacagataga ttctacactt tgaaatcagt caaatgggaa   1140
actggaagca caggatggtg gtggaaacta cccgatgcac tgaataatat aggcatgttt   1200
ggacagaatg tgcagcatca ctacctatat agatctggtt tcttgattca tgtgcagtgt   1260
aatgccacaa aattccatca aggtgcctta ttagtggtag caattccaga acatcagagg   1320
ggagcgcaca acaccaacac tagcccaggg tttgatgata taatgaaagg tgaagaagga   1380
gggaccttca atcatccata tgtccttgat gatggaacat cattggcttg tgcgacgata   1440
tttccacatc agtggataaa tctgagaacc aacaattcag caacaattgt tcttccctgg   1500
atgaatgctg ctccaatgga tttcccactt agacataatc agtggacgct agcaataata   1560
ccagtggtgc cattaggtac gcgtacaaca tcaagtatgg tcccaataac agtttcaatc   1620
gctccaatgt gttgtgagtt taatggactt agacacgcca ttactcaagg tgtcccaaca   1680
tacctttttac caggctcggg acaattccta acaactgatg atcatagctc tgcaccagct   1740
ctcccgtgtt tcaacccaac tccagaaatg catatcccag ggcaggtccg taacatgcta   1800
gaagtggtcc aagtggaatc aatgatggag attaataaca cagaaagtgc agttggcatg   1860
gagcgtctta aggttgatat atcagcattg acagatgtcg atcaattgtt attcaacatt   1920
ccactggaca tacagttgga tgggccactt agaaacactt tggtaggaaa catatctaga   1980
tattacactc attggtctgg atccctagaa atgacgttta tgttttgtgg cagcttcatg   2040
gcaacgggaa aattaatcct gtgctatact cctccaggtg gatcatgccc gacaaccaga   2100
gagaccgcca tgttaggtac acatattgtt tgggattttg gattacaatc tagtgtaacc   2160
ctgataatac cttggattag tggatcccac tacaggatgt ttaataatga tgctaagtca   2220
actaatgcca acgttggcta tgtcacttgt tttatgcaga ccaatctgat agtccccagt   2280
gaatcctctg acacgtgttc cttgataggg ttcatagcag caaaagatga tttctccctc   2340
agattaatga gagacagccc tgacattgga caactagacc atttacatgc agcagaggca   2400
gcctaccaga tcgagagcat catcaaaaca gcgaccgaca ctgtgaaaag tgagattaat   2460
gctgaacttg gtgtggtccc tagcttaaat gcagttgaaa caggtgcaac ttctaacact   2520
gaaccagaag aagccataca aactcgcaca gtgataaatc agcacggtgt atccgagact   2580
ctagtggaga attttctcag tagagcagct ttggtatcaa agagaagttt tgaatacaaa   2640
gatcatactt cgtctgcagc acaagcagac aagaactttt tcaaatggac aattaacacc   2700
agatcctttg tacagttaag aagaaaatta gaattattca catacccttag atttgatgct   2760
gagatcacta tactcacaac tgtagcagtg aatggtagtg gtaataatac atacgtgggt   2820
```

```
cttcctgact tgacactcca agcaatgttt gtacccactg gtgctcttac cccagaaaaa   2880
caggactcat tccactggca gtcaggcagt aatgctagtg tattctttaa aatctccgac   2940
cccccagcca gaataaccat accttttatg tgcattaact cagcatactc agttttttat   3000
gatggctttg ccggatttga gaaaaacggt ctgtatggaa taaatccagc tgacactatt   3060
ggtaacttat gtgttagaat agtgaatgaa caccaaccag ttggtttcac agtgaccgtt   3120
agggtttaca tgaagcctaa acacataaaa gcatgggcac cacgaccacc acgaactttg   3180
ccatatatga gtattgcaaa tgcaaattac aaaggtaaag aaagagcacc aaatgcgctc   3240
aatgctataa ttggcaatag agacagtgtc aaaaccatgc ctcataatat agtgaacact   3300
ggtccaggct tcggaggagt tttgtaggg tctttcaaaa taatcaacta tcacttggcc   3360
actacagaag agagacagtc agctatctat gtggattggc aatcagacgt cttggttacc   3420
cccattgctg ctcatggaag gcaccaaata gcaagatgca agtgcaacac aggggtttac   3480
tattgtaggc acaaaaacag aagttacccg atttgctttg aaggcccagg gattcaatgg   3540
attgaacaaa atgaatatta cccagcaagg taccagacca atgtactatt ggcagttggt   3600
cctgcggaag caggagattg cggtggttta ctagtttgtc cacatggggt aatcggtctt   3660
cttacagcag gagggggtgg aattgtagct ttcactgata tcaggaattt gctatggtta   3720
gatactgatg ctatggaaca aggcattact gattatattc aaaatcttgg taatgccttt   3780
ggagcaggat ttacagaaac aatctctaat aaagccaagg aagtgcaaga tatgctaatt   3840
ggagagagtt cactattaga aaaattgtta aaagctctaa tcaaaatcat atcagcatta   3900
gtaattgtaa tcagaaactc agaagattta gtcacagtca cagccacact agcattgttg   3960
ggatgccatg attcaccatg gagctacttg aaacagaagg tatgttcata cttaggtatt   4020
ccttatgtac ctagacaggg tgaatcgtgg cttaagaaat tcacagaggc atgcaatgct   4080
cttagaggtc tggattggct atcgcaaaag atagataaat tcatcaactg gcttaaaacc   4140
aaaatattac cagaagctag ggagaaatat gaatttgtgc aaaggctcaa acagttaccg   4200
gtgatagaaa accaagttag tacaatcgag catagctgcc caacaacaga acaacaacag   4260
gccttattca acaacgtcca atactattca cactactgta gaaagtacgc accactttac   4320
gcagtggaag caaagagggt agtagctctt gaaaagaaaa taaacaacta catccagttc   4380
aagtccaaat ctcgcattga accggtttgt ttaataatac atggctctcc aggaactggc   4440
aagtcagtgg cttcaaattt aattgccagg gctatcacag agaaattggg gggggacatt   4500
tattccttgc ctccagaccc taaatatttt gatggataca aacagcaaac agtggtcctc   4560
atggatgatt taatgcaaaa tccagatggg aatgacatat ctatgttctg ccaaatggtc   4620
tccactgtag atttcatacc cccaatggct agtttggagg aaaaaggaac tctatacacc   4680
agtccatttt taatagctac taccaatgct ggctcaatac atgcaccaac tgtatcagac   4740
tcaaaggctt tgtcacgcag atttaaattt gacgtggaca ttgaagtcac agattcatac   4800
aaggactcaa ataaattgga tatgtcaagg gcagtcgaga tgtgcaaacc agatggctgt   4860
gcccccacca attacaaaag atgctgccca ttgatctgtg gaaaggctat ccaattcaga   4920
gatcgcagaa ctaatgcaag atccactatt gatatgctag taactgatat tataaaggaa   4980
tatagaacca gaaacagtac acaggataag ctggaagctc tgtttcaggg gcctccacag   5040
tttaaagaga tcaaaatttc agtcacccca gatacaccag ctcctgatgc tataaatgac   5100
cttcttaggt cagtggattc tcaagaagtt agggattatt gccaaaagaa aggatggatt   5160
```

```
gtagtacacc catcaaatga gctaatagta gaaaaacaca ttagtagagc ttttattact   5220
ctacaagcca ttgccacctt tgtatcaata gctggtgtag tttatgttat atacaaactt   5280
tttgctggca ttcagggtcc atacacagga atccccaatc ctaaacctaa agtaccctct   5340
ctcagaacag ctaaagtgca aggaccaggg ttcgattttg cacaagccat aatgaagaaa   5400
aataccgtca ttgcaaggac tgaaaagggt gagttcacca tgctgggtgt atatgatagg   5460
gtagcggtca tccccacaca cgcatctgtt ggagaaacca tttacattaa tgatgtagag   5520
actaaagttt tagatgcgtg tgcacttaga gacttgactg atacaaactt agagataacc   5580
atagtcaaat tagaccgtaa tcaaaaattt agagatatca gacattttct gcccagatat   5640
gaggatgatt acaatgacgc tgtgcttagc gtacatacat caaaattccc aaatatgtat   5700
atcccagttg gacaagtcac caattatggc ttcttgaacc taggtggtac accgacgcac   5760
cgcattttaa tgtataactt cccaacaaga gctggccagt gtggtggtgt ggtgacaact   5820
acaggtaagg tgataggaat acatgtaggt ggaaatggag ctcaaggatt tgcagcaatg   5880
ctactacact cttacttttc cgatacacaa ggtgagatag ttagtagtga aaagagtggg   5940
gtgtgcatta acgcaccggc aaagactaaa ctccaaccta gtgttttcca tcaagttttt   6000
gaaggttcaa aggaaccagc agttctcaat ccaaaagatc ctaggcttaa aacagatttc   6060
gaggaggcca ttttctcaaa gtacacaggt aacaaaatta tgttaatgga tgagtacatg   6120
gaagaggcag tggatcatta tgtggggtgt ttagaaccat tagacatcag tgtggatccc   6180
atacccctgg aaagtgccat gtatggaatg gatggccttg aggcattaga cttaactacc   6240
agtgcaggat tcccttactt actacaaggg aagaagaaaa gggatatatt taatagacat   6300
actagagaca ccagtgaaat gacaaaaatg ttagagaaat atggagttga cctacctttt   6360
gtaacctttg taaaagatga gcttagatca agagaaaaag ttgaaaaagg gaaatcacgc   6420
ctgattgagg ccagttcctt gaatgactca gttgctatga gagttgcctt tggaaacctt   6480
tacgccacat ttcacaacaa tccaggtaca gcaactggta gtgcagttgg ttgtgatcca   6540
gatatatttt ggtcaaaaat ccctattttg ttagatggag aaatctttgc ttttgactac   6600
actggttatg atgctagttt gtcaccagtg tggtttgcct gcttaaagaa agttctaatt   6660
aagttaggtt acacacatca aacgtctttt atagattatt tgtgtcattc agtacattta   6720
tataaggaca aaaaatacat agttaatggt ggaatgccct ctggttcttc aggcaccagc   6780
atattcaaca ctatgatcaa caatataatc ataagaactt tattaattag ggtttacaaa   6840
ggcatagacc tggaccagtt caaaatgatt gcctatgggg atgatgttat tgctagctac   6900
ccacataaga ttgatccagg tttgctggca gaagcaggta aacagtatgg attagtaatg   6960
acgccagcag acaaaggaac cagttttatt gacacaaatt gggaaaatgt aactttctta   7020
aaaagatatt tcagagcaga tgatcaatac ccctttctca tacatccagt gatgccaatg   7080
aaagagatac atgaatctat tagatggact aaagatccca gaaacacaca ggatcatgtt   7140
aggtctttgt gctacctcgc atggcataat ggagaggagg cttataatga attttgcaga   7200
aaaatcagaa gtgtgcctgt gggaagagca ttgacactac ctgcatactc tagtcttaga   7260
cggaaatggt tagattcgtt ctagacaact ctaacagctg gttgaagggg accaacgata   7320
cagctggttg aaggggacca aaccggtcca cacacttcct tacattccat cacccacaca   7380
cttccttaca ttccaattga aacccaagtt atagttactt tcatttagag gtaaattttg   7440
gtcacttggg ggccaaaaaa aaaaaaaaaa aaaaaaaaag tcgac                   7485
```

<210> SEQ ID NO 10
<211> LENGTH: 7860
<212> TYPE: DNA
<213> ORGANISM: Artificial Sequence
<220> FEATURE:
<223> OTHER INFORMATION: cDNA sequence of EV-D68-GM-CSF

<400> SEQUENCE: 10

```
taatacgact cactataggt taaaacagcc ttggggttgt tcccactcca agggcccacg     60
tggcggctag tactctggta cttcggtacc tttgtacgcc tgttttatct cccttcccaa    120
tgtaacttag aagttcttaa atcaatgctc aataggtggg gcgcaaacca gcgctctcat    180
gagcaagcac tcctgtctcc ccggtgaggt tgtataaact gttcccacgg ttgaaaacaa    240
cctatccgtt atccgctata gtacttcgag aaacctagta ccacctttgg attgttgacg    300
cgttgcgctc agcacactaa cccgtgtgta gcttgggtcg atgagtctgg acatacctca    360
ctggcgacag tggtccaggc tgcgttggcg gcctactcat ggtgaaagcc atgagacgct    420
agacatgaac aaggtgtgaa gagtctattg agctactata gagtcctccg gcccctgaat    480
gcggctaatc ctaaccatgg agcaagtgct cacaggccag tgagttgctt gtcgtaatgc    540
gcaagtccgt ggcggaaccg actactttgg gtgtccgtgt ttcacttttt acttttatga    600
ctgcttatgg tgacaatttg atattgttac catttagctt gtcaaatcaa ttgcaaaaga    660
tcctaaatct tatttatcaa cttgcatctt gataacttta atttgaaaat tttaacaatg    720
ggagctcagg ttactagaca acaaactggc actcatgaaa atgccaacat tgccacaaat    780
ggatctcata tcacatacaa tcagataaac ttttacaagg atagctatgc ggcttcagcc    840
agcaagcagg atttttcaca ggacccatca aaattcactg aaccagtagt ggaaggttta    900
aaagcagggg cgccagtttt gaaatctcct agtgctgagg catgtggcta cagtgataga    960
gtattacagc tcaaattagg aaattcagct attgtcaccc aggaagcagc gaactactgc   1020
tgcgcttatg gtgaatggcc caattactta ccagaccatg aagcagtagc cattgataaa   1080
cctacacaac cagaaactgc tacagataga ttctacactt tgaaatcagt caaatgggaa   1140
actggaagca caggatggtg gtggaaacta cccgatgcac tgaataatat aggcatgttt   1200
ggacagaatg tgcagcatca ctacctatat agatctggtt tcttgattca tgtgcagtgt   1260
aatgccacaa aattccatca aggtgcctta ttagtggtag caattccaga acatcagagg   1320
ggagcgcaca acaccaacac tagcccaggg tttgatgata taatgaaagg tgaagaagga   1380
gggaccttca atcatccata tgtccttgat gatggaacat cattggcttg tgcgacgata   1440
tttccacatc agtggataaa tctgagaacc aacaattcag caacaattgt tcttccctgg   1500
atgaatgctg ctccaatgga tttcccactt agacataatc agtggacgct agcaataata   1560
ccagtggtgc cattaggtac gcgtacaaca tcaagtatgg tcccaataac agtttcaatc   1620
gctccaatgt gttgtgagtt taatggactt agacacgcca ttactcaagg tgtcccaaca   1680
taccttttac caggctcggg acaattccta acaactgatg atcatagctc tgcaccagct   1740
ctcccgtgtt tcaacccaac tccagaaatg catatcccag ggcaggtccg taacatgcta   1800
gaagtggtcc aagtggaatc aatgatggag attaataaca cagaaagtgc agttggcatg   1860
gagcgtctta aggttgatat atcagcattg acagatgtcg atcaattgtt attcaacatt   1920
ccactggaca tacagttgga tgggccactt agaaacactt tggtaggaaa catatctaga   1980
tattacactc attggtctgg atccctagaa atgacgttta tgttttgtgg cagcttcatg   2040
gcaacgggaa aattaatcct gtgctatact cctccaggtg gatcatgccc gacaaccaga   2100
```

```
gagaccgcca tgttaggtac acatattgtt tgggattttg gattacaatc tagtgtaacc   2160
ctgataatac cttggattag tggatcccac tacaggatgt ttaataatga tgctaagtca   2220
actaatgcca acgttggcta tgtcacttgt tttatgcaga ccaatctgat agtccccagt   2280
gaatcctctg acacgtgttc cttgataggg ttcatagcag caaaagatga tttctccctc   2340
agattaatga gagacagccc tgacattgga caactagacc atttacatgc agcagaggca   2400
gcctaccaga tcgagagcat catcaaaaca gcgaccgaca ctgtgaaaag tgagattaat   2460
gctgaacttg gtgtggtccc tagcttaaat gcagttgaaa caggtgcaac ttctaacact   2520
gaaccagaag aagccataca aactcgcaca gtgataaatc agcacggtgt atccgagact   2580
ctagtggaga attttctcag tagagcagct ttggtatcaa agagaagttt tgaatacaaa   2640
gatcatactt cgtctgcagc acaagcagac aagaactttt tcaaatggac aattaacacc   2700
agatcctttg tacagttaag aagaaaatta gaattattca catactttag atttgatgct   2760
gagatcacta tactcacaac tgtagcagtg aatggtagtg gtaataatac atacgtgggt   2820
cttcctgact tgacactcca agcaatgttt gtacccactg gtgctcttac cccagaaaaa   2880
caggactcat tccactggca gtcaggcagt aatgctagtg tattctttaa aatctccgac   2940
cccccagcca gaataaccat accttttatg tgcattaact cagcatactc agtttttttat   3000
gatggctttg ccggatttga gaaaaacggt ctgtatggaa taaatccagc tgacactatt   3060
ggtaacttat gtgttagaat agtgaatgaa caccaaccag ttggtttcac agtgaccgtt   3120
agggtttaca tgaagcctaa acacataaaa gcatgggcac cacgaccacc acgaactttg   3180
ccatatatga gtattgcaaa tgcaaattac aaaggtaaag aaagagcacc aaatgcgctc   3240
aatgctataa ttggcaatag agacagtgtc aaaaccatgc ctcataatat agtgaacact   3300
ggtccaggct tctggctgca gagcctgctg ctcttgggca ctgtggcctg cagcatctct   3360
gcacccgccc gctcgcccag ccccagcacg cagccctggg agcatgtgaa tgccatccag   3420
gaggcccggc gtctcctgaa cctgagtaga gacactgctg ctgagatgaa tgaaacagta   3480
gaagtcatct cagaaatgtt tgacctccag gagccgacct gcctacagac ccgcctggag   3540
ctgtacaagc agggcctgcg gggcagcctc accaagctca agggcccctt gaccatgatg   3600
gccagccact acaagcagca ctgccctcca accccggaaa cttcctgtgc aacccagatt   3660
atcacctttg aaagtttcaa agagaacctg aaggactttc tgcttgtcat cccctttgac   3720
tgctgggagc cagtccagga gagtgtcaaa accatgcctc ataatatagt gaacactggt   3780
ccaggcttcg gaggagtttt tgtagggtct ttcaaaataa tcaactatca cttggccact   3840
acagaagaga gacagtcagc tatctatgtg gattggcaat cagacgtctt ggttaccccc   3900
attgctgctc atggaaggca ccaaatagca agatgcaagt gcaacacagg ggtttactat   3960
tgtaggcaca aaaacagaag ttacccgatt tgctttgaag gcccagggat tcaatggatt   4020
gaacaaaatg aatattaccc agcaaggtac cagaccaatg tactattggc agttggtcct   4080
gcggaagcag gagattgcgg tggtttacta gtttgtccac atggggtaat cggtcttctt   4140
acagcaggag ggggtggaat tgtagctttc actgatatca ggaatttgct atggttagat   4200
actgatgcta tggaacaagg cattactgat tatattcaaa atcttggtaa tgcctttgga   4260
gcaggattta cagaaacaat ctctaataaa gccaaggaag tgcaagatat gctaattgga   4320
gagagttcac tattagaaaa attgttaaaa gctctaatca aaatcatatc agcattagta   4380
attgtaatca gaaactcaga agatttagtc acagtcacag ccacactagc attgttggga   4440
tgccatgatt caccatggag ctacttgaaa cagaaggtat gttcatactt aggtattcct   4500
```

```
tatgtaccta gacagggtga atcgtggctt aagaaattca cagaggcatg caatgctctt   4560
agaggtctgg attggctatc gcaaaagata gataaattca tcaactggct taaaaccaaa   4620
atattaccag aagctaggga gaaatatgaa tttgtgcaaa ggctcaaaca gttaccggtg   4680
atagaaaacc aagttagtac aatcgagcat agctgcccaa caacagaaca acaacaggcc   4740
ttattcaaca acgtccaata ctattcacac tactgtagaa agtacgcacc actttacgca   4800
gtggaagcaa agagggtagt agctcttgaa aagaaaataa acaactacat ccagttcaag   4860
tccaaatctc gcattgaacc ggtttgttta ataatacatg gctctccagg aactggcaag   4920
tcagtggctt caaatttaat tgccagggct atcacagaga aattgggggg ggacatttat   4980
tccttgcctc cagaccctaa atattttgat ggatacaaac agcaaacagt ggtcctcatg   5040
gatgatttaa tgcaaaatcc agatgggaat gacatatcta tgttctgcca aatggtctcc   5100
actgtagatt tcataccccc aatggctagt ttggaggaaa aaggaactct atacaccagt   5160
ccatttttaa tagctactac caatgctggc tcaatacatg caccaactgt atcagactca   5220
aaggctttgt cacgcagatt taaatttgac gtggacattg aagtcacaga ttcatacaag   5280
gactcaaata aattggatat gtcaagggca gtcgagatgt gcaaaccaga tggctgtgcc   5340
cccaccaatt acaaaagatg ctgcccattg atctgtggaa aggctatcca attcagagat   5400
cgcagaacta atgcaagatc cactattgat atgctagtaa ctgatattat aaaggaatat   5460
agaaccagaa acagtacaca ggataagctg gaagctctgt ttcaggggcc tccacagttt   5520
aaagagatca aaatttcagt caccccagat acaccagctc ctgatgctat aaatgacctt   5580
cttaggtcag tggattctca agaagttagg gattattgcc aaaagaaagg atggattgta   5640
gtacacccat caaatgagct aatagtagaa aaacacatta gtagagcttt tattactcta   5700
caagccattg ccacctttgt atcaatagct ggtgtagttt atgttatata caaacttttt   5760
gctggcattc agggtccata cacaggaatc cccaatccta aacctaaagt accctctctc   5820
agaacagcta aagtgcaagg accagggttc gattttgcac aagccataat gaagaaaaat   5880
accgtcattg caaggactga aaagggtgag ttcaccatgc tgggtgtata tgatagggta   5940
gcggtcatcc ccacacacgc atctgttgga gaaaccattt acattaatga tgtagagact   6000
aaagttttag atgcgtgtgc acttagagac ttgactgata caaacttaga gataaccata   6060
gtcaaattag accgtaatca aaaatttaga gatatcagac attttctgcc cagatatgag   6120
gatgattaca atgacgctgt gcttagcgta catacatcaa aattcccaaa tatgtatatc   6180
ccagttggac aagtcaccaa ttatggcttc ttgaacctag gtggtacacc gacgcaccgc   6240
attttaatgt ataacttccc aacaagagct ggccagtgtg gtggtgtggt gacaactaca   6300
ggtaaggtga taggaataca tgtaggtgga aatggagctc aaggatttgc agcaatgcta   6360
ctacactctt acttttccga tacacaaggt gagatagtta gtagtgaaaa gagtggggtg   6420
tgcattaacg caccggcaaa gactaaactc caacctagtg ttttccatca agtttttgaa   6480
ggttcaaagg aaccagcagt tctcaatcca aaagatccta ggcttaaaac agatttcgag   6540
gaggccattt tctcaaagta cacaggtaac aaaattatgt taatggatga gtacatggaa   6600
gaggcagtgg atcattatgt ggggtgttta gaaccattag acatcagtgt ggatcccata   6660
cccctggaaa gtgccatgta tggaatggat ggccttgagg cattagactt aactaccagt   6720
gcaggattcc cttacttact acaagggaag aagaaaaggg atatatttaa tagacatact   6780
agagacacca gtgaaatgac aaaaatgtta gagaaatatg gagttgacct accttttgta   6840
```

```
acctttgtaa aagatgagct tagatcaaga gaaaaagttg aaaaagggaa atcacgcctg   6900
attgaggcca gttccttgaa tgactcagtt gctatgagag ttgcctttgg aaacctttac   6960
gccacatttc acaacaatcc aggtacagca actggtagtg cagttggttg tgatccagat   7020
atattttggt caaaaatccc tattttgtta gatggagaaa tctttgcttt tgactacact   7080
ggttatgatg ctagtttgtc accagtgtgg tttgcctgct taaagaaagt tctaattaag   7140
ttaggttaca cacatcaaac gtcttttata gattatttgt gtcattcagt acatttatat   7200
aaggacaaaa aatacatagt taatggtgga atgccctctg gttcttcagg caccagcata   7260
ttcaacacta tgatcaacaa tataatcata agaactttat taattagggt ttacaaaggc   7320
atagacctgg accagttcaa aatgattgcc tatggggatg atgttattgc tagctaccca   7380
cataagattg atccaggttt gctggcagaa gcaggtaaac agtatggatt agtaatgacg   7440
ccagcagaca aaggaaccag ttttattgac acaaattggg aaaatgtaac tttcttaaaa   7500
agatatttca gagcagatga tcaatacccc tttctcatac atccagtgat gccaatgaaa   7560
gagatacatg aatctattag atggactaaa gatcccagaa acacacagga tcatgttagg   7620
tctttgtgct acctcgcatg gcataatgga gaggaggctt ataatgaatt ttgcagaaaa   7680
atcagaagtg tgcctgtggg aagagcattg acactacctg catactctag tcttagacgg   7740
aaatggttag attcgttcta gacaactcta attgaaaccc aagttatagt tactttcatt   7800
tagaggtaaa ttttggtcac ttgggggcca aaaaaaaaaa aaaaaaaaaa aaaagtcgac   7860
```

```
<210> SEQ ID NO 11
<211> LENGTH: 8226
<212> TYPE: DNA
<213> ORGANISM: Artificial Sequence
<220> FEATURE:
<223> OTHER INFORMATION: cDNA sequence of EV-D68-Anti-PD1

<400> SEQUENCE: 11
```

```
taatacgact cactataggt taaaacagcc ttggggttgt tcccactcca agggcccacg     60
tggcggctag tactctggta cttcggtacc tttgtacgcc tgttttatct cccttcccaa    120
tgtaacttag aagttcttaa atcaatgctc aataggtggg gcgcaaacca gcgctctcat    180
gagcaagcac tcctgtctcc ccggtgaggt tgtataaact gttcccacgg ttgaaaacaa    240
cctatccgtt atccgctata gtacttcgag aaacctagta ccacctttgg attgttgacg    300
cgttgcgctc agcacactaa cccgtgtgta gcttgggtcg atgagtctgg acatacctca    360
ctggcgacag tggtccaggc tgcgttggcg gcctactcat ggtgaaagcc atgagacgct    420
agacatgaac aaggtgtgaa gagtctattg agctactata gagtcctccg gcccctgaat    480
gcggctaatc ctaaccatgg agcaagtgct cacaggccag tgagttgctt gtcgtaatgc    540
gcaagtccgt ggcggaaccg actactttgg gtgtccgtgt ttcacttttt acttttatga    600
ctgcttatgg tgacaatttg atattgttac catttagctt gtcaaatcaa ttgcaaaaga    660
tcctaaatct tatttatcaa cttgcatctt gataacttta atttgaaaat tttaacaatg    720
ggagctcagg ttactagaca acaaactggc actcatgaaa atgccaacat tgccacaaat    780
ggatctcata tcacatacaa tcagataaac ttttacaagg atagctatgc ggcttcagcc    840
agcaagcagg atttttcaca ggacccatca aaattcactg aaccagtagt ggaaggttta    900
aaagcagggg cgccagtttt gaaatctcct agtgctgagg catgtggcta cagtgataga    960
gtattacagc tcaaattagg aaattcagct attgtcaccc aggaagcagc gaactactgc   1020
tgcgcttatg gtgaatggcc caattactta ccagaccatg aagcagtagc cattgataaa   1080
```

```
cctacacaac cagaaactgc tacagataga ttctacactt tgaaatcagt caaatgggaa   1140
actggaagca caggatggtg gtggaaacta cccgatgcac tgaataatat aggcatgttt   1200
ggacagaatg tgcagcatca ctacctatat agatctggtt tcttgattca tgtgcagtgt   1260
aatgccacaa aattccatca aggtgcctta ttagtggtag caattccaga acatcagagg   1320
ggagcgcaca acaccaacac tagcccaggg tttgatgata taatgaaagg tgaagaagga   1380
gggaccttca atcatccata tgtccttgat gatggaacat cattggcttg tgcgacgata   1440
tttccacatc agtggataaa tctgagaacc aacaattcag caacaattgt tcttccctgg   1500
atgaatgctg ctccaatgga tttcccactt agacataatc agtggacgct agcaataata   1560
ccagtggtgc cattaggtac gcgtacaaca tcaagtatgg tcccaataac agtttcaatc   1620
gctccaatgt gttgtgagtt taatggactt agacacgcca ttactcaagg tgtcccaaca   1680
tacctttac caggctcggg acaattccta acaactgatg atcatagctc tgcaccagct   1740
ctcccgtgtt tcaacccaac tccagaaatg catatcccag ggcaggtccg taacatgcta   1800
gaagtggtcc aagtggaatc aatgatggag attaataaca cagaaagtgc agttggcatg   1860
gagcgtctta aggttgatat atcagcattg acagatgtcg atcaattgtt attcaacatt   1920
ccactggaca tacagttgga tgggccactt agaaacactt tggtaggaaa catatctaga   1980
tattacactc attggtctgg atccctagaa atgacgttta tgttttgtgg cagcttcatg   2040
gcaacgggaa aattaatcct gtgctatact cctccaggtg gatcatgccc gacaaccaga   2100
gagaccgcca tgttaggtac acatattgtt tgggattttg gattacaatc tagtgtaacc   2160
ctgataatac cttggattag tggatcccac tacaggatgt ttaataatga tgctaagtca   2220
actaatgcca acgttggcta tgtcacttgt tttatgcaga ccaatctgat agtccccagt   2280
gaatcctctg acacgtgttc cttgataggg ttcatagcag caaaagatga tttctccctc   2340
agattaatga gagacagccc tgacattgga caactagacc atttacatgc agcagaggca   2400
gcctaccaga tcgagagcat catcaaaaca gcgaccgaca ctgtgaaaag tgagattaat   2460
gctgaacttg gtgtggtccc tagcttaaat gcagttgaaa caggtgcaac ttctaacact   2520
gaaccagaag aagccataca aactcgcaca gtgataaatc agcacggtgt atccgagact   2580
ctagtggaga attttctcag tagagcagct ttggtatcaa agagaagttt tgaatacaaa   2640
gatcatactt cgtctgcagc acaagcagac aagaactttt tcaaatggac aattaacacc   2700
agatcctttg tacagttaag aagaaaatta gaattattca cataccttag atttgatgct   2760
gagatcacta tactcacaac tgtagcagtg aatggtagtg gtaataatac atacgtgggt   2820
cttcctgact tgacactcca agcaatgttt gtacccactg gtgctcttac cccagaaaaa   2880
caggactcat tccactggca gtcaggcagt aatgctagtg tattctttaa aatctccgac   2940
cccccagcca gaataaccat accttttatg tgcattaact cagcatactc agttttttat   3000
gatggctttg ccggatttga gaaaaacggt ctgtatggaa taaatccagc tgacactatt   3060
ggtaacttat gtgttagaat agtgaatgaa caccaaccag ttggtttcac agtgaccgtt   3120
agggtttaca tgaagcctaa acacataaaa gcatgggcac cacgaccacc acgaactttg   3180
ccatatatga gtattgcaaa tgcaaattac aaaggtaaag aaagagcacc aaatgcgctc   3240
aatgctataa ttggcaatag agacagtgtc aaaaccatgc ctcataatat agtgaacact   3300
ggtccaggct tcatgaagca cctgtggttc ttcctgctgc tggtggccgc tcctaggtgg   3360
gtgctgtccc aggtgcagct ggtgcagagc ggcgtggagg tgaagaagcc cggcgcttcc   3420
```

-continued

```
gtgaaggtgt cctgcaaggc ctccggctac accttcacca actactacat gtactgggtg   3480
aggcaggccc ctggacaggg actggagtgg atgggcggca tcaacccttc caacggcggc   3540
accaacttca acgagaagtt caagaaccgg gtgaccctga ccaccgactc ctccaccacc   3600
accgcctaca tggagctgaa gtccctgcag tttgacgaca ccgccgtgta ctactgcgcc   3660
aggagggact accggttcga catgggcttc gactactggg gccagggcac aaccgtgacc   3720
gtgtccagcg gaggtggcgg atctggaggg ggtggtagcg gtggaggcgg gagtgagatc   3780
gtgctgaccc agtcccctgc tacactgtcc ctgtcccccg gcgagagggc tacactgagc   3840
tgcagggcct ccaagggcgt gtccacctcc ggctactcct acctgcactg gtaccagcag   3900
aagcctggac aggctcccag gctgctgatc tacctggcct cctacctgga gtccggcgtg   3960
cctgctaggt tttccggcag cggcagcggc accgatttca ccctgaccat ctcctccctg   4020
gagcccgagg acttcgccgt gtactactgc cagcactcca gggatctgcc tctgaccttc   4080
ggcggcggca ccaaggtgga gatcaagagt gtcaaaacca tgcctcataa tatagtgaac   4140
actggtccag gcttcggagg agtttttgta gggtctttca aataatcaa ctatcacttg   4200
gccactacag aagagagaca gtcagctatc tatgtggatt ggcaatcaga cgtcttggtt   4260
acccccattg ctgctcatgg aaggcaccaa atagcaagat gcaagtgcaa cacaggggtt   4320
tactattgta ggcacaaaaa cagaagttac ccgatttgct ttgaaggccc agggattcaa   4380
tggattgaac aaaatgaata ttacccagca aggtaccaga ccaatgtact attggcagtt   4440
ggtcctgcgg aagcaggaga ttgcggtggt ttactagttt gtccacatgg ggtaatcggt   4500
cttcttacag caggaggggg tggaattgta gctttcactg atatcaggaa tttgctatgg   4560
ttagatactg atgctatgga acaaggcatt actgattata ttcaaaatct tggtaatgcc   4620
tttggagcag gatttacaga aacaatctct aataaagcca aggaagtgca agatatgcta   4680
attggagaga gttcactatt agaaaaattg ttaaaagctc taatcaaaat catatcagca   4740
ttagtaattg taatcagaaa ctcagaagat ttagtcacag tcacagccac actagcattg   4800
ttgggatgcc atgattcacc atggagctac ttgaaacaga aggtatgttc atacttaggt   4860
attccttatg tacctagaca gggtgaatcg tggcttaaga aattcacaga ggcatgcaat   4920
gctcttagag gtctggattg gctatcgcaa aagatagata aattcatcaa ctggcttaaa   4980
accaaaatat taccagaagc tagggagaaa tatgaatttg tgcaaaggct caaacagtta   5040
ccggtgatag aaaaccaagt tagtacaatc gagcatagct gcccaacaac agaacaacaa   5100
caggccttat tcaacaacgt ccaatactat tcacactact gtagaaagta cgcaccactt   5160
tacgcagtgg aagcaaagag ggtagtagct cttgaaaaga aaataaacaa ctacatccag   5220
ttcaagtcca aatctcgcat tgaaccggtt tgtttaataa tacatggctc tccaggaact   5280
ggcaagtcag tggcttcaaa tttaattgcc agggctatca cagagaaatt ggggggggac   5340
atttattcct tgcctccaga ccctaaatat tttgatggat acaaacagca aacagtggtc   5400
ctcatggatg atttaatgca aaatccagat gggaatgaca tatctatgtt ctgccaaatg   5460
gtctccactg tagatttcat acccccaatg gctagtttgg aggaaaaagg aactctatac   5520
accagtccat ttttaatagc tactaccaat gctggctcaa tacatgcacc aactgtatca   5580
gactcaaagg ctttgtcacg cagatttaaa tttgacgtgg acattgaagt cacagattca   5640
tacaaggact caaataaatt ggatatgtca agggcagtcg agatgtgcaa accagatggc   5700
tgtgccccca ccaattacaa aagatgctgc ccattgatct gtggaaaggc tatccaattc   5760
agagatcgca gaactaatgc aagatccact attgatatgc tagtaactga tattataaag   5820
```

```
gaatatagaa ccagaaacag tacacaggat aagctggaag ctctgtttca ggggcctcca   5880
cagtttaaag agatcaaaat ttcagtcacc ccagatacac cagctcctga tgctataaat   5940
gaccttctta ggtcagtgga ttctcaagaa gttagggatt attgccaaaa gaaaggatgg   6000
attgtagtac acccatcaaa tgagctaata gtagaaaaac acattagtag agcttttatt   6060
actctacaag ccattgccac ctttgtatca atagctggtg tagtttatgt tatatacaaa   6120
ctttttgctg gcattcaggg tccatacaca ggaatcccca atcctaaacc taaagtaccc   6180
tctctcagaa cagctaaagt gcaaggacca gggttcgatt ttgcacaagc cataatgaag   6240
aaaaataccg tcattgcaag gactgaaaag ggtgagttca ccatgctggg tgtatatgat   6300
agggtagcgg tcatccccac acacgcatct gttggagaaa ccatttacat taatgatgta   6360
gagactaaag ttttagatgc gtgtgcactt agagacttga ctgatacaaa cttagagata   6420
accatagtca aattagaccg taatcaaaaa tttagagata tcagacattt tctgcccaga   6480
tatgaggatg attacaatga cgctgtgctt agcgtacata catcaaaatt cccaaatatg   6540
tatatcccag ttggacaagt caccaattat ggcttcttga acctaggtgg tacaccgacg   6600
caccgcattt taatgtataa cttcccaaca agagctggcc agtgtggtgg tgtggtgaca   6660
actacaggta aggtgatagg aatacatgta ggtggaaatg gagctcaagg atttgcagca   6720
atgctactac actcttactt ttccgataca caaggtgaga tagttagtag tgaaaagagt   6780
ggggtgtgca ttaacgcacc ggcaaagact aaactccaac ctagtgtttt ccatcaagtt   6840
tttgaaggtt caaaggaacc agcagttctc aatccaaaag atcctaggct taaaacagat   6900
ttcgaggagg ccattttctc aaagtacaca ggtaacaaaa ttatgttaat ggatgagtac   6960
atggaagagg cagtggatca ttatgtgggg tgtttagaac cattagacat cagtgtggat   7020
cccataccccc tggaaagtgc catgtatgga atggatggcc ttgaggcatt agacttaact   7080
accagtgcag gattccctta cttactacaa gggaagaaga aaagggatat atttaataga   7140
catactagag acaccagtga aatgacaaaa atgttagaga aatatggagt tgacctacct   7200
tttgtaacct ttgtaaaaga tgagcttaga tcaagagaaa aagttgaaaa agggaaatca   7260
cgcctgattg aggccagttc cttgaatgac tcagttgcta tgagagttgc ctttggaaac   7320
ctttacgcca catttcacaa caatccaggt acagcaactg gtagtgcagt tggttgtgat   7380
ccagatatat tttggtcaaa aatccctatt ttgttagatg gagaaatctt tgcttttgac   7440
tacactggtt atgatgctag tttgtcacca gtgtggtttg cctgcttaaa gaaagttcta   7500
attaagttag gttacacaca tcaaacgtct tttatagatt atttgtgtca ttcagtacat   7560
ttatataagg acaaaaaata catagttaat ggtggaatgc cctctggttc ttcaggcacc   7620
agcatattca acactatgat caacaatata atcataagaa ctttattaat tagggtttac   7680
aaaggcatag acctggacca gttcaaaatg attgcctatg gggatgatgt tattgctagc   7740
tacccacata agattgatcc aggtttgctg gcagaagcag gtaaacagta tggattagta   7800
atgacgccag cagacaaagg aaccagtttt attgacacaa attgggaaaa tgtaactttc   7860
ttaaaaagat atttcagagc agatgatcaa taccccttttc tcatacatcc agtgatgcca   7920
atgaaagaga tacatgaatc tattagatgg actaaagatc ccagaaacac acaggatcat   7980
gttaggtctt tgtgctacct cgcatggcat aatggagagg aggcttataa tgaattttgc   8040
agaaaaatca gaagtgtgcc tgtgggaaga gcattgacac tacctgcata ctctagtctt   8100
agacggaaat ggttagattc gttctagaca actctaattg aaacccaagt tatagttact   8160
```

```
ttcatttaga ggtaaatttt ggtcacttgg gggccaaaaa aaaaaaaaaa aaaaaaaaaa   8220

gtcgac                                                               8226


<210> SEQ ID NO 12
<211> LENGTH: 7383
<212> TYPE: RNA
<213> ORGANISM: Artificial Sequence
<220> FEATURE:
<223> OTHER INFORMATION: Genomic sequence of EV-D68-WT

<400> SEQUENCE: 12

uaauacgacu cacuauaggu uaaaacagcc uuggggguugu ucccacucca agggcccacg     60

uggcggcuag uacucuggua cuucgguacc uuuguacgcc uguuuuaucu cccuucccaa    120

uguaacuuag aaguucuuaa aucaaugcuc aauaggugggg gcgcaaacca gcgcucucau    180

gagcaagcac uccugucucc ccggugaggu uguauaaacu guucccacgg uugaaaacaa    240

ccuauccguu auccgcuaua guacuucgag aaaccuagua ccaccuuugg auuguugacg    300

cguugcgcuc agcacacuaa cccgugugua gcuugggucg augagucugg acauaccuca    360

cuggcgacag ugguccaggc ugcguuggcg gccuacucau ggugaaagcc augagacgcu    420

agacaugaac aaggugugaa gagucuauug agcuacuaua gaguccuccg gccccugaau    480

gcggcuaauc cuaaccaugg agcaagugcu cacaggccag ugaguugcuu gucguaaugc    540

gcaaguccgu ggcggaaccg acuacuuugg guguccgugu uucacuuuuu acuuuuauga    600

cugcuuaugg ugacaauuug auauuguuac cauuuagcuu gucaaaucaa uugcaaaaga    660

uccuaaaucu uauuuaucaa cuugcaucuu gauaacuuua auuugaaaau uuuaacaaug    720

ggagcucagg uuacuagaca acaaacuggc acucaugaaa augccaacau ugccacaaau    780

ggaucucaua ucacauacaa ucagauaaac uuuuacaagg auagcuaugc ggcuucagcc    840

agcaagcagg auuuuucaca ggacccauca aaauucacug aaccaguagu ggaagguuua    900

aaagcagggg cgccaguuuu gaaaucuccu agugcugagg cauguggcua cagugauaga    960

guauuacagc ucaaauuagg aaauucagcu auugucaccc aggaagcagc gaacuacugc   1020

ugcgcuuaug gugaauggcc caauuacuua ccagaccaug aagcaguagc cauugauaaa   1080

ccuacacaac cagaaacugc uacagauaga uucuacacuu ugaaaucagu caaaugggaa   1140

acuggaagca caggauggug guggaaacua cccgaugcac ugaauaaauau aggcauguuu  1200

ggacagaaug ugcagcauca cuaccuauau agaucugguu ucuugauuca ugugcagugu   1260

aaugccacaa aauuccauca aggugccuua uuagugguag caauuccaga acaucagagg   1320

ggagcgcaca acaccaacac uagcccaggg uuugaugaua uaaugaaagg ugaagaagga   1380

gggaccuuca aucauccaua uguccuugau gauggaacau cauuggcuug ugcgacgaua   1440

uuuccacauc aguggauaaa ucugagaacc aacaauucag caacaauugu ucuucccugg   1500

augaaugcug cuccaaugga uuucccacuu agacauaauc aguggacgcu agcaauaaua   1560

ccaguggugc cauuagguac gcguacaaca ucaaguaugg ucccaauaac aguuucaauc   1620

gcuccaaugu guugugaguu uaauggacuu agacacgcca uuacucaagg ugucccaaca   1680

uaccuuuuac caggcucggg acaauuccua acaacugaug aucauagcuc ugcaccagcu   1740

cuccccguguu ucaacccaac uccagaaaug cauaucccag ggcagguccg uaacaugcua  1800

gaaguggucc aaguggaauc aaugauggag auuaauaaca cagaaagugc aguuggcaug   1860

gagcgucuua agguugauau aucagcauug acagaugucg aucaauuguu auucaacauu   1920

ccacuggaca uacaguugga ugggccacuu agaaacacuu ugguaggaaa cauaucuaga   1980
```

-continued

```
uauuacacuc auuggucugg aucccuagaa augacguuua uguuuugugg cagcuucaug   2040
gcaacgggaa aauuaauccu gugcuauacu ccuccaggug gaucaugccc gacaaccaga   2100
gagaccgcca uguuagguac acauauuguu ugggauuuug gauuacaauc uaguguaacc   2160
cugauaauac cuuggauuag uggaucccac uacaggaugu uuaauaauga ugcuaaguca   2220
acuaaugcca acguuggcua ugucacuugu uuuaugcaga ccaaucugau aguccccagu   2280
gaauccucug acacguguuc cuugauaggg uucauagcag caaaagauga uuucuccuc   2340
agauuaauga gagacagccc ugacauugga caacuagacc auuuacaugc agcagaggca   2400
gccuaccaga ucgagagcau caucaaaaca gcgaccgaca cugugaaaag ugagauuaau   2460
gcugaacuug guguggucccc uagcuuaaau gcaguugaaa caggugcaac uucuaacacu   2520
gaaccagaag aagccauaca aacucgcaca gugauaaauc agcacggugu auccgagacu   2580
cuaguggaga auuuucucag uagagcagcu uugguaucaa agagaaguuu ugaauacaaa   2640
gaucauacuu cgucugcagc acaagcagac aagaacuuuu ucaaauggac aauuaacacc   2700
agauccuuug uacaguuaag aagaaaauua gaauuauuca cauaccuuag auuugaugcu   2760
gagaucacua uacucacaac uguagcagug aaugguagug guaauaauac auacguggu   2820
cuuccugacu ugacacucca agcaauguuu guacccacug gugcucuuac cccagaaaaa   2880
caggacucau uccacuggca gucaggcagu aaugcuagug uauucuuuaa aaucuccgac   2940
cccccagcca gaauaaccau accuuuuaug ugcauuaacu cagcauacuc aguuuuuuau   3000
gauggcuuug ccggauuuga gaaaaacggu cuguauggaa uaaauccagc ugacacuauu   3060
gguaacuuau guguuagaau agugaaugaa caccaaccag uugguuucac agugaccguu   3120
aggguuuaca ugaagccuaa acacauaaaa gcaugggcac cacgaccacc acgaacuuug   3180
ccauauauga guauugcaaa ugcaaauuac aaagguaaag aaagagcacc aaaugcgcuc   3240
aaugcuauaa uuggcaauag agacaguguc aaaaccaugc cucauaauau agugaacacu   3300
gguccaggcu ucggaggagu uuuuguaggg ucuuucaaaa uaaucaacua ucacuuggcc   3360
acuacagaag agagacaguc agcuaucuau guggauuggc aaucagacgu cuugguuacc   3420
cccauugcug cucauggaag gcaccaaaua gcaagaugca agugcaacac aggggguuuac   3480
uauuguaggc acaaaaacag aaguuacccg auuugcuuug aaggcccagg gauucaaugg   3540
auugaacaaa augaauauua cccagcaagg uaccagacca auguacuauu ggcaguuggu   3600
ccugcggaag caggagauug cggugguuua cuaguuuguc cacaugggu aaucggucuu   3660
cuuacagcag gagggggugg aauuguagcu uucacugaua ucaggaauuu gcuaugguua   3720
gauacugaug cuauggaaca aggcauuacu gauuauauuc aaaaucuugg uaaugccuuu   3780
ggagcaggau uuacagaaac aaucucuaau aaagccaagg aagugcaaga uaugcuaauu   3840
ggagagaguu cacuauuaga aaaauuguua aaagcucuaa ucaaaaucau aucagcauua   3900
guaauuguaa ucagaaacuc agaagauuua gucacaguca cagccacacu agcauuguug   3960
ggaugccaug auucaccaug gagcuacuug aaacagaagg uauguucaua cuuagguauu   4020
ccuuauguac cuagacaggg ugaaucgugg cuuaagaaau ucacagaggc augcaaugcu   4080
cuuagagguc uggauuggcu aucgcaaaag auagauaaau ucaucaacug gcuuaaaacc   4140
aaaauauuac cagaagcuag ggagaaauau gaauuugugc aaaggcucaa acaguuaccg   4200
gugauagaaa accaaguuag uacaaucgag cauagcugcc caacaacaga acaacaacag   4260
gccuuauuca acaacgucca auacuauuca cacuacugua gaaaguacgc accacuuuac   4320
```

```
gcaguggaag caaagagggu aguagcucuu gaaaagaaaa uaaacaacua cauccaguuc   4380
aaguccaaau cucgcauuga accgguuugu uuaauaauac auggcucucc aggaacuggc   4440
aagucagugg cuucaaauuu aauugccagg gcuaucacag agaaauuggg gggggacauu   4500
uauuccuugc cuccagaccc uaaauauuuu gauggauaca aacagcaaac aguggucuc    4560
auggaugauu uaaugcaaaa uccagauggg aaugacauau cuauguucug ccaaaugguc   4620
uccacuguag auuucauacc cccaauggcu aguuuggagg aaaaaggaac ucuauacacc   4680
aguccauuuu uaauagcuac uaccaaugcu ggcucaauac augcaccaac uguaucagac   4740
ucaaaggcuu ugucacgcag auuuaaauuu gacguggaca uugaagucac agauucauac   4800
aaggacucaa auaaauugga uaugucaagg gcagucgaga ugugcaaacc agauggcugu   4860
gcccccacca auuacaaaag augcugccca uugaucugug gaaaggcuau ccaauucaga   4920
gaucgcagaa cuaaugcaag auccacuauu gauaugcuag uaacugauau uauaaaggaa   4980
uauagaacca gaaacaguac acaggauaag cuggaagcuc uguuucaggg gccuccacag   5040
uuuaaagaga ucaaaauuuc agucacccca gauacaccag cuccugaugc uauaaaugac   5100
cuucuuaggu caguggauuc ucaagaaguu agggauuauu gccaaaagaa aggauggauu   5160
guaguacacc caucaaauga gcuaauagua gaaaaacaca uuaguagagc uuuuauuacu   5220
cuacaagcca uugccaccuu uguaucaaua gcuggugag uuuauguuau auacaaacuu    5280
uuugcuggca uucaggguccc auacacagga aucccccaauc cuaaaccuaa aguacccucu   5340
cucagaacag cuaaagugca aggaccaggg uucgauuuug cacaagccau aaugaagaaa   5400
aauaccguca uugcaaggac ugaaaagggu gaguucacca ugcugggugu auaugauagg   5460
guagcgguca uccccacaca cgcaucuguu ggagaaacca uuuacauuaa ugauguagag   5520
acuaaaguuu uagaugcgug ugcacuuaga gacuugacug auacaaacuu agagauaacc   5580
auagucaaau uagaccguaa ucaaaaauuu agagauauca gacauuuucu gcccagauau   5640
gaggaugauu acaaugacgc ugugcuuagc guacauacau caaaauuccc aaauauguau   5700
aucccaguug gacaagucac caauuauggc uucuugaacc uaggugguac accgacgcac   5760
cgcauuuuaa uguauaacuu cccaacaaga gcuggccagu gugguggugu ggugacaacu   5820
acagguaagg ugauaggaau acauguaggu ggaaauggag cucaaggauu ugcagcaaug   5880
cuacuacacu cuuacuuuuc cgauacacaa ggugagauag uuaguaguga aaagaguggg   5940
gugugcauua acgcaccggc aaagacuaaa cuccaaccua guguuuucca ucaaguuuuu   6000
gaagguucaa aggaaccagc aguucucaau ccaaaagauc cuaggcuuaa aacagauuuc   6060
gaggaggcca uuuucucaaa guacacaggu aacaaaauua uguuaaugga ugaguacaug   6120
gaagaggcag uggaucauua ugugggggugu uuagaaccau uagacaucag uguggauccc   6180
auaccccugg aaagugccau guauggaaug gauggccuug aggcauuaga cuuaacuacc   6240
agugcaggau ucccuuacuu acuacaaggg aagaagaaaa gggauauauu uaauagacau   6300
acuagagaca ccagugaaau gacaaaaaug uuagagaaau auggaguuga ccuaccuuuu   6360
guaaccuuug uaaaagauga gcuuagauca agagaaaaag uugaaaaagg gaaaucacgc   6420
cugauugagg ccaguuccuu gaaugacuca guugcuauga gaguugccuu uggaaaccuu   6480
uacgccacau uucacaacaa uccagguaca gcaacuggua gugcaguugg uugugaucca   6540
gauauauuuu ggucaaaaau cccuauuuug uuagauggag aaaucuuugc uuuugacuac   6600
acugguuaug augcuaguuu gucaccagug ugguuugccu gcuuaaagaa aguucuaauu   6660
aaguuagguu acacacauca aacgucuuuu auagauuauu ugugucauuc aguacauuua   6720
```

```
uauaaggaca aaaaauacau aguuaauggu ggaaugcccu cugguucuuc aggcaccagc   6780

auauucaaca cuaugaucaa caauauaauc auaagaacuu uauuaauuag gguuuacaaa   6840

ggcauagacc uggaccaguu caaaaugauu gccuaugggg augauguuau ugcuagcuac   6900

ccacauaaga uugauccagg uuugcuggca gaagcaggua aacaguaugg auuaguaaug   6960

acgccagcag acaaaggaac caguuuuauu gacacaaauu gggaaaaugu aacuuucuua   7020

aaaagauauu ucagagcaga ugaucaauac cccuuucuca uacauccagu gaugccaaug   7080

aaagagauac augaaucuau uagauggacu aaagauccca gaaacacaca ggaucauguu   7140

aggucuuugu gcuaccucgc auggcauaau ggagaggagg cuuauaauga auuuugcaga   7200

aaaaucagaa gugugccugu gggaagagca uugacacuac cugcauacuc uagucuuaga   7260

cggaaauggu uagauucguu cuagacaacu cuaauugaaa cccaaguuau aguuacuuuc   7320

auuuagaggu aaauuuuggu cacuuggggg ccaaaaaaaa aaaaaaaaaa aaaaaaaguc   7380

gac                                                                 7383
```

<210> SEQ ID NO 13
<211> LENGTH: 7306
<212> TYPE: RNA
<213> ORGANISM: Artificial Sequence
<220> FEATURE:
<223> OTHER INFORMATION: Genomic sequence of EV-D68-HRV2

<400> SEQUENCE: 13

```
uaauacgacu cacuauaggu uaaaacagcc uuggggguugu ucccacucca agggcccacg     60

uggcggcuag uacucuggua cuucgguacc uuuguacgcc uguuuuaucu cccuucccaa    120

uguaacuuag aagaacuuag aaguuuuuca caaagaccaa uagccgguaa ucagccagau    180

uacugaaggu caagcacuuc uguuuccccg gucaauguug auaugcucca acagggcaaa    240

aacaacugcg aucguuaacc gcaaagcgcc uacgcaaagc uuaguagcau cuuugaaauc    300

guuuggcugg ucgauccgcc auuuccccug guagaccugg cagaugaggc uagaaauacc    360

ccacuggcga caguguucua gccugcgugg cugccugcac acccuauggg ugugaagcca    420

aacaauggac aaggugugaa gagccccgug ugcucgcuuu gaguccuccg gccccugaau    480

guggcuaacc uuaacccugc agcuagagca cguaacccaa uguguaucua gucguaauga    540

gcaauugcgg gaugggacca acuacuuugg guguccgugu uucacuuuuu ccuuuauauu    600

ugcuuauggu gacaauauau acaauauaua uauuggcacc augggagcuc agguuacuag    660

acaacaaacu ggcacucaug aaaaugccaa cauugccaca aauggaucuc auaucacaua    720

caaucagaua aacuuuuaca aggauagcua ugcggcuuca gccagcaagc aggauuuuuc    780

acaggaccca ucaaaauuca cugaaccagu aguggaaggu uuaaaagcag gggcgccagu    840

uuugaaaucu ccuagugcug aggcaugugg cuacagugau agaguauuac agcucaaauu    900

aggaaauuca gcuauuguca cccaggaagc agcgaacuac ugcugcgcuu augguggaaug    960

gcccaauuac uuaccagacc augaagcagu agccauugau aaaccuacac aaccagaaac   1020

ugcuacagau agauucuaca cuuugaaauc agucaaaugg gaaacuggaa gcacaggaug   1080

gugguggaaa cuacccgaug cacugaauaa uauaggcaug uuuggacaga augugcagca   1140

ucacuaccua uauagaucug guuucuugau ucaugugcag uguaaugcca caaaauucca   1200

ucaaggugcc uuauuagugg uagcaauucc agaacaucag aggggagcgc acaacaccaa   1260

cacuagccca ggguuugaug auauaaugaa aggugaagaa ggagggaccu ucaaucaucc   1320
```

-continued

```
auauguccuu gaugauggaa caucauuggc uugugcgacg auauuuccac aucaguggau   1380

aaaucugaga accaacaauu cagcaacaau uguucuuccc uggaugaaug cugcuccaau   1440

ggauuuccca cuuagacaua aucaguggac gcuagcaaua auaccagugg ugccauuagg   1500

uacgcguaca acaucaagua uggucccaau aacaguuuca aucgcuccaa uguguuguga   1560

guuuaaugga cuuagacacg ccauuacuca aggugoccca acauaccuuu uaccaggcuc   1620

gggacaauuc cuaacaacug augaucauag cucugcacca gcucucccgu guuucaaccc   1680

aacuccagaa augcauaucc cagggcaggu ccguaacaug cuagaagugg uccaagugga   1740

aucaaugaug gagauuaaua acacagaaag ugcaguuggc auggagcguc uuaagguuga   1800

uauaucagca uugacagaug ucgaucaauu guuauucaac auuccacugg acauacaguu   1860

ggaugggcca cuuagaaaca cuuugguagg aaacauaucu agauauuaca cucauugguc   1920

uggaucccua gaaaugacgu uuauguuuug uggcagcuuc auggcaacgg gaaaauuaau   1980

ccugugcuau acuccuccag guggaucaug cccgacaacc agagagaccg ccauguuagg   2040

uacacauauu guuugggauu uuggauuaca aucuagugua acccugauaa uaccuuggau   2100

uaguggaucc cacuacagga uguuuaauaa ugaugcuaag ucaacuaaug ccaacguugg   2160

cuaugucacu uguuuuaugc agaccaaucu gauagucccc agugaauccu cugacacgug   2220

uuccuugaua ggguucauag cagcaaaaga ugauuucucc cucagauuaa ugagagacag   2280

cccugacauu ggacaacuag accauuuaca ugcagcagag gcagccuacc agaucgagag   2340

caucaucaaa acagcgaccg acacugugaa aagugagauu aaugcugaac uugguguggu   2400

cccuagcuua aaugcaguug aaacaggugc aacuucuaac acugaaccag aagaagccau   2460

acaaacucgc acagugauaa aucagcacgg uguauccgag acucuagugg agaauuuucu   2520

caguagagca gcuuugguau caaagagaag uuuugaauac aaagaucaua cuucgucugc   2580

agcacaagca gacaagaacu uuuucaaaug gacaauuaac accagauccu uuguacaguu   2640

aagaagaaaa uuagaauuau ucacauaccu uagauuugau gcugagauca cuauacucac   2700

aacuguagca gugaauggua gugguaauaa uacauacgug ggucuuccug acuugacacu   2760

ccaagcaaug uuuguaccca cuggugcucu uaccccagaa aaacaggacu cauuccacug   2820

gcagucaggc aguaaugcua guguauucuu uaaaaucucc gacccccag ccagaauaac   2880

cauaccuuuu augugcauua acucagcaua cucaguuuuu uaugauggcu uugccggauu   2940

ugagaaaaac ggucuguaug gaauaaaucc agcugacacu auugguaacu uauguguuag   3000

aauagugaau gaacaccaac caguugguuu cacagugacc guuaggguuu acaugaagcc   3060

uaaacacaua aaagcauggg caccacgacc accacgaacu uugccauaua ugaguauugc   3120

aaaugcaaau uacaaaggua aagaaagagc accaaaugcg cucaaugcua uaauuggcaa   3180

uagagacagu gucaaaacca ugccucauaa uauagugaac acugguccag gcuucggagg   3240

aguuuuugua gggucuuuca aaauaaucaa cuaucacuug gccacuacag aagagagaca   3300

gucagcuauc uauguggauu ggcaaucaga cgucuugguu acccccauug cugcucaugg   3360

aaggcaccaa auagcaagau gcaagugcaa cacagggguu uacuauugua ggcacaaaaa   3420

cagaaguuac ccgauuugcu uugaaggccc agggauucaa uggauugaac aaaaugaaua   3480

uuacccagca agguaccaga ccaauguacu auuggcaguu gguccugcgg aagcaggaga   3540

uugcggugu uuacuaguuu guccacaugg gguaaucggu cuucuuacag caggaggggg   3600

uggaauugua gcuuucacug auaucaggaa uuugcuaugg uuagauacug augcuaugga   3660

acaaggcauu acugauuaua uucaaaaucu ugguaaugcc uuuggagcag gauuuacaga   3720
```

```
aacaaucucu aauaaagcca aggaagugca agauaugcua auuggagaga guucacuauu   3780
agaaaaauug uuaaaagcuc uaaucaaaau cauaucagca uuaguaauug uaaucagaaa   3840
cucagaagau uuagucacag ucacagccac acuagcauug uugggaugcc augauucacc   3900
auggagcuac uugaaacaga agguauguuc auacuuaggu auuccuuaug uaccuagaca   3960
gggugaaucg uggcuuaaga aauucacaga ggcaugcaau gcucuuagag gucuggauug   4020
gcuaucgcaa aagauagaua aauucaucaa cuggcuuaaa accaaaauau uaccagaagc   4080
uagggagaaa uaugaauuug ugcaaaggcu caaacaguua ccggugauag aaaaccaagu   4140
uaguacaauc gagcauagcu gcccaacaac agaacaacaa caggccuuau ucaacaacgu   4200
ccaauacuau ucacacuacu guagaaagua cgcaccacuu uacgcagugg aagcaaagag   4260
gguaguagcu cuugaaaaga aaauaaacaa cuacauccag uucaagucca aaucucgcau   4320
ugaaccgguu uguuuaauaa uacauggcuc uccaggaacu ggcaagucag uggcuucaaa   4380
uuuaauugcc agggcuauca cagagaaauu ggggggggac auuuauuccu ugccuccaga   4440
cccuaaauau uuugauggau acaaacagca aacagugguc cucauggaug auuuaaugca   4500
aaauccagau gggaaugaca uaucuauguu cugccaaaug gucuccacug uagauuucau   4560
acccccaaug gcuaguuugg aggaaaaagg aacucuauac accaguccau uuuuaauagc   4620
uacuaccaau gcuggcucaa uacaugcacc aacuguauca gacucaaagg cuuugucacg   4680
cagauuuaaa uuugacgugg acauugaagu cacagauuca uacaaggacu caaauaaauu   4740
ggauauguca agggcagucg agaugugcaa accagauggc ugugcccccca ccaauuacaa   4800
aagaugcugc ccauugaucu guggaaaggc uauccaauuc agagaucgca gaacuaaugc   4860
aagauccacu auugauaugc uaguaacuga uauuauaaag gaauauagaa ccagaaacag   4920
uacacaggau aagcuggaag cucuguuuca ggggccucca caguuuaaag agaucaaaau   4980
uucagucacc ccagauacac cagcuccuga ugcuauaaau gaccuucuua ggucagugga   5040
uucucaagaa guuagggauu auugccaaaa gaaaggaugg auuguaguac acccaucaaa   5100
ugagcuaaua guagaaaaac acauuaguag agcuuuuauu acucuacaag ccauugccac   5160
cuuuguauca auagcuggug uaguuuaugu uauauacaaa cuuuuugcug gcauucaggg   5220
uccauacaca ggaaucccca auccuaaacc uaaaguaccc ucucucagaa cagcuaaagu   5280
gcaaggacca ggguucgauu uugcacaagc cauaaugaag aaaaauaccg ucauugcaag   5340
gacugaaaag ggugaguuca ccaugcuggg uguauaugau aggguagcgg ucauccccac   5400
acacgcaucu guuggagaaa ccauuuacau uaaugaugua gagacuaaag uuuuagaugc   5460
gugugcacuu agagacuuga cugauacaaa cuuagagaua accauaguca aauuagaccg   5520
uaaucaaaaa uuuagagaua ucagacauuu ucugcccaga uaugaggaug auuacaauga   5580
cgcugugcuu agcguacaua caucaaaauu cccaaauaug uauaucccag uuggacaagu   5640
caccaauuau ggcuucuuga accuaggugg uacaccgacg caccgcauuu uaauguauaa   5700
cuucccaaca agagcuggcc aguguggugg uguggugaca acuacaggua aggugauagg   5760
aauacaugua gguggaaaug gagcucaagg auuugcagca augcuacuac acucuuacuu   5820
uuccgauaca caaggugaga uaguuaguag ugaaaagagu ggggugugca uuaacgcacc   5880
ggcaaagacu aaacuccaac cuaguguuuu ccaucaaguu uuugaagguu caaaggaacc   5940
agcaguucuc aauccaaaag auccuaggcu uaaaacagau uucgaggagg ccauuuucuc   6000
aaaguacaca gguaacaaaa uuauguuaau ggaugaguac auggaagagg caguggauca   6060
```

```
uuaugugggg uguuuagaac cauuagacau caguguggau cccauacccc uggaaagugc   6120

cauguaugga auggauggcc uugaggcauu agacuuaacu accagugcag gauucccuua   6180

cuuacuacaa gggaagaaga aaagggauau auuuaauaga cauacuagag acaccaguga   6240

aaugacaaaa auguuagaga aauauggagu ugaccuaccu uuuguaaccu uuguaaaaga   6300

ugagcuuaga ucaagagaaa aaguugaaaa agggaaauca cgccugauug aggccaguuc   6360

cuugaaugac ucaguugcua ugagaguugc cuuuggaaac cuuuacgcca cauuucacaa   6420

caauccaggu acagcaacug guagugcagu ugguugugau ccagauauau uuuggucaaa   6480

aaucccuauu uuguuagaug gagaaaucuu ugcuuuugac uacacugguu augaugcuag   6540

uuugucacca guguggguuug ccugcuuaaa gaaaguucua auuaaguuag guuacacaca   6600

ucaaacgucu uuuauagauu auuuguguca uucaguacau uuauauaagg acaaaaaaua   6660

cauaguuaau gguggaaugc ccucugguuc uucaggcacc agcauauuca acacuaugau   6720

caacaauaua aucauaagaa cuuuauuaau uaggguuuac aaaggcauag accuggacca   6780

guucaaaaug auugccuaug ggaugaugu uauugcuagc uacccacaua agauugaucc   6840

agguuugcug gcagaagcag guaaacagua uggauuagua augacgccag cagacaaagg   6900

aaccaguuuu auugacacaa auugggaaaa uguaacuuuc uuaaaaagau auuucagagc   6960

agaugaucaa uaccccuuuc ucauacaucc agugaugcca augaaagaga uacaugaauc   7020

uauuagaugg acuaaagauc ccagaaacac acaggaucau guuaggucuu ugugcuaccu   7080

cgcauggcau aauggagagg aggcuuauaa ugaauuuugc agaaaaauca gaagugugcc   7140

ugugggaaga gcauugacac uaccugcaua cucuagucuu agacggaaau gguuagauuc   7200

guucuagaca acucuaauug aaacccaagu uauaguuacu uucauuuaga gguaaauuuu   7260

ggucacuugg gggccaaaaa aaaaaaaaaa aaaaaaaaaa gucgac                  7306
```

<210> SEQ ID NO 14
<211> LENGTH: 7485
<212> TYPE: RNA
<213> ORGANISM: Artificial Sequence
<220> FEATURE:
<223> OTHER INFORMATION: Genomic sequence of EV-D68-miR133&206T

<400> SEQUENCE: 14

```
uaauacgacu cacuauaggu uaaaacagcc uuggggguugu ucccacucca agggcccacg     60

uggcggcuag uacucuggua cuucgguacc uuuguacgcc uguuuuaucu cccuucccaa    120

uguaacuuag aaguucuuaa aucaaugcuc aauaggguggg gcgcaaacca gcgcucucau    180

gagcaagcac uccugucucc ccggugaggu uguauaaacu guucccacgg uugaaaacaa    240

ccuauccguu auccgcuaua guacuucgag aaaccuagua ccaccuuugg auuguugacg    300

cguugcgcuc agcacacuaa cccgugugua gcuugggucg augagucugg acauaccuca    360

cuggcgacag ugguccaggc ugcguuggcg gccuacucau ggugaaagcc augagacgcu    420

agacaugaac aaggugugaa gagucuauug agcuacuaua gaguccuccg gccccugaau    480

gcggcuaauc cuaaccaugg agcaagugcu cacaggccag ugaguugcuu gucguaaugc    540

gcaaguccgu ggcggaaccg acuacuuugg guguccgugu uucacuuuuu acuuuuauga    600

cugcuuaugg ugacaauuug auauuguuac cauuuagcuu gucaaaucaa uugcaaaaga    660

uccuaaaucu uauuuaucaa cuugcaucuu gauaacuuua auuugaaaau uuuaacaaug    720

ggagcucagg uuacuagaca acaaacuggc acucaugaaa augccaacau ugccacaaau    780

ggaucucaua ucacauacaa ucagauaaac uuuuacaagg auagcuaugc ggcuucagcc    840
```

```
agcaagcagg auuuuucaca ggacccauca aaauucacug aaccaguagu ggaagguuua    900
aaagcagggg cgccaguuuu gaaaucuccu agugcugagg cauguggcua cagugauaga    960
guauuacagc ucaaauuagg aaauucagcu auugucaccc aggaagcagc gaacuacugc   1020
ugcgcuuaug gugaauggcc caauuacuua ccagaccaug aagcaguagc cauugauaaa   1080
ccuacacaac cagaaacugc uacagauaga uucuacacuu ugaaaucagu caaauuggaa   1140
acuggaagca caggauggug guggaaacua cccgaugcac ugaauaauau aggcauguuu   1200
ggacagaaug ugcagcauca cuaccuauau agaucugguu ucuugauuca ugugcagugu   1260
aaugccacaa aauuccauca aggugccuua uuagugguag caauuccaga acaucagagg   1320
ggagcgcaca acaccaacac uagcccaggg uuugaugaua uaaugaaagg ugaagaagga   1380
gggaccuuca aucauccaua uguccuugau gauggaacau cauuggcuug ugcgacgaua   1440
uuuccacauc aguggauaaa ucugagaacc aacaauucag caacaauugu ucuucccugg   1500
augaaugcug cuccaaugga uuucccacuu agacauaauc aguggacgcu agcaauaaua   1560
ccagugguge cauuagguac gcguacaaca ucaaguaugg ucccaauaac aguuucaauc   1620
gcuccaaugu guugugaguu uaauggacuu agacacgcca uuacucaagg ugucccaaca   1680
uaccuuuuac caggcucggg acaauuccua acaacugaug aucauagcuc ugcaccagcu   1740
cucccguguu ucaacccaac uccagaaaug cauaucccag ggcagguccg uaacaugcua   1800
gaaguggucc aaguggaauc aaugauggag auuaauaaca cagaaagugc aguuggcaug   1860
gagcgucuua agguugauau aucagcauug acagaugucg aucaauuguu auucaacauu   1920
ccacuggaca uacaguugga ugggccacuu agaaacacuu gguaggaaa cauaucuaga    1980
uauuacacuc auuggucugg aucccuagaa augacguuua uguuuugugg cagcuucaug   2040
gcaacgggaa aauuaauccu gugcuauacu ccuccaggug gaucaugccc gacaaccaga   2100
gagaccgcca uguuagguac acauauuguu ugggauuuug gauuacaauc uaguguaacc   2160
cugauaauac cuuggauuag uggaucccac uacaggaugu uuaauaauga ugcuaaguca   2220
acuaaugcca acguuggcua ugucacuugu uuuaugcaga ccaaucugau aguccccagu   2280
gaauccucug acacguguuc cuugauaggg uucauagcag caaaagauga uuucucccuc   2340
agauuaauga gagacagccc ugacauugga caacuagacc auuuacaugc agcagaggca   2400
gccuaccaga ucgagagcau caucaaaaca gcgaccgaca cugugaaaag ugagauuaau   2460
gcugaacuug guguggucce uagcuuaaau gcaguugaaa caggugcaac uucuaacacu   2520
gaaccagaag aagccauaca aacucgcaca gugauaaauc agcacggugu auccgagacu   2580
cuaguggaga auuuucucag uagagcagcu uugguaucaa agagaaguuu ugaauacaaa   2640
gaucauacuu cgucugcagc acaagcagac aagaacuuuu ucaaauggac aauuaacacc   2700
agauccuuug uacaguuaag aagaaaauua gaauuauuca cauaccuuag auuugaugcu   2760
gagaucacua uacucacaac uguagcagug aaugguagug guaauaauac auacguggu    2820
cuuccugacu ugacacucca agcaauguuu guacccacug gugcucuuac cccagaaaaa   2880
caggacucau uccacuggca gucaggcagu aaugcuagug uauucuuuaa aaucuccgac   2940
cccccagcca gaauaaccau accuuuuaug ugcauuaacu cagcauacuc aguuuuuuau   3000
gauggcuuug ccggauuuga gaaaaacggu cuguauggaa uaaauccagc ugacacuauu   3060
gguaacuuau guguuagaau agugaaugaa caccaaccag uugguuucac agugaccguu   3120
aggguuuaca ugaagccuaa acacauaaaa gcaugggcac cacgaccacc acgaacuuug   3180
```

-continued

```
ccauauauga guauugcaaa ugcaaauuac aaagguaaag aaagagcacc aaaugcgcuc   3240
aaugcuauaa uuggcaauag agacaguguc aaaaccaugc cucauaaauau agugaacacu   3300
gguccaggcu ucggaggagu uuuuguaggg ucuuucaaaa uaaucaacua ucacuuggcc   3360
acuacagaag agagacaguc agcuaucuau guggauuggc aaucagacgu cuugguuacc   3420
cccauugcug cucauggaag gcaccaaaua gcaagaugca agugcaacac aggggguuuac   3480
uauuguaggc acaaaaacag aaguuacccg auuugcuuug aaggcccagg gauucaaugg   3540
auugaacaaa augaauauua cccagcaagg uaccagacca auguacuauu ggcaguuggu   3600
ccugcggaag caggagauug cggugguuua cuaguuuguc cacaugggggu aaucggucuu   3660
cuuacagcag gaggggggugg aauuguagcu uucacugaua ucaggaauuu gcuaugguua   3720
gauacugaug cuauggaaca aggcauuacu gauuauauuc aaaaucuugg uaaugccuuu   3780
ggagcaggau uuacagaaac aaucucuaau aaagccaagg aagugcaaga uaugcuaauu   3840
ggagagaguu cacuauuaga aaaauuguua aaagcucuaa ucaaaaucau aucagcauua   3900
guaauuguaa ucagaaacuc agaagauuua gucacaguca cagccacacu agcauuguug   3960
ggaugccaug auucaccaug gagcuacuug aaacagaagg uauguucaua cuuagguauu   4020
ccuuauguac cuagacaggg ugaaucgugg cuuaagaaau ucacagaggc augcaaugcu   4080
cuuagagguc uggauuggcu aucgcaaaag auagauaaau ucaucaacug gcuuaaaacc   4140
aaaauauuac cagaagcuag ggagaaauau gaauuugugc aaaggcucaa acaguuaccg   4200
gugauagaaa accaaguuag uacaaucgag cauagcugcc caacaacaga acaacaacag   4260
gccuuauuca acaacgucca auacuauuca cacuacugua gaaaguacgc accacuuuac   4320
gcaguggaag caaagagggu aguagcucuu gaaaagaaaa uaaacaacua cauccaguuc   4380
aaguccaaau cucgcauuga accgguuugu uuaauaauac auggcucucc aggaacuggc   4440
aagucagugg cuucaaauuu aauugccagg gcuaucacag agaaauuggg gggggacauu   4500
uauuccuugc cuccagaccc uaaauauuuu gauggauaca aacagcaaac aguggguccuc   4560
auggaugauu uaaugcaaaa uccagauggg aaugacauau cuauguucug ccaaaugguc   4620
uccacuguag auuucauacc cccaauggcu aguuuggagg aaaaaggaac ucuauacacc   4680
aguccauuuu uaauagcuac uaccaaugcu ggcucaauac augcaccaac uguaucagac   4740
ucaaaggcuu ugucacgcag auuuaaauuu gacguggaca uugaagucac agauucauac   4800
aaggacucaa auaaaauugga uaugucaagg gcagucgaga ugugcaaacc agauggcugu   4860
gcccccacca auuacaaaag augcugccca uugaucugug gaaaggcuau ccaauucaga   4920
gaucgcagaa cuaaugcaag auccacuauu gauaugcuag uaacugauau uauaaaggaa   4980
uauagaacca gaaacaguac acaggauaag cuggaagcuc uguuucaggg gccuccacag   5040
uuuaaagaga ucaaaauuuc agucacccca gauacaccag cuccugaugc uauaaaugac   5100
cuucuuaggu caguggauuc ucaagaaguu agggauuauu gccaaaagaa aggauggauu   5160
guaguacacc caucaaauga gcuaauagua gaaaaacaca uuaguagagc uuuuauuacu   5220
cuacaagcca uugccaccuu uguaucaaua gcuggugguag uuuauguuau auacaaacuu   5280
uuugcuggca uucagggucc auacacagga aucccccaauc cuaaaccuaa aguacccucu   5340
cucagaacag cuaaagugca aggaccaggg uucgauuuug cacaagccau aaugaagaaa   5400
aauaccguca uugcaaggac ugaaaagggu gaguucacca ugcugggugu auaugauagg   5460
guagcgguca uccccacaca cgcaucuguu ggagaaacca uuuacauuaa ugauguagag   5520
acuaaaguuu uagaugcgug ugcacuuaga gacuugacug auacaaacuu agagauaacc   5580
```

```
auagucaaau uagaccguaa ucaaaaauuu agagauauca gacauuuucu gcccagauau   5640
gaggaugauu acaaugacgc ugugcuuagc guacauacau caaaauuccc aaauauguau   5700
aucccaguug gacaagucac caauuauggc uucuugaacc uaggugguac accgacgcac   5760
cgcauuuuaa uguauaacuu cccaacaaga gcuggccagu gugguggugu ggugacaacu   5820
acagguaagg ugauaggaau acauguaggu ggaaauggag cucaaggauu ugcagcaaug   5880
cuacuacacu cuuacuuuuc cgauacacaa ggugagauag uuaguaguga aaagaguggg   5940
gugugcauua acgcaccggc aaagacuaaa cuccaaccua guguuuucca ucaaguuuuu   6000
gaagguucaa aggaaccagc aguucucaau ccaaaagauc cuaggcuuaa aacagauuuc   6060
gaggaggcca uuuucucaaa guacacaggu aacaaaauua uguuaaugga ugaguacaug   6120
gaagaggcag uggaucauua ugugggggugu uuagaaccau uagacaucag uguggauccc   6180
auaccccugg aaagugccau guauggaaug gauggccuug aggcauuaga cuuaacuacc   6240
agugcaggau ucccuuacuu acuacaaggg aagaagaaaa gggauauauu uaauagacau   6300
acuagagaca ccagugaaau gacaaaaaug uuagagaaau auggaguuga ccuaccuuuu   6360
guaaccuuug uaaaagauga gcuuagauca agagaaaaag uugaaaaagg gaaaucacgc   6420
cugauugagg ccaguuccuu gaaugacuca guugcuauga gaguugccuu uggaaaccuu   6480
uacgccacau uucacaacaa uccagguaca gcaacuggua gugcaguugg uugugaucca   6540
gauauauuuu ggucaaaaau cccuauuuug uuagauggag aaaucuuugc uuuugacuac   6600
acugguuaug augcuaguuu gucaccagug ugguuugccu gcuuaaagaa aguucuaauu   6660
aaguuagguu acacacauca aacgucuuuu auagauuauu ugugucauuc aguacauuua   6720
uauaaggaca aaaaauacau aguuaauggu ggaaugcccu cugguucuuc aggcaccagc   6780
auauucaaca cuaugaucaa caauauaauc auaagaacuu uauuaauuag gguuuacaaa   6840
ggcauagacc uggaccaguu caaaaugauu gccuaugggg augauguuau ugcuagcuac   6900
ccacauaaga uugauccagg uuugcuggca gaagcaggua aacaguaugg auuaguaaug   6960
acgccagcag acaaaggaac caguuuuauu gacacaaauu gggaaaaugu aacuuucuua   7020
aaaagauauu ucagagcaga ugaucaauac cccuuucuca uacauccagu gaugccaaug   7080
aaagagauac augaaucuau uagauggacu aaagaucccca gaaacacaca ggaucauguu   7140
aggucuuugu gcuaccucgc auggcauaau ggagaggagg cuuauaauga auuuugcaga   7200
aaaaucagaa gugugccugu gggaagagca uugacacuac cugcauacuc uagucuuaga   7260
cggaaauggu uagauucguu cuagacaacu cuaacagcug guugaagggg accaacgaua   7320
cagcugguug aaggggacca aaccggucca cacacuuccu uacauuccau cacccacaca   7380
cuuccuuaca uuccaauuga aacccaaguu auaguuacuu ucauuuagag guaaauuuug   7440
gucacuuggg ggccaaaaaa aaaaaaaaaa aaaaaaaaag ucgac                   7485
```

<210> SEQ ID NO 15
<211> LENGTH: 7860
<212> TYPE: RNA
<213> ORGANISM: Artificial Sequence
<220> FEATURE:
<223> OTHER INFORMATION: Genomic sequence of EV-D68-GM-CSF

<400> SEQUENCE: 15

```
uaauacgacu cacuauaggu uaaaacagcc uugggguugu ucccacucca agggcccacg     60
uggcggcuag uacucuggua cuucgguacc uuuguacgcc uguuuuaucu cccuucccaa    120
```

-continued

```
uguaacuuag aaguucuuaa aucaaugcuc aauaggu ggg gcgcaaacca gcgcucucau    180
gagcaagcac uccugucucc ccggugaggu uguauaaacu guucccacgg uugaaaacaa    240
ccuauccguu auccgcuaua guacuucgag aaaccuagua ccaccuuugg auuguugacg    300
cguugcgcuc agcacacuaa cccgugugua gcuugggucg augagucugg acauaccuca    360
cuggcgacag ugguccaggc ugcguuggcg gccuacucau ggugaaagcc augagacgcu    420
agacaugaac aaggugugaa gagucuauug agcuacuaua gaguccuccg gccccugaau    480
gcggcuaauc cuaaccaugg agcaagugcu cacaggccag ugaguugcuu gucguaaugc    540
gcaaguccgu ggcggaaccg acuacuuugg guguccgugu uucacuuuuu acuuuuauga    600
cugcuuaugg ugacaauuug auauuguuac cauuuagcuu gucaaaucaa uugcaaaaga    660
uccuaaaucu uauuuaucaa cuugcaucuu gauaacuuua auuugaaaau uuuaacaaug    720
ggagcucagg uuacuagaca acaaacuggc acucaugaaa augccaacau ugccacaaau    780
ggaucucaua ucacauacaa ucagauaaac uuuuacaagg auagcuaugc ggcuucagcc    840
agcaagcagg auuuuucaca ggacccauca aaauucacug aaccaguagu ggaagguuua    900
aaagcagggg cgccaguuuu gaaaucuccu agugcugagg cauguggcua cagugauaga    960
guauuacagc ucaaauuagg aaauucagcu auugucaccc aggaagcagc gaacuacugc   1020
ugcgcuuaug gugaauggcc caauuacuua ccagaccaug aagcaguagc cauugauaaa   1080
ccuacacaac cagaaacugc uacagauaga uucuacacuu ugaaaucagu caaaugggaa   1140
acuggaagca caggauggug guggaaacua cccgaugcac ugaauaaaau aggcauguuu   1200
ggacagaaug ugcagcauca cuaccuauau agaucugguu ucuugauuca ugugcagugu   1260
aaugccacaa aauuccauca aggugccuua uuaguggua g caauuccaga acaucagagg   1320
ggagcgcaca acaccaacac uagcccaggg uuugaugaua uaaugaaagg ugaagaagga   1380
gggaccuuca aucauccaua uguccuugau gauggaacau cauuggcuug ugcgacgaua   1440
uuuccacauc aguggauaaa ucugagaacc aacaauucag caacaauugu ucuucccugg   1500
augaaugcug cuccaaugga uuucccacuu agacauaauc aguggacgcu agcaauaaua   1560
ccagugguge cauuagguac gcguacaaca ucaaguaugg ucccaauaac aguuucaauc   1620
gcuccaaugu guugugaguu uaauggacuu agacacgcca uuacucaagg ugucccaaca   1680
uaccuuuuac caggcucggg acaauuccua acaacugaug aucauagcuc ugcaccagcu   1740
cucccguguu ucaacccaac uccagaaaug cauaucccag ggcagguccg uaacaugcua   1800
gaagugguce aaguggaauc aaugauggag auuaauaaca cagaaagugc aguuggcaug   1860
gagcgucuua agguugauau aucagcauug acagaugucg aucaauuguu auucaacauu   1920
ccacuggaca uacaguugga ugggccacuu agaaacacuu ugguaggaaa cauaucuaga   1980
uauuacacuc auuggucugg aucccuagaa augacguuua uguuuugugg cagcuucaug   2040
gcaacgggaa aauuaauccu gugcuauacu ccuccaggug gaucaugccc gacaaccaga   2100
gagaccgcca uguuagguac acauauuguu ugggauuuug gauuacaauc uaguguaacc   2160
cugauaauac cuuggauuag uggaucccac uacaggaugu uuaauaauga ugcuaaguca   2220
acuaaugcca acguuggcua ugucacuugu uuuaugcaga ccaaucugau aguccccagu   2280
gaauccucug acacguguuc cuugauaggg uucauagcag caaaagauga uuucuccuc   2340
agauuaauga gagacagccc ugacauugga caacuagacc auuuacaugc agcagaggca   2400
gccuaccaga ucgagagcau caucaaaaca gcgaccgaca cugugaaaag ugagauuaau   2460
gcugaacuug gugugguccc uagcuuaaau gcaguugaaa caggugcaac uucuaacacu   2520
```

-continued

```
gaaccagaag aagccauaca aacucgcaca gugauaaauc agcacggugu auccgagacu   2580
cuaguggaga auuuucucag uagagcagcu uugguaucaa agagaaguuu ugaauacaaa   2640
gaucauacuu cgucugcagc acaagcagac aagaacuuuu ucaaauggac aauuaacacc   2700
agauccuuug uacaguuaag aagaaaauua gaauuauuca cauaccuuag auuugaugcu   2760
gagaucacua uacucacaac uguagcagug aaugguagug guaauaaauac auacgugggu  2820
cuuccugacu ugacacucca agcaauguuu guacccacug gugcucuuac cccagaaaaa   2880
caggacucau uccacuggca gucaggcagu aaugcuagug uauucuuuaa aaucuccgac   2940
cccccagcca gaauaaccau accuuuuaug ugcauuaacu cagcauacuc aguuuuuuau   3000
gauggcuuug ccggauuuga gaaaaacggu cuguauggaa uaaauccagc ugacacuauu   3060
gguaacuuau guguuagaau agugaaugaa caccaaccag uugguuucac agugaccguu   3120
aggguuuaca ugaagccuaa acacauaaaa gcaugggcac cacgaccacc acgaacuuug   3180
ccauauauga guauugcaaa ugcaaauuac aaagguaaag aaagagcacc aaaugcgcuc   3240
aaugcuauaa uuggcaauag agacaguguc aaaaccaugc cucauaauau agugaacacu   3300
gguccaggcu ucuggcugca gagccugcug cucuugggca cuguggccug cagcaucucu   3360
gcacccgccc gcucgcccag ccccagcacg cagcccuggg agcaugugaa ugccauccag   3420
gaggcccggc gucuccugaa ccugaguaga gacacugcug cugagaugaa ugaaacagua   3480
gaagucaucu cagaaauguu ugaccuccag gagccgaccu gccuacagac ccgccuggag   3540
cuguacaagc agggccugcg gggcagccuc accaagcuca agggccccuu gaccaugaug   3600
gccagccacu acaagcagca cugcccucca accccggaaa cuuccugugc aacccagauu   3660
aucaccuuug aaaguuucaa agagaaccug aaggacuuuc ugcuugucau ccccuuugac   3720
ugcugggagc caguccagga gagugucaaa accaugccuc auaauauagu gaacacuggu   3780
ccaggcuucg gaggaguuuu uguagggucu uucaaaauaa ucaacuauca cuuggccacu   3840
acagaagaga gacagucagc uaucuaugug gauuggcaau cagacgucuu gguuaccccc   3900
auugcugcuc auggaaggca ccaaauagca agaugcaagu gcaacacagg gguuuacuau   3960
uguaggcaca aaaacagaag uuacccgauu ugcuuugaag gcccagggau ucaauggauu   4020
gaacaaaaug aauauuaccc agcaagguac cagaccaaug uacuauuggc aguuggcccu   4080
gcggaagcag gagauugcgg ugguuuacua guuuguccac auggggguaau cggucuucuu  4140
acagcaggag gggguggaau uguagcuuuc acugauauca ggaauuugcu augguuagau   4200
acugaugcua uggaacaagg cauuacugau uauauucaaa aucuugguaa ugccuuugga   4260
gcaggauuua cagaaacaau cucuaauaaa gccaaggaag ugcaagauau gcuaauugga   4320
gagaguucac uauuagaaaa auuguuaaaa gcucuaauca aaaucauauc agcauuagua   4380
auuguaauca gaaacucaga agauuuaguc acagucacag ccacacuagc auuguuggga   4440
ugccaugauu caccauggag cuacuugaaa cagaagguau guucauacuu agguauuccu   4500
uauguaccua gacaggguga aucguggcuu aagaaauuca cagaggcaug caaugcucuu   4560
agaggucugg auuggcuauc gcaaaagaua gauaaauuca ucaacuggcu uaaaaccaaa   4620
auauuaccag aagcuaggga gaaauaugaa uuugugcaaa ggcucaaaca guuaccggug   4680
auagaaaacc aaguuaguac aaucgagcau agcugcccaa caacagaaca acaacaggcc   4740
uuauucaaca acguccaaua cuauucacac uacuguagaa aguacgcacc acuuuacgca   4800
guggaagcaa agaggguagu agcucuugaa aagaaaauaa acaacuacau ccaguucaag   4860
```

-continued

```
uccaaaucuc gcauugaacc gguuuguuua auaauacaug gcucuccagg aacuggcaag   4920
ucaguggcuu caaauuuaau ugccagggcu aucacagaga aauugggggg ggacauuuau   4980
uccuugccuc cagacccuaa auauuuugau ggauacaaac agcaaacagu gguccucaug   5040
gaugauuuaa ugcaaaaucc agaugggaau gacauaucua uguucugcca aauggucucc   5100
acuguagauu ucauacccc aauggcuagu uuggaggaaa aggaacucu auacaccagu   5160
ccauuuuuaa uagcuacuac caaugcuggc ucaauacaug caccaacugu aucagacuca   5220
aaggcuuugu cacgcagauu uaaauuugac guggacauug aagucacaga uucauacaag   5280
gacucaaaua aauuggauau gucaagggca gucgagaugu gcaaaccaga uggcugugcc   5340
cccaccaauu acaaaagaug cugcccauug aucuguggaa aggcuaucca auucagagau   5400
cgcagaacua augcaagauc cacuauugau augcuaguaa cugauauuau aaaggaauau   5460
agaaccagaa acaguacaca ggauaagcug gaagcucugu uucaggggcc uccacaguuu   5520
aaagagauca aaauuucagu caccccagau acaccagcuc cugaugcuau aaaugaccuu   5580
cuuaggucag uggauucuca agaaguuagg gauuauugcc aaaagaaagg auggauugua   5640
guacacccau caaaugagcu aauaguagaa aaacacauua guagagcuuu uauuacucua   5700
caagccauug ccaccuuugu aucaauagcu gguguaguuu auguuauaua caaacuuuuu   5760
gcuggcauuc agggucauaa cacaggaauc cccaauccua aaccuaaagu acccucucuc   5820
agaacagcua aagugcaagg accaggguuc gauuuugcac aagccauaau gaagaaaaau   5880
accgucauug caaggacuga aaagggugag uucaccaugc ugggguguaua ugauagggua   5940
gcggucaucc ccacacacgc aucuguugga gaaaccauuu acauuaauga uguagagacu   6000
aaaguuuuag augcgugugc acuuagagac uugacugaua caaacuuaga gauaaccaua   6060
gucaaauuag accguaauca aaaauuuaga gauaucagac auuuucugcc cagauaugag   6120
gaugauuaca augacgcugu gcuuagcgua cauacaucaa aauucccaaa uauguauauc   6180
ccaguuggac aagucaccaa uuauggcuuc uugaaccuag gugguacacc gacgcaccgc   6240
auuuuaaugu auaacuuccc aacaagagcu ggccagugug guggugugguu gacaacuaca   6300
gguaaaggga uaggaauaca uguaggugga aauggagcuc aaggauuugc agcaaugcua   6360
cuacacucuu acuuuuccga uacacaaggu gagauaguua guagugaaaa gagugggggug   6420
ugcauuaacg caccggcaaa gacuaaacuc caaccuagug uuuuccauca aguuuuugaa   6480
gguucaaagg aaccagcagu ucucaaucca aaagauccua ggcuuaaaac agauuucgag   6540
gaggccauuu ucucaaagua cacagguaac aaaauuaugu uaauggauga guacauggaa   6600
gaggcagugg aucauuaugu gggguguuua gaaccauuag acaucagugu ggaucccaua   6660
ccccuggaaa gugccaugua uggaauggau ggccuugagg cauuagacuu aacuaccagu   6720
gcaggauucc cuuacuuacu acaagggaag aagaaaaggg auauauuuaa uagacauacu   6780
agagacacca gugaaaugac aaaaauguua gagaaauaug gaguugaccu accuuuugua   6840
accuuuguaa aagaugagcu uagaucaaga gaaaaaguug aaaaagggaa aucacgccug   6900
auugaggcca guuccuugaa ugacucaguu gcuaugagag uugccuuugg aaaccuuuac   6960
gccacauuuc acaacaaucc agguacagca acugguagug caguugguug ugauccagau   7020
auauuuuggu caaaaauccc uauuuuguua gauggagaaa ucuuugcuuu ugacuacacu   7080
gguuaugaug cuaguuuguc accagugugg uuugccugcu uaaagaaagu ucuaauuaag   7140
uuagguuaca cacaucaaac gucuuuuaua gauuauuugu gucauucagu acauuuauau   7200
aaggacaaaa aauacauagu uaauggugga augcccucug guucuucagg caccagcaua   7260
```

```
uucaacacua ugaucaacaa uauaaucaua agaacuuuau uaauuagggu uuacaaaggc   7320

auagaccugg accaguucaa aaugauugcc uaugggggaug auguuauugc uagcuaccca   7380

cauaagauug auccagguuu gcuggcagaa gcagguaaac aguauggauu aguaaugacg   7440

ccagcagaca aaggaaccag uuuuauugac acaaauuggg aaaauguaac uuucuuaaaa   7500

agauauuuca gagcagauga ucaauacccc uuucucauac auccagugau gccaaugaaa   7560

gagauacaug aaucuauuag auggacuaaa gaucccagaa acacacagga ucauguuagg   7620

ucuuugugcu accucgcaug gcauaaugga gaggaggcuu auaaugaauu uugcagaaaa   7680

aucagaagug ugccuguggg aagagcauug acacuaccug cauacucuag ucuuagacgg   7740

aaaugguuag auucguucua gacaacucua auugaaaccc aaguuauagu uacuuucauu   7800

uagagguaaa uuuuggucac uuggggggcca aaaaaaaaaa aaaaaaaaaa aaaagucgac   7860
```

<210> SEQ ID NO 16
<211> LENGTH: 8226
<212> TYPE: RNA
<213> ORGANISM: Artificial Sequence
<220> FEATURE:
<223> OTHER INFORMATION: Genomic sequence of EV-D68-Anti-PD1

<400> SEQUENCE: 16

```
uaauacgacu cacuauaggu uaaaacagcc uuggggguugu ucccacucca agggcccacg     60

uggcggcuag uacucuggua cuucgguacc uuuguacgcc uguuuuaucu cccuucccaa    120

uguaacuuag aaguucuuaa aucaaugcuc aauagguggg gcgcaaacca gcgcucucau    180

gagcaagcac uccugucucc ccggugaggu uguauaaacu guucccacgg uugaaaacaa    240

ccuauccguu auccgcuaua guacuucgag aaaccuagua ccaccuuugg auuguugacg    300

cguugcgcuc agcacacuaa cccgugugua gcuugggucg augagucugg acauaccuca    360

cuggcgacag ugguccaggc ugcguuggcg gccuacucau ggugaaagcc augagacgcu    420

agacaugaac aaggugugaa gagucuauug agcuacuaua gaguccuccg gccccugaau    480

gcggcuaauc cuaaccaugg agcaagugcu cacaggccag ugaguugcuu gucguaaugc    540

gcaaguccgu ggcggaaccg acuacuuugg guguccgugu uucacuuuuu acuuuuauga    600

cugcuuaugg ugacaauuug auauuguuac cauuuagcuu gucaaaucaa uugcaaaaga    660

uccuaaaucu uauuuaucaa cuugcaucuu gauaacuuua auuugaaaau uuuaacaaug    720

ggagcucagg uuacuagaca acaaacuggc acucaugaaa augccaacau ugccacaaau    780

ggaucucaua ucacauacaa ucagauaaac uuuuacaagg auagcuaugc ggcuucagcc    840

agcaagcagg auuuuucaca ggacccauca aaauucacug aaccaguagu ggaagguuua    900

aaagcagggg cgccaguuuu gaaaucuccu agugcugagg cauguggcua cagugauaga    960

guauuacagc ucaaauuagg aaauucagcu auugucaccc aggaagcagc gaacuacugc   1020

ugcgcuuaug gugaauggcc caauuacuua ccagaccaug aagcaguagc cauugauaaa   1080

ccuacacaac cagaaacugc uacagauaga uucuacacuu ugaaaucagu caaaugggaa   1140

acuggaagca caggauggug guggaaacua cccgaugcac ugaauaauau aggcauguuu   1200

ggacagaaug ugcagcauca cuaccuauau agaucugguu ucuugauuca ugugcagugu   1260

aaugccacaa aauuccauca aggugccuua uuagugguag caauuccaga acaucagagg   1320

ggagcgcaca acaccaacac uagcccaggg uuugaugaua uaaugaaagg ugaagaagga   1380

gggaccuuca aucauccaua uguccuugau gauggaacau cauuggcuug ugcgacgaua   1440
```

```
uuuccacauc aguggauaaa ucugagaacc aacaauucag caacaauugu ucuucccugg   1500
augaaugcug cuccaaugga uuucccacuu agacauaaauc aguggacgcu agcaauaaua   1560
ccaguggugc cauuagguac gcguacaaca ucaaguaugg ucccaauaac aguuucaauc   1620
gcuccaaugu guugugaguu uaauggacuu agacacgcca uuacucaagg ugucccaaca   1680
uaccuuuuac caggcucggg acaauuccua acaacugaug aucauagcuc ugcaccagcu   1740
cucccguguu ucaacccaac uccagaaaug cauaucccag ggcagguccg uaacaugcua   1800
gaaguggucc aaguggaauc aaugauggag auuaauaaca cagaaagugc aguuggcaug   1860
gagcgucuua agguugauau aucagcauug acagaugucg aucaauuguu auucaacauu   1920
ccacuggaca uacaguugga ugggccacuu agaaacacuu ugguaggaaa cauaucuaga   1980
uauuacacuc auuggucugg aucccuagaa augacguuua uguuuugugg cagcuucaug   2040
gcaacgggaa aauuaauccu gugcuauacu ccuccaggug gaucaugccc gacaaccaga   2100
gagaccgcca uguuagguac acauauuguu ugggauuuug gauuacaauc uaguguaacc   2160
cugauaauac cuuggauuag uggaucccac uacaggaugu uuaauaauga ugcuaaguca   2220
acuaaugcca acguuggcua ugucacuugu uuuaugcaga ccaaucugau aguccccagu   2280
gaauccucug acacguguuc cuugauaggg uucauagcag caaaagauga uuucucccuc   2340
agauuaauga gagacagccc ugacauugga caacuagacc auuuacaugc agcagaggca   2400
gccuaccaga ucgagagcau caucaaaaca gcgaccgaca cugugaaaag ugagauuaau   2460
gcugaacuug guguggucoc uagcuuaaau gcaguugaaa caggugcaac uucuaacacu   2520
gaaccagaag aagccauaca aacucgcaca gugauaaauc agcacggugu auccgagacu   2580
cuaguggaga auuuucucag uagagcagcu uugguaucaa agagaaguuu ugaauacaaa   2640
gaucauacuu cgucugcagc acaagcagac aagaacuuuu ucaaauggac aauuaacacc   2700
agauccuuug uacaguuaag aagaaaauua gaauuauuca cauaccuuag auuugaugcu   2760
gagaucacua uacucacaac uguagcagug aaugguagug guaauaaauac auacgugggu   2820
cuuccugacu ugacacucca agcaauguuu guacccacug gugcucuuac cccagaaaaa   2880
caggacucau uccacuggca gucaggcagu aaugcuagug uauucuuuaa aaucuccgac   2940
cccccagcca gaauaaccau accuuuuaug ugcauuaacu cagcauacuc aguuuuuuau   3000
gauggcuuug ccggauuuga gaaaaacggu cuguauggaa uaaauccagc ugacacuauu   3060
gguaacuuau guguuagaau agugaaugaa caccaaccag uugguuucac agugaccguu   3120
aggguuuaca ugaagccuaa acacauaaaa gcaugggcac cacgaccacc acgaacuuug   3180
ccauauauga guauugcaaa ugcaaauuac aaagguaaag aaagagcacc aaaugcgcuc   3240
aaugcuauaa uuggcaauag agacagugcuc aaaaccaugc cucauaauau agugaacacu   3300
gguccaggcu ucaugaagca ccugugguuc uuccugcugc ugguggccgc uccuaggugg   3360
gugcuguccc aggugcagcu ggugcagagc ggcguggagg ugaagaagcc cggcgcuucc   3420
gugaaggugu ccugcaaggc cuccggcuac accuucacca acuacuacau guacugggug   3480
aggcaggccc cuggacaggg acuggagugg augggcggca ucaacccuuc caacggcggc   3540
accaacuuca acgagaaguu caagaaccgg gugacccuga ccaccgacuc cuccaccacc   3600
accgccuaca uggagcugaa gucccugcag uuugacgaca ccgccgugua cuacugcgcc   3660
aggagggacu accgguucga caugggcuuc gacuacuggg gccagggcac aaccgugacc   3720
guguccagcg gagguggcgg aucuggaggg ggugguagcg guggaggcgg gagugagauc   3780
gugcugaccc aguccccugc uacacugucc cugucccccg gcgagagggc uacacugagc   3840
```

```
ugcagggccu ccaagggcgu guccaccucc ggcuacuccu accugcacug guaccagcag   3900

aagccuggac aggcucccag gcugcugauc uaccuggccu ccuaccugga guccggcgug   3960

ccugcuaggu uuuccggcag cggcagcggc accgauuuca cccugaccau cuccucccug   4020

gagcccgagg acuucgccgu guacuacugc cagcacucca gggaucugcc ucugaccuuc   4080

ggcggcggca ccaaggugga gaucaagagu gucaaaacca ugccucauaa uauagugaac   4140

acugguccag gcuucggagg aguuuuugua gggucuuuca aaauaaucaa cuaucacuug   4200

gccacuacag aagagagaca gucagcuauc uauguggauu ggcaaucaga cgucuugguu   4260

acccccauug cugcucaugg aaggcaccaa auagcaagau gcaagugcaa cacagggguu   4320

uacuauugua ggcacaaaaa cagaaguuac ccgauuugcu uugaaggccc agggauucaa   4380

uggauugaac aaaaugaaua uuacccagca agguaccaga ccaauguacu auuggcaguu   4440

gguccugcgg aagcaggaga uugcggugg u uuacuaguuu guccacaugg gguaaucggu   4500

cuucuuacag caggaggggg uggaauugua gcuuucacug auaucaggaa uuugcuaugg   4560

uuagauacug augcuaugga acaaggcauu acugauuaua uucaaaaucu ugguaaugcc   4620

uuuggagcag gauuuacaga aacaaucucu aauaaagcca aggaagugca agauaugcua   4680

auuggagaga guucacuauu agaaaaauug uuaaaagcuc uaaucaaaau cauaucagca   4740

uuaguaauug uaaucagaaa cucagaagau uuagucacag ucacagccac acuagcauug   4800

uugggaugcc augauucacc auggagcuac uugaaacaga agguauguuc auacuuaggu   4860

auuccuuaug uaccuagaca gggugaaucg uggcuuaaga aauucacaga ggcaugcaau   4920

gcucuuagag gucuggauug gcuaucgcaa aagauagaua aauucaucaa cuggcuuaaa   4980

accaaaauau uaccagaagc uagggagaaa uaugaauuug ugcaaaggcu caaacaguua   5040

ccggugauag aaaaccaagu uaguacaauc gagcauagcu gcccaacaac agaacaacaa   5100

caggccuuau ucaacaacgu ccaauacuau ucacacuacu guagaaagua cgcaccacuu   5160

uacgcagugg aagcaaagag gguaguagcu cuugaaaaga aaauaaacaa cuacauccag   5220

uucaagucca aaucucgcau ugaaccgguu uguuuaauaa uacauggcuc uccaggaacu   5280

ggcaagucag uggcuucaaa uuuaauugcc agggcuauca cagagaaauu gggggggac   5340

auuuauuccu ugccuccaga cccuaaauau uuugauggau acaaacagca aacaguggu c   5400

cucauggaug auuuaaugca aaauccagau gggaaugaca uaucuauguu cugccaaaug   5460

gucuccacug uagauuucau acccccaaug gcuaguuugg aggaaaaagg aacucuauac   5520

accaguccau uuuuaauagc uacuaccaau gcuggcucaa uacaugcacc aacuguauca   5580

gacucaaagg cuuugucacg cagauuuaaa uuugacgugg acauugaagu cacagauuca   5640

uacaaggacu caaauaaauu ggauauguca agggcagucg agaugugcaa accagauggc   5700

ugugccccca ccaauuacaa aagaugcugc ccauugaucu guggaaaggc uauccaauuc   5760

agagaucgca gaacuaaugc aagauccacu auugauaugc uaguaacuga uauuauaaag   5820

gaauauagaa ccagaaacag uacacaggau aagcuggaag cucuguuuca ggggccucca   5880

caguuuaaag agaucaaaau uucagucacc ccagauacac cagcuccuga ugcuauaaau   5940

gaccuucuua ggucagugga uucucaagaa guuagggauu auugccaaaa gaaaggaugg   6000

auuguaguac acccaucaaa ugagcuaaua guagaaaaac acauuaguag agcuuuuauu   6060

acucuacaag ccauugccac cuuuguauca auagcuggug uaguuuaugu uauauacaaa   6120

cuuuuugcug gcauucaggg uccauacaca ggaaucccca auccuaaacc uaaaguaccc   6180
```

```
ucucucagaa cagcuaaagu gcaaggacca ggguucgauu uugcacaagc cauaaugaag   6240
aaaaauaccg ucauugcaag gacugaaaag ggugaguuca ccaugcuggg uguauaugau   6300
aggguagcgg ucauccccac acacgcaucu guuggagaaa ccauuuacau uaaugaugua   6360
gagacuaaag uuuuagaugc gugugcacuu agagacuuga cugauacaaa cuuagagaua   6420
accauaguca aauuagaccg uaaucaaaaa uuuagagaua ucagacauuu ucugcccaga   6480
uaugaggaug auuacaauga cgcugugcuu agcguacaua caucaaaauu cccaaauaug   6540
uauaucccag uuggacaagu caccaauuau ggcuucuuga accuaggugg uacaccgacg   6600
caccgcauuu uaauguauaa cuucccaaca agagcuggcc aguguggugg ugugguugaca   6660
acuacaggua aggugauagg aauacaugua gguggaaaug gagcucaagg auuugcagca   6720
augcuacuac acucuuacuu uuccgauaca caaggugaga uaguuaguag ugaaaagagu   6780
ggggugugca uuaacgcacc ggcaaagacu aaacuccaac cuaguguuuu ccaucaaguu   6840
uuugaagguu caaaggaacc agcaguucuc aauccaaaag auccuaggcu uaaaacagau   6900
uucgaggagg ccauuuucuc aaaguacaca gguaacaaaa uuauguuaau ggaugaguac   6960
auggaagagg caguggauca uuaugugggg uguuuagaac cauuagacau caguguggau   7020
cccauacccc uggaaagugc cauguaugga auggauggcc uugaggcauu agacuuaacu   7080
accagugcag gauucccuua cuuacuacaa gggaagaaga aaagggauau auuuaauaga   7140
cauacuagag acaccaguga aaugacaaaa auguuagaga aauauggagu ugaccuaccu   7200
uuuguaaccu uuguaaaaga ugagcuuaga ucaagagaaa aaguugaaaa agggaaauca   7260
cgccugauug aggccaguuc cuugaaugac ucaguugcua ugagaguugc cuuuggaaac   7320
cuuuacgcca cauuucacaa caauccaggu acagcaacug guagugcagu ugguugugau   7380
ccagauauau uuuggucaaa aaucccuauu uuguuagaug gagaaaucuu ugcuuuugac   7440
uacacugguu augaugcuag uuugucacca gugugguuug ccugcuuaaa gaaaguucua   7500
auuaaguuag guuacacaca ucaaacgucu uuuauagauu auuuguguca uucaguacau   7560
uuauauaagg acaaaaaaua cauaguuaau gguggaaugc ccucugguuc uucaggcacc   7620
agcauauuca acacuaugau caacaauaua aucauaagaa cuuuauuaau uaggguuuac   7680
aaaggcauag accuggacca guucaaaaug auugccuaug ggaugaugu uauugcuagc   7740
uacccacaua agauugaucc agguuugcug gcagaagcag guaaacagua uggauuagua   7800
augacgccag cagacaaagg aaccaguuuu auugacacaa auugggaaaa uguaacuuuc   7860
uuaaaaagau auuucagagc agaugaucaa uaccccuuuc ucauacaucc agugaugcca   7920
augaaagaga uacaugaauc uauuagaugg acuaaagauc ccagaaacac acaggaucau   7980
guuaggucuu ugugcuaccu cgcauggcau aauggagagg aggcuuauaa ugaauuuugc   8040
agaaaaauca gaagugugcc ugugggaaga gcauugacac uaccugcaua cucuagucuu   8100
agacggaaau gguuagauuc guucuagaca acucuaauug aaacccaagu uauaguuacu   8160
uucauuuaga gguaaauuuu ggucacuugg gggccaaaaa aaaaaaaaaa aaaaaaaaaa   8220
gucgac                                                              8226
```

<210> SEQ ID NO 17
<211> LENGTH: 22
<212> TYPE: DNA
<213> ORGANISM: Artificial Sequence
<220> FEATURE:
<223> OTHER INFORMATION: DNA sequence of miR-133 target sequence

<400> SEQUENCE: 17

```
acagctggtt gaaggggacc aa                                              22


<210> SEQ ID NO 18
<211> LENGTH: 22
<212> TYPE: DNA
<213> ORGANISM: Artificial Sequence
<220> FEATURE:
<223> OTHER INFORMATION: DNA sequence of miR-206 target sequence

<400> SEQUENCE: 18

ccacacactt ccttacattc ca                                              22


<210> SEQ ID NO 19
<211> LENGTH: 102
<212> TYPE: DNA
<213> ORGANISM: Artificial Sequence
<220> FEATURE:
<223> OTHER INFORMATION: DNA sequence of tandem sequence of miR-133
      target sequence and miR-206 target sequence

<400> SEQUENCE: 19

acagctggtt gaaggggacc aacgatacag ctggttgaag ggaccaaac cggtccacac      60

acttccttac attccatcac ccacacactt ccttacattc ca                       102


<210> SEQ ID NO 20
<211> LENGTH: 507
<212> TYPE: DNA
<213> ORGANISM: Artificial Sequence
<220> FEATURE:
<223> OTHER INFORMATION: DNA sequence of the internal ribosome entry
      site sequence of HRV2

<400> SEQUENCE: 20

aacttagaag tttttcacaa agaccaatag ccggtaatca gccagattac tgaaggtcaa      60

gcacttctgt ttccccggtc aatgttgata tgctccaaca gggcaaaaac aactgcgatc     120

gttaaccgca aagcgcctac gcaaagctta gtagcatctt tgaaatcgtt tggctggtcg     180

atccgccatt tcccctggta gacctggcag atgaggctag aaatacccca ctggcgacag     240

tgttctagcc tgcgtggctg cctgcacacc ctatgggtgt gaagccaaac aatggacaag     300

gtgtgaagag ccccgtgtgc tcgctttgag tcctccggcc cctgaatgtg gctaacctta     360

accctgcagc tagagcacgt aacccaatgt gtatctagtc gtaatgagca attgcgggat     420

gggaccaact actttgggtg tccgtgtttc actttttcct ttatatttgc ttatggtgac     480

aatatataca atatatatat tggcacc                                        507
```

VIRUS FOR TREATMENT OF TUMOR

TECHNICAL FIELD

The present invention relates to the field of viruses and the field of tumor treatment. Specifically, the present invention relates to use of an Enterovirus D68 (EV-D68) or a modified form thereof, or a nucleic acid molecule comprising a genomic sequence or cDNA sequence of EV-D68 or a modified form thereof, or a complementary sequence of the genomic sequence or cDNA sequence, for treating a tumor in a subject (e.g., a human), and for manufacture of a medicament for treating a tumor in a subject (e.g., a human). The present invention also relates to a method for treating a tumor, which comprises a step of administering to a subject in need thereof EV-D68 or a modified form thereof, or a nucleic acid molecule comprising a genomic sequence or cDNA sequence of EV-D68 or a modified form thereof, or a complementary sequence of the genomic sequence or cDNA sequence.

BACKGROUND ART

The current methods for treatment of malignant tumors include surgery chemotherapy and radiotherapy. These traditional therapies are not satisfactory for the treatment of metastatic tumors, and may also cause great harm to patients' health. In contrast, as a new type of treatment method, the tumor treatment method using oncolytic virus has high specificity, good effectiveness, and less side effects, and is currently considered as a promising tumor treatment method.

Oncolytic virus is a virus that can self-replicate in tumor cells, thereby killing and lysing the tumor cells, or arresting the growth of the tumor cells. When used in in vivo treatment, oncolytic virus shows specificity for tumor cells, and can directly induce death of tumor cells, but has little or no effect on normal cells. Meanwhile, oncolytic virus can also induce cytotoxic T lymphocyte response in the immune system, thereby indirectly killing tumor cells.

Enterovirus belongs to Picornaviridae family, and its genome is single-stranded positive-sense RNA. There are following advantages in using enterovirus as oncolytic virus: firstly, as single-stranded RNA virus, its genome won't undergo any stages of DNA in the host, so that there won't be genotoxicity caused by the insertion of the viral genome into the host's DNA, which has better safety; secondly, the enterovirus genome is relatively small, and a large number of viruses can be replicated in a short period of time to further infect other tumor cells, causing a strong cytopathic effect; next, the enterovirus does not contain oncogenes and therefore does not induce tumor; and finally, the genome of the enterovirus can be modified by reverse genetics technology to achieve attenuation of virus and reduce its side effects.

At present, the reported enteroviruses with oncolytic activity include chimeric polioviruses for the treatment of human solid tumors such as malignant gliomas (Dobrikova et al., Mol Ther 2008, 16 (11): 1865-1872); Coxsackie viruses A13, A15, A18, and A21 that kill human melanoma cells (Au et al., \Tirol J 2011, 8: 22); Echo virus ECHO1 that kills human gastric cancer cells and ovarian cancer cells (Shafren et al., Int J Cancer 2005, 115 (2): 320-328; Haley et al., J Mol Med (Berl) 2009, 87 (4): 385-399) and the like. However, it is still necessary to obtain viruses with both tumor-specificity and tumor-killing activity.

Enterovirus D68 (EV-D68) is a kind of Enterovirus D of the genus Enteroviruses of Picornaviridae family, which was first isolated from children with respiratory infections in California in 1962 (Schieble et al., Am J Epidemiol 1967, 85 (2): 297-310). Unlike most enteroviruses, which are resistant to acids and reproduce in the human gastrointestinal tract, EV-D68 is sensitive to acids and replicates mainly in the respiratory tract. Since there have been few reports of EV-D68 infection for a long time, EV-D68 is considered to be a rare pathogen that mainly causes mild respiratory diseases, including ninny nose, sneezing, and cough. At present, there is not report in the art that enterovirus 68 has oncolytic activity.

CONTENTS OF THE INVENTION

After a lot of experiments and repeated explorations, it is unexpectedly found that Enterovirus D68 has a broad spectrum and significant tumor cell killing ability. Based on this finding, the inventors of the present invention have developed a new oncolytic virus for treating tumors and a tumor treatment method based on the virus.

Medical Use

In a first aspect, the present invention provides use of an Enterovirus D68 (EV-D68) or a modified form thereof, or an isolated nucleic acid molecule, in treatment of a tumor in a subject, or in the manufacture of a medicament for treating a tumor in a subject; wherein the isolated nucleic acid molecule comprises a sequence selected from the following:

(1) a genomic sequence or cDNA sequence of EV-D68 or a modified form thereof; and (2) a complementary sequence of the genomic sequence or cDNA sequence.

In certain preferred embodiments, the EV-D68 is a wild-type EV-D68. In certain preferred embodiments, the EV-D68 may be a clinical isolate isolated from an individual infected with the Enterovirus D68.

In certain preferred embodiments, the EV-D68 or a modified form thereof has a genomic sequence that has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence as shown in SEQ ID NO: 12. In certain preferred embodiments, the genomic sequence of the EV-D68 or a modified form thereof is a nucleotide sequence as shown in SEQ ID NO: 12.

In certain preferred embodiments, the EV-D68 or a modified form thereof has a cDNA sequence that has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence shown in SEQ ID NO: 1. In certain preferred embodiments, the cDNA sequence of the EV-D68 or a modified form thereof is a nucleotide sequence as shown in SEQ ID NO: 1.

In certain preferred embodiments, the modified form is a modified EV-D68, which has a substitution, insertion, or deletion of one or more nucleotides in the genome as compared to a wild-type EV-D68.

In certain preferred embodiments, as compared to the wild-type EV-D68, the modified EV-D68 has one or more modifications selected from the following:

(1) one or more mutations in an untranslated region (e.g., 5'UTR or 3'UTR);

(2) an insertion of one or more exogenous nucleic acids;

(3) a deletion or mutation of one or more endogenous genes; and (4) any combination of the above three items.

In certain preferred embodiments, the modified EV-D68 includes one or more mutations in the 5' untranslated region (5'UTR).

In certain preferred embodiments, the modified EV-D68 has a substitution of all or part of the 5'UTR sequence. In certain preferred embodiments, the internal ribosome entry site (IRES) sequence in the 5'UTR of the modified EV-D68 is replaced with an exogenous IRES sequence, such as the internal ribosome entry site sequence of human rhinovirus 2 (HRV2). In certain preferred embodiments, the internal ribosome entry site sequence of the human rhinovirus 2 (HRV2) is shown in SEQ ID NO: 2.

The use of the internal ribosome entry site sequence of human rhinovirus 2 (HRV2) is advantageous in some cases, for example, it is conducive to improvement of the tumor specificity of oncolytic viruses. It has been previously reported that in normal human nerve cells, the internal ribosome entry site sequence of human rhinovirus 2 is specifically bound by host RNA-binding proteins (DRBP76 and NF45), thereby preventing the recruitment of factors such as eIF4G (Merrill et al. J Virol 2006, 80 (7): 3147-3156; Merrill and Gromeier, J Virol 2006, 80 (14): 6936-6942; Neplioueva et al., PLoS One 2010, 5 (7): e11710); meanwhile, due to the lack of support of signaling pathways such as Raf/Erk1/2/MAPK, it is difficult for ribosomes to bind to the internal ribosome entry site sequence of human rhinovirus 2, so that it is impossible to initiate translation of viral protein (Dobrikov et al., Mol Cell Biol 2011, 31(14): 2947-2959; Dobrikov et al., Mol Cell Biol 2013, 33(5): 937-946). In human glioma tumor cells, the internal ribosome entry site of human rhinovirus 2 is not affected by the above two factors, and thus can normally initiate transcription and translation of viral protein. Therefore, in some cases, replacing the internal ribosome entry site sequence of EV-D68 with the internal ribosome entry site sequence of human rhinovirus 2 is beneficial to avoid or reduce the toxic and side effect of the virus of the present invention to normal human nerve cells, without affecting the use of the virus in the treatment of human gliomas.

In certain preferred embodiments, the modified EV-D68 comprises an exogenous nucleic acid.

In certain preferred embodiments, the exogenous nucleic acid encodes a cytokine (e.g., GM-CSF, preferably human GM-CSF), or an antitumor protein or polypeptide (e.g., a scFv against PD-1 or PD-L1, preferably a scFv against human PD-1 or PD-L1). In certain preferred embodiments, the exogenous nucleic acid is inserted between the 5'UTR gene and the VP4 gene, or between the VP1 gene and the 2A gene of the genome of the modified EV-D68.

In certain preferred embodiments, the exogenous nucleic acid comprises a target sequence of microRNA (miRNA) (e.g., miR-133 or miR-206). In certain preferred embodiments, the target sequence of microRNA inserted in the 3' untranslated region (3'UTR) of the genome of the modified EV-D68.

It has been previously reported that the expression level of certain microRNA in tumor cells is significantly lower than normal cells and/or has obvious tissue specificity. Therefore, in some cases, the modified EV-D68 of the present invention containing a target sequence of such microRNA is advantageous, because such microRNA that are highly expressed in normal cells or tissues can reduce or even block the replication of the modified EV-D68 in the normal cells or tissues by the corresponding target sequence, thereby reducing even avoiding the toxic side effects of the modified EV-D68 on non-tumor cells. Such microRNAs include but are not limited to miR-133, miR-206, miR-1, miR-143, miR-145, miR-217, let-7, miR-15, miR-16, etc. (see, for example, PCT International Application WO2008103755A1, US patent application US20160143969A1, or Baohong Zhang et al., Developmental Biology, Volume 302, Issue 1, 1 Feb. 2007, Pages 1-12; all of these documents are incorporated herein by reference).

In certain preferred embodiments, the exogenous nucleic acid comprises a target sequence of one or more (e.g., 2, 3, or 4) microRNA as described above. In certain preferred embodiments, the exogenous nucleic acid comprises a target sequence of miR-133 and/or miR-206. In certain preferred embodiments, the target sequence of miR-133 is shown in SEQ ID NO: 3. In certain preferred embodiments, the target sequence of miR-206 is shown in SEQ ID NO: 4. In some cases, the insertion of the target sequence of miR-133 and/or miR-206 is advantageous. This is because miR-133 and miR-206 are specifically expressed in muscle tissue, so that the tissue tropism of the oncolytic virus can be changed by inserting the target sequence of miR-133 and/or miR-206 into the modified EV-D68, thereby reducing or avoiding damage to normal muscle tissue.

In certain preferred embodiments, the modified EV-D68 comprises at least one insertion of the exogenous nucleic acid as described above and/or at least one mutation in the untranslated region as described above.

In certain preferred embodiments, the genomic sequence of the modified EV-D68 has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence selected from: the nucleotide sequences as shown in SEQ ID NOs: 13-16. In certain preferred embodiments, the genomic sequence of the modified EV-D68 is selected from the nucleotide sequences as shown in any one of SEQ ID NOs: 13-16.

In certain preferred embodiments, the cDNA sequence of the modified EV-D68 has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence selected from: the nucleotide sequences as shown in SEQ ID NOs: 8-11. In certain preferred embodiments, the cDNA sequence of the modified EV-D68 is selected from the nucleotide sequences as shown in any one of SEQ ID NOs: 8-11.

In the present invention, the modified EV-D68 can be obtained by reverse genetics technology, and the reverse genetics technology is known in the art, for example, see Yang L S, Li S X, Liu Y J, et al Virus Res, 2015, 210: 165-168; Hou W H, Yang L S, Li S X, et al. Virus Res, 2015, 205: 41-44; which is incorporated herein by reference in its entirety. In such embodiments, the modified EV-D68 is typically obtained by modifying the cDNA of wild-type EV-D68 (e.g., insertion of an exogenous nucleic acid, deletion or mutation of an endogenous gene, or mutation in a non-translated region).

In the present invention, the EV-D68 or a modified form thereof may be pretreated to reduce or eliminate the immune response against the virus in a subject, wherein the pretreatment may comprise: packaging the EV-D68 in a lipidosome or micelle, and/or using a protease (e.g., chymotrypsin or trypsin) to remove the capsid protein of the virus to reduce the humoral and/or cellular immunity against the virus in host.

In the present invention, the EV-D68 or a modified form thereof can be serially passaged for adaptation in tumor cells. In certain preferred embodiments, the tumor cells may be tumor cell lines or tumor cell strains known in the art, or may be tumor cells obtained by surgical resection or clinical isolation from an individual (e.g., a subject) having a tumor. In certain preferred embodiments, the EV-D68 or a modified form thereof is serially passaged for adaptation in tumor cells obtained from an individual (e.g., a subject) having a tumor. In certain preferred embodiments, the tumor cells are obtained by surgical resection or clinical isolation from an individual (e.g., a subject) having a tumor. In certain preferred embodiments, the method for serial passaging for adaptation comprises a plurality of (e.g., at least 5, at least 10, at least 15, at least 20) cycles consisting of the following processes: 1) infecting a target tumor cell with a virus; 2) harvesting the virus in a supernatant; and 3) reinfecting a fresh target tumor cell with the obtained virus.

In certain preferred embodiments, the EV-D68 and modified forms thereof as described above can be used in combination. Therefore, the medicament may comprise one or several of EV-D68 and modified forms thereof.

In certain preferred embodiments, the isolated nucleic acid molecule consists of a genomic sequence or cDNA sequence of EV-D68 or a modified form thereof as described above, or a complementary sequence of the genomic sequence or cDNA sequence. In certain preferred embodiments, the isolated nucleic acid molecule has a genomic sequence of EV-D68 or a modified form thereof as described above. In certain preferred embodiments, the isolated nucleic acid molecule is RNA. In certain preferred embodiments, the isolated nucleic acid molecule has a nucleotide sequence as shown in any one of SEQ ID NOs: 12-16.

In certain preferred embodiments, the isolated nucleic acid molecule is a vector (e.g. cloning vector or expression vector) comprising a genomic sequence or cDNA sequence of EV-D68 or a modified form thereof as described above, or a complementary sequence of the genomic sequence or cDNA sequence. In certain preferred embodiments, the isolated nucleic acid molecule is a vector (e.g., cloning vector or expression vector) comprising a cDNA sequence of EV-D68 or a modified form thereof as described above, or a complementary sequence of the cDNA sequence. In certain preferred embodiments, the isolated nucleic acid molecule is a vector comprising a nucleotide sequence as shown in any one of SEQ ID NOs: 1, 8-11 or a complementary sequence thereof.

In certain preferred embodiments, the isolated nucleic acid molecule comprises the complementary sequence of the genomic sequence of EV-D68 or a modified form thereof as described above. In certain preferred embodiments, the complementary sequence is complementary to a nucleotide sequence selected from:

(1) a nucleotide sequence as shown in SEQ ID NO: 12;

(2) a nucleotide sequence having a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to the nucleotide sequence as shown in SEQ ID NO: 12;

(3) a nucleotide sequence as shown in any one of SEQ ID NOs: 13-16; and (4) a nucleotide sequence having a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to the nucleotide sequence as shown in any of SEQ ID NOs: 13-16.

In certain preferred embodiments, the isolated nucleic acid molecule comprises a complementary sequence to the cDNA sequence of EV-D68 or a modified form thereof as described above. In certain preferred embodiments, the complementary sequence is complementary to a nucleotide sequence selected from:

(1) a nucleotide sequence as shown in SEQ ID NO: 1;

(2) a nucleotide sequence having a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to the nucleotide sequence as shown in SEQ ID NO: 1;

(3) a nucleotide sequence as shown in any one of SEQ ID NOs: 8-11; and (4) a nucleotide sequence having a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to the nucleotide sequence as shown in any one of SEQ ID NOs: 8-11.

In the present invention, the isolated nucleic acid molecule can be delivered by any means known in the art, for example, a naked nucleic acid molecule (e.g., a naked RNA) can be directly injected, or a non-viral delivery system can be used. The non-viral delivery system can be obtained from a variety of materials well known in the art, including, but not limited to, the materials described in detail in "Yin H, et al. Nat Rev Genet. 2014 August; 15(8): 541-55." and "Riley M K, Vermerris W. Nanomaterials (Base1). 2017 Apr. 28; 7(5). Pii: E94.", which are incorporated herein by reference in their entirety, such as liposomes, inorganic nanoparticles (such as gold nanoparticles), polymers (such as PEG), and so on.

In certain preferred embodiments, the medicament comprises a therapeutically effective amount of the EV-D68 and/or a modified form thereof as described above, or a therapeutically effective amount of the isolated nucleic acid molecule as described above. In certain preferred embodiments, the medicament may be in any form known in the medical arts. For example, the medicament may be in the form of a tablet, a pill, a suspension, an emulsion, a solution, a gel, a capsule, a powder, a granule, an elixir, a lozenge, a suppository, or an injection (including injection solution, lyophilized powder) and so on. In some embodiments, the medicament is an injection solution or a lyophilized powder.

In certain preferred embodiments, the medicament further comprises a pharmaceutically acceptable carrier or excipient. In certain preferred embodiments, the medicament comprises a stabilizer.

In certain preferred embodiments, the medicament optionally further comprises an additional pharmaceutically active agent. In a preferred embodiment, the additional pharmaceutically active agent is a medicament having antitumor activity, such as an additional oncolytic virus, chemotherapeutic agent or immunotherapeutic agent.

In the present invention, the additional oncolytic virus includes, but is not limited to, herpesvirus, adenovirus, parvovirus, reovirus, Newcastle disease virus, vesicular stomatitis virus, measles virus, or any combination thereof. The chemotherapeutic agent includes but is not limited to 5-fluorouracil, mitomycin, methotrexate, hydroxyurea, cyclophosphamide, dacarbazine, mitoxantrone, anthracyclines (e.g., epirubicin or doxorubicin), etoposide, platinum compounds (e.g., carboplatin or cisplatin), taxanes (e.g., paclitaxel or taxotere), or any combination thereof. The immunotherapeutic agent includes, but is not limited to, immune checkpoint inhibitors (e.g., PD-L1/PD-1 inhibitors or CTLA-4 inhibitors), tumor-specific targeting antibodies (e.g., rituximab or Herceptin) or any combination thereof.

In certain preferred embodiments, the medicament comprises a unit dose of the EV-D68 and/or a modified form thereof as described above, for example comprising at least $1\times10^2$ pfu, at least $1\times10^3$ pfu, at least $1\times10^4$ pfu, $1\times10^5$ pfu, $1\times10^6$ pfu, at least $1\times10^7$ pfu, at least $1\times10^8$ pfu, at least $1\times10^9$ pfu, at least $1\times10^{10}$ pfu, at least $1\times10^{11}$ pfu, at least $1\times10^{12}$ pfu, at least $1\times10^{13}$ pfu, at least $1\times10^{14}$ pfu, or at least $1\times10^{16}$ pfu of the EV-D68 and/or a modified form thereof. In certain preferred embodiments, the medicament comprises $1\times10^2$ pfu to $1\times10^{17}$ pfu of the EV-D68 and/or a modified form thereof as described above.

In certain preferred embodiments, the medicament contains a unit dose of an isolated nucleic acid molecule as described above, such as the nucleic acid molecule containing $3\times10^{10}$ to $3\times10^{14}$ virus genome copies.

In certain preferred embodiments, the medicament may be administered in combination with an additional therapy. This additional therapy may be any therapy known for tumors, such as surgery, chemotherapy, radiation therapy, immunotherapy, hormone therapy or gene therapy. This additional therapy may be administered before, concurrently with, or after the administration of the medicament.

In certain preferred embodiments, the tumor includes, but is not limited to, cervical cancer, ovarian cancer, endometrial cancer, lung cancer, liver cancer, kidney cancer, neuroblastoma, glioma, breast cancer, melanoma, prostate cancer, bladder cancer, pancreatic cancer, gastric cancer, colorectal cancer, esophageal cancer, thyroid cancer, laryngeal cancer, osteosarcoma, hematopoietic malignancy (e.g., lymphoma or leukemia).

In certain preferred embodiments, the subject is a mammal, such as a human.

In another aspect, the invention also relates to use of the EV-D68 and/or a modified form thereof as defined in the first aspect, or the isolated nucleic acid molecule as defined in the first aspect, as a medicament.

Treatment Method

In a second aspect, the present invention provides a method for treating a tumor, comprising the step of administering to a subject in need thereof an effective amount of an EV-D68 or a modified form thereof, or an effective amount of an isolated nucleic acid molecule; wherein the isolated nucleic acid molecule comprises a sequence selected from the group consisting of:

(1) a genomic sequence or cDNA sequence of EV-D68 or a modified form thereof; and (2) a complementary sequence of the genomic sequence or cDNA sequence.

In certain preferred embodiments, EV-D68 is administered to the subject. In certain preferred embodiments, the EV-D68 is wild-type EV-D68. In certain preferred embodiments, the EV-D68 may be a clinical isolate that is isolated from an individual infected with Enterovirus D68.

In certain preferred embodiments, the genomic sequence of the EV-D68 or a modified form thereof has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to the nucleotide sequence as shown in SEQ ID NO: 12. In certain preferred embodiments, the genomic sequence of the EV-D68 or a modified form thereof is a nucleotide sequence as shown in SEQ ID NO: 12.

In certain preferred embodiments, the cDNA sequence of the EV-D68 or a modified form thereof has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to the nucleotide sequence as shown in SEQ ID NO: 1. In certain preferred embodiments, the cDNA sequence of the EV-D68 or a modified form thereof is a nucleotide sequence as shown in SEQ ID NO: 1.

In certain preferred embodiments, a modified form of EV-D68 is administered to the subject. In certain preferred embodiments, as compared to the wild-type EV-D68, the modified form is a modified EV-D68, which has a substitution, insertion, or deletion of one or more nucleotides in the genome.

In certain preferred embodiments, as compared to the wild-type EV-D68, the modified EV-D68 has one or more modifications selected from the following:

(1) one or more mutations in an untranslated region (e.g., 5'UTR or 3'UTR);

(2) an insertion of one or more exogenous nucleic acids;

(3) a deletion or mutation of one or more endogenous genes; and (4) any combination of the above three items.

In certain preferred embodiments, the modified EV-D68 includes one or more mutations in the 5' untranslated region (5'UTR).

In certain preferred embodiments, the modified EV-D68 has a substitution of all or part of the 5'UTR sequence. In certain preferred embodiments, the internal ribosome entry site (IRES) sequence in the 5'UTR of the modified EV-D68 is replaced with an exogenous IRES sequence, such as the interior ribosome entry site sequence of human rhinovirus 2 (HRV2). In certain preferred embodiments, the internal ribosome entry site sequence of the human rhinovirus 2 (HRV2) is shown in SEQ ID NO: 2.

In certain preferred embodiments, the modified EV-D68 comprises an exogenous nucleic acid.

In certain preferred embodiments, the exogenous nucleic acid encodes a cytokine (e.g., GM-CSF, preferably human GM-CSF), or an antitumor protein or polypeptide (e.g., scFv against PD-1 or PD-L1, preferably scFv against human PD-1 or PD-L1). In certain preferred embodiments, the exogenous nucleic acid is inserted between the 5'UTR gene and the VP4 gene, or between the VP1 gene and the 2A gene of the genome of the modified EV-D68.

In certain preferred embodiments, the exogenous nucleic acid comprises a target sequence of microRNA (miRNA) (e.g., miR-133 or miR-206) In certain preferred embodiments, the target sequence of microRNA is inserted in the 3' untranslated region (3'UTR) of the genome of the modified EV-D68.

In certain preferred embodiments, the exogenous nucleic acid comprises a target sequence of one or more (e.g., 2, 3, or 4) microRNA as described above. In certain preferred embodiments, the exogenous nucleic acid comprises a target sequence of miR-133 and/or miR-206. In certain preferred embodiments, the target sequence of miR-133 is shown in SEQ ID NO: 3. In certain preferred embodiments, the target sequence of miR-206 is shown in SEQ ID NO: 4.

In certain preferred embodiments, the modified EV-D68 comprises at least one insertion of the exogenous nucleic acid as described above and/or at least one mutation in the untranslated region as described above.

In certain preferred embodiments, the genomic sequence of the modified EV-D68 has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence selected from: the nucleotide sequences as shown in SEQ ID NOs: 13-16. In certain preferred embodiments, the genomic sequence of the modified EV-D68 is selected from the nucleotide sequence as shown in any one of SEQ ID NOs: 13-16.

In certain preferred embodiments, the cDNA sequence of the modified EV-D68 has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence selected from: the nucleotide sequences as shown in SEQ ID NOs: 8-11. In certain preferred embodiments, the cDNA sequence of the modified EV-D68 is selected from the nucleotide sequence as shown in any one of SEQ ID NOs: 8-11.

In certain preferred embodiments, the EV-D68 and modified forms thereof as described above can be used in combination. Thus, one or more of the EV-D68 and modified forms can be administered to a subject.

In certain preferred embodiments, the isolated nucleic acid molecule as described above is administered to the subject.

In certain preferred embodiments, the isolated nucleic acid molecule consists of the genomic sequence or cDNA sequence of the EV-D68 or a modified form thereof as described above, or the complementary sequence of the genomic sequence or cDNA sequence. In certain preferred embodiments, the isolated nucleic acid molecule has the genomic sequence of the EV-D68 or a modified form thereof as described above. In certain preferred embodiments, the isolated nucleic acid molecule is RNA. In certain preferred embodiments, the isolated nucleic acid molecule has a nucleotide sequence as shown in any one of SEQ ID NOs: 12-16.

In certain preferred embodiments, the isolated nucleic acid molecule is a vector (e.g. cloning vector or expression vector) comprising the genomic sequence or cDNA sequence of EV-D68 or a modified form thereof as described above, or the complementary sequence of the genomic sequence or cDNA sequence. In certain preferred embodiments, the isolated nucleic acid molecule is a vector (e.g., cloning vector or expression vector) comprising the cDNA sequence of EV-D68 or a modified form thereof as described above, or the complementary sequence of the cDNA sequence. In certain preferred embodiments, the isolated nucleic acid molecule is a vector comprising the nucleotide sequence as shown in any one of SEQ ID NOs: 1, 8-11 or the complementary sequence thereof.

In certain preferred embodiments, the isolated nucleic acid molecule comprises the complementary sequence of the genomic sequence of EV-D68 or a modified form thereof as described above. In certain preferred embodiments, the complementary sequence is complementary to a nucleotide sequence selected from:

(1) a nucleotide sequence as shown in SEQ ID NO: 12;

(2) a nucleotide sequence having a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to the nucleotide sequence as shown in SEQ ID NO: 12;

(3) a nucleotide sequence as shown in any one of SEQ ID NOs: 13-16; and (4) a nucleotide sequence having a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to the nucleotide sequence shown in any of SEQ ID NOs: 13-16.

In certain preferred embodiments, the isolated nucleic acid molecule comprises the complementary sequence of the cDNA sequence of EV-D68 or a modified form thereof as described above. In certain preferred embodiments, the complementary sequence is complementary to a nucleotide sequence selected from:

(1) a nucleotide sequence as shown in SEQ ID NO: 1;

(2) a nucleotide sequence having a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to the nucleotide sequence as shown in SEQ ID NO: 1;

(3) a nucleotide sequence as shown in any one of SEQ ID NOs: 8-11; and (4) a nucleotide sequence having a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to the nucleotide sequence as shown in any one of SEQ ID NOs: 8-11.

In the present invention, the isolated nucleic acid molecule can be delivered by any means known in the art, for example, a naked nucleic acid molecule (e.g., naked RNA) can be directly injected, or a non-viral delivery system can be used. The non-viral delivery system can be obtained from a variety of materials well known in the art, including, but not limited to, the materials described in detail in "Yin H, et al. Nat Rev Genet. 2014 August; 15(8): 541-55." and "Riley M K, Vermerris W. Nanomaterials (Base1). 2017 Apr. 28; 7(5). Pii: E94.", which are incorporated herein by reference in their entirety, such as liposomes, inorganic nanoparticles (such as gold nanoparticles), polymers (such as PEG), and so on.

In certain preferred embodiments, the EV-D68 and/or a modified form thereof as described above, or the isolated nucleic acid molecule as described above, can be formulated and administered as a pharmaceutical composition. Such a pharmaceutical composition may comprise a therapeutically effective amount of the EV-D68 and/or a modified form thereof as described above, or a therapeutically effective amount of the isolated nucleic acid molecule as described above. In certain preferred embodiments, the pharmaceutical composition may be in any form known in the medical arts. For example, the pharmaceutical composition may be in the form of a tablet, a pill, a suspension, an emulsion, a solution, a gel, a capsule, a powder, a granule, an elixir, a lozenge, a suppository, or an injection (including injection solution, lyophilized powder) and so on. In some embodiments, the medicament is an injection solution or a lyophilized powder.

In certain preferred embodiments, the pharmaceutical composition further comprises a pharmaceutically acceptable carrier or excipient. In certain preferred embodiments, the pharmaceutical composition comprises a stabilizer.

In the present invention, the EV-D68 and/or a modified form thereof, or the isolated nucleic acid molecule as described above can be administered to a subject by any suitable administration route. In some cases, the route of administration of the EV-D68 and/or a modified form thereof, or the isolated nucleic acid molecules as described above, depends on the location and type of tumor. For example, for a solid tumor that is easily accessible, the virus or nucleic acid molecule is optionally administered by injection directly into the tumor (e.g., intratumoral injection); for a tumor of hematopoietic system, the virus or nucleic acid molecule can be administered by intravenous or other intravascular routes; for a tumor that is not easily accessible in the body (e.g., metastases), the virus or nucleic acid molecule can be administered systematically so that it can run over the whole body and thereby reaching the tumor (e.g., intravenous or intramuscular injection). Optionally, the virus or nucleic acid molecule of the present invention can be administrated via subcutaneous, intraperitoneal, intrathecal (e.g., for brain tumors), topical (e.g., for melanoma), oral (e.g., for oral or esophageal cancer), intranasal or inhalation spray (e.g., for lung cancer) routes and so on. In certain preferred embodiments, the EV-D68 and/or a modified form thereof as described above, or the isolated nucleic acid as described above, can be administered via intradermal, subcutaneous, intramuscular, intravenous, oral routes etc.

In certain preferred embodiments, the method further comprises administering an additional pharmaceutically active agent having antitumor activity. This additional pharmaceutically active agent may be administered before, concurrently with or after the administration of the EV-D68 and/or a modified form thereof, or an isolated nucleic acid molecule as described above.

In certain preferred embodiments, the additional pharmaceutically active agent includes an additional oncolytic virus, chemotherapeutic agent, or immunotherapeutic agent. In the present invention, the additional oncolytic virus includes, but is not limited to, herpesvirus, adenovirus, parvovirus, reovirus, Newcastle disease virus, vesicular stomatitis virus, measles virus, or any combination thereof. The chemotherapeutic agent includes but is not limited to 5-fluorouracil, mitomycin, methotrexate, hydroxyurea, cyclophosphamide, dacarbazine, mitoxantrone, anthracyclines (such as epirubicin or doxorubicin), etoposide, platinum compounds (such as carboplatin or cisplatin), taxanes (such as paclitaxel or taxotere), or any combination thereof. The immunotherapeutic agents include, but are not limited to, immune check point inhibitors (such as PD-L1/PD-1 inhibitors or CTLA-4 inhibitors), tumor-specific targeting antibodies (such as rituximab or Herceptin) or any combination thereof.

In certain preferred embodiments, the EV-D68 and/or a modified form thereof can be administered in any amount from 1 to $1\times10^{15}$ pfu/kg of the subject's body weight, for example, the EV-D68 and/or a modified form thereof is administered in an amount of at least $1\times10^{3}$ pfu/kg, at least $1\times10^{4}$ pfu/kg, $1\times10^{5}$ pfu/kg, $1\times10^{6}$ pfu/kg, at least $1\times10^{7}$ pfu/kg, at least $1\times10^{8}$ pfu/kg, at least $1\times10^{9}$ pfu/kg, at least $1\times10^{10}$ pfu/kg, at least $1\times10^{11}$ pfu/kg, or at least $1\times10^{12}$ pfu/kg of the subjects body weight. In certain preferred embodiments, the isolated nucleic acid molecule as described above can be administered in any amount of $3\times10^{10}$ to $3\times10^{14}$ virus genome copies per kg of the subject's body weight. In certain preferred embodiments, the EV-D68 and/or a modified form thereof or the isolated nucleic acid molecule as described above can be administered 3 times a day, 2 times a day, 1 time a day, once every 2 days or once a week, optionally the above dosage regimen can be repeated weekly or monthly as appropriate.

In certain preferred embodiments, the method further comprises administering an additional therapy. This additional therapy may be any therapy known for tumors, such as surgery, chemotherapy, radiation therapy, immunotherapy, hormone therapy or gene therapy. This additional therapy may be administered before, concurrently with, or after the administration of the method described above.

In certain preferred embodiments, the subject is a mammal, such as a human.

In certain preferred embodiments, the tumor includes, but is not limited to, cervical cancer, ovarian cancer, endometrial cancer, lung cancer, liver cancer, kidney cancer, neuroblastoma, glioma, breast cancer, melanoma, prostate cancer, bladder cancer, pancreatic cancer, gastric cancer, colorectal cancer, esophageal cancer, thyroid cancer, laryngeal cancer, osteosarcoma, hematopoietic malignancy (e.g., lymphoma or leukemia).

Pharmaceutical Composition

In a third aspect, the present invention provides a pharmaceutical composition comprising an EV-D68 and/or a modified form thereof as defined in the first or second aspect, or an isolated nucleic acid molecule as defined in the first or second aspect.

In certain preferred embodiments, the pharmaceutical composition comprises the EV-D68 and/or a modified form thereof as defined in the first or second aspect. In certain preferred embodiments, the EV-D68 and/or modified forms thereof may be used in combination. Therefore, the pharmaceutical composition of the present invention may comprise one or several of the EV-D68 and/or modified forms thereof. In certain preferred embodiments, the pharmaceutical composition comprises a unit dose of the EV-D68 and/or a modified form thereof, for example at least $1\times10^{2}$ pfu, at least $1\times10^{3}$ pfu, at least $1\times10^{4}$ pfu, $1\times10^{5}$ pfu, $1\times10^{6}$ pfu, at least $1\times10^{7}$ pfu, at least $1\times10^{8}$ pfu, at least $1\times10^{9}$ pfu, at least $1\times10^{10}$ pfu, at least $1\times10^{11}$ pfu, at least $1\times10^{12}$ pfu, at least $1\times10^{13}$ pfu, at least $1\times10^{14}$ pfu, or at least $1\times10^{16}$ pfu of the EV-D68 and/or a modified form thereof. In certain preferred embodiments, the pharmaceutical composition comprises $1\times10^{2}$ pfu to $1\times10^{17}$ pfu of the EV-D68 and/or a modified form thereof.

In certain preferred embodiments, the pharmaceutical composition comprises an isolated nucleic acid molecule as defined in the first aspect or the second aspect. In certain preferred embodiments, the isolated nucleic acid molecules can be used in combination. Therefore, the pharmaceutical composition of the present invention may include one or several of the isolated nucleic acid molecules. In certain preferred embodiments, the pharmaceutical composition comprises a unit dose of the isolated nucleic acid molecule, for example $3\times10^{10}$ to $3\times10^{14}$ virus genome copies of the isolated nucleic acid molecule.

In certain preferred embodiments, the pharmaceutical composition may be in any form known in the medical arts. For example, the pharmaceutical composition may be in the form of a tablet, a pill, a suspension, an emulsion, a solution, a gel, a capsule, a powder, a granule, an elixir, a lozenge, a suppository, or an injection (including injection solution, lyophilized powder) and so on. In some embodiments, the medicament is an injection solution or a lyophilized powder.

In certain preferred embodiments, the pharmaceutical composition further comprises a pharmaceutically acceptable carrier or excipient. In certain preferred embodiments, the pharmaceutical composition comprises a stabilizer.

In certain preferred embodiments, the pharmaceutical composition optionally further comprises an additional pharmaceutically active agent. In a preferred embodiment, the additional pharmaceutically active agent is a medicament having antitumor activity, such as an additional oncolytic virus, chemotherapeutic agent or immunotherapeutic agent.

In certain preferred embodiments, the pharmaceutical composition is used to treat a tumor in a subject.

In certain preferred embodiments, the subject is a mammal, such as a human.

In certain preferred embodiments, the tumor includes, but is not limited to, cervical cancer, ovarian cancer, endometrial cancer, lung cancer, liver cancer, kidney cancer, neuroblastoma, glioma, breast cancer, melanoma, prostate cancer, bladder cancer, pancreatic cancer, gastric cancer, colorectal cancer, esophageal cancer, thyroid cancer, laryngeal cancer, osteosarcoma, hematopoietic malignancy (e.g., lymphoma or leukemia).

Modified EV-D68

In a fourth aspect, the present invention provides a modified EV-D68 having a substitution, insertion, or deletion of one or more nucleotides in the genome compared to wild-type EV-D68.

In certain preferred embodiments, the genomic sequence of the wild-type EV-D68 has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence selected from the nucleotide sequence as shown in SEQ ID NO: 12. In certain preferred embodiments, the genomic sequence of the wild-type EV-D68 is a nucleotide sequence as shown in SEQ ID NO: 12.

In certain preferred embodiments, the cDNA sequence of the wild-type EV-D68 has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence as shown in SEQ ID NO: 1. In certain preferred embodiments, the cDNA sequence of the wild-type EV-D68 is a nucleotide sequence as shown in SEQ ID NO: 1.

In certain preferred embodiments, as compared to the wild-type EV-D68, the modified EV-D68 has one or more modifications selected from the following:

(1) one or more mutations in an untranslated region (e.g., 5'UTR or 3'UTR);

(2) an insertion of one or more exogenous nucleic acids;

(3) a deletion or mutation of one or more endogenous genes; and (4) any combination of the above three items.

In certain preferred embodiments, the modified EV-D68 includes one or more mutations in the 5' untranslated region (5'UTR).

In certain preferred embodiments, the modified EV-D68 has a substitution of all or part of the 5'UTR sequence. In certain preferred embodiments, the internal ribosome entry site (IRES) sequence in the 5'UTR of the modified EV-D68 is replaced with an exogenous IRES sequence, such as the interior ribosome entry site sequence of human rhinovirus 2 (HRV2). In certain preferred embodiments, the internal ribosome entry site sequence of the human rhinovirus 2 (HRV2) is shown in SEQ ID NO: 2.

In certain preferred embodiments, the modified EV-D68 comprises an exogenous nucleic acid.

In certain preferred embodiments, the exogenous nucleic acid encodes a cytokine (e.g., a GM-CSF, preferably a human GM-CSF), or an antitumor protein or polypeptide (e.g., a scFv against PD-1 or PD-L1, preferably a scFv against human PD-1 or PD-L1) In certain preferred embodiments, the exogenous nucleic acid is inserted between the 5'UTR gene and the VP4 gene, or between the VP1 gene and the 2A gene of the genome of the modified EV-D68.

In certain preferred embodiments, the exogenous nucleic acid comprises a target sequence of microRNA (miRNA) (e.g., miR-133 or miR-206) In certain preferred embodiments, the target sequence of microRNA is inserted in the 3' untranslated region (3'UTR) of the genome of the modified EV-D68.

In certain preferred embodiments, the exogenous nucleic acid comprises a target sequence of one or more (e.g., 2, 3, or 4) microRNA as described above. In certain preferred embodiments, the exogenous nucleic acid comprises a target sequence of miR-133 and/or miR-206. In certain preferred embodiments, the target sequence of miR-133 is shown in SEQ ID NO: 3. In certain preferred embodiments, the target sequence of miR-206 is shown in SEQ ID NO: 4.

In certain preferred embodiments, the modified EV-D68 comprises at least one insertion of the exogenous nucleic acid as described above and/or at least one mutation in the untranslated region as described above.

In certain preferred embodiments, the genomic sequence of the modified EV-D68 has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence selected from: the nucleotide sequences as shown in SEQ ID NOs: 13-16. In certain preferred embodiments, the genomic sequence of the modified EV-D68 is selected from the nucleotide sequences as shown in any one of SEQ ID NOs: 13-16.

In certain preferred embodiments, the cDNA sequence of the modified EV-D68 has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence selected from: the nucleotide sequences as shown in SEQ ID NOs: 8-11. In certain preferred embodiments, the cDNA sequence of the modified EV-D68 is selected from the nucleotide sequences as shown in any one of SEQ ID NOs: 8-11.

In the present invention, the modified EV-D68 can be obtained by reverse genetics technology, and the reverse genetics technology is known in the art, for example, see Yang L S, Li S X, Liu Y J, et al Virus Res, 2015, 210: 165-168; Hou W H, Yang L S, Li S X, et al. Virus Res, 2015, 205: 41-44; which are incorporated herein by reference in their entirety. In such embodiments, the modified EV-D68 is typically obtained by modifying the cDNA of wild-type EV-D68 (e.g., insertion of an exogenous nucleic acid, deletion or mutation of an endogenous gene, or mutation in a non-translated region).

In the present invention, the modified EV-D68 may be pretreated to reduce or eliminate the immune response against the virus in a subject, wherein the pretreatment may comprise: packaging the EV-D68 in a lipidosome or micelle, and/or using a protease (e.g., chymotrypsin or trypsin) to remove the capsid protein of the virus to reduce the humoral and/or cellular immunity against the virus in host.

In the present invention, the modified EV-D68 can be serially passaged for adaptation in tumor cells. In certain preferred embodiments, the tumor cells may be tumor cell lines or tumor cell strains known in the art, or may be tumor cells obtained by surgical resection or clinical isolation from an individual (e.g., a subject) having a tumor. In certain preferred embodiments, the modified EV-D68 is serially passaged for adaptation in tumor cells obtained from an individual (e.g., a subject) having a tumor. In certain preferred embodiments, the tumor cells are obtained by surgical resection or clinical isolation from an individual (e.g., a subject) having a tumor. In certain preferred embodiments, the method for serial passaging for adaptation comprises a plurality of (e.g., at least 5, at least 10, at least 15, at least 20) cycles consisting of the following processes: 1) infecting a target tumor cell with a virus; 2) harvesting the virus in a supernatant; and 3) reinfecting a fresh target tumor cell with the obtained virus.

In certain preferred embodiments, the modified EV-D68 is used to treat a tumor in a subject, or to prepare a medicament for treating a tumor in a subject.

In certain preferred embodiments, the tumor includes, but is not limited to, cervical cancer, ovarian cancer, endometrial cancer, lung cancer, liver cancer, kidney cancer, neuroblastoma, glioma, breast cancer, melanoma, Prostate cancer, bladder cancer, pancreatic cancer, gastric cancer, colorectal cancer, esophageal cancer, thyroid cancer, laryngeal cancer, osteosarcoma, hematopoietic malignancy (such as lymphoma or leukemia).

In certain preferred embodiments, the subject is a mammal, such as a human.

In certain preferred embodiments, the modified EV-D68 of the present invention has the internal ribosome entry site (IRES) sequence in the 5'UTR replaced with the internal ribosome entry site sequence of human rhinovirus 2 (HRV2) compared to wild type EV-D68.

In certain preferred embodiments, the modified EV-D68 further comprises an exogenous nucleic acid.

In certain preferred embodiments, the exogenous nucleic acid encodes a cytokine (eg, GM-CSF, preferably human GM-CSF), or an antitumor protein or polypeptide (e.g., a scFv against PD-1 or PD-L1, preferably a scFv against human PD-1 or PD-L1). In certain preferred embodiments, the exogenous nucleic acid is inserted between the 5'UTR and the VP4 gene, or between the VP1 gene and the 2A gene of the genome of the modified EV-D68.

In certain preferred embodiments, the exogenous nucleic acid comprises a target sequence of microRNA (microRNA, miRNA) (eg, miR-133 or miR-206). In certain preferred embodiments, the target sequence of the microRNA is inserted in the 3' untranslated region (3'UTR) of the genome of the modified EV-D68.

In certain preferred embodiments, the exogenous nucleic acid includes a target sequence of one or more (e.g., two, three, or four) microRNAs as described above. In certain preferred embodiments, the exogenous nucleic acid comprises a target sequence of miR-133 and/or miR-206. In certain preferred embodiments, the target sequence of the miR-133 is shown in SEQ ID NO: 3. In certain preferred embodiments, the target sequence of the miR-206 is shown in SEQ ID NO: 4.

In certain preferred embodiments, the modified EV-D68 comprises an insertion of at least one exogenous nucleic acid as described above.

In certain preferred embodiments, the genomic sequence of the modified EV-D68 has at least 70%, at least 80%, at least 85%, at least 90%, at least 91%, at least 92%, at least 93%, at least 94%, at least 95%, at least 96%, at least 97%, at least 98%, at least 99%, or 100% sequence identity to the nucleotide sequence shown in SEQ ID NO: 13. In certain preferred embodiments, the genomic sequence of the modified EV-D68 is a nucleotide sequence as shown in SEQ ID NO: 1:3.

In certain preferred embodiments, the cDNA sequence of the modified EV-D68 has at least 70%, at least 80%, at least 85%, at least 90%, at least 91%, at least 92%, at least 93%, at least 94%, at least 95%, at least 96%, at least 97%, at least 98%, at least 99%, or 100% sequence identity to the nucleotide sequence shown in SEQ ID NO: 8. In certain preferred embodiments, the cDNA sequence of the modified EV-D68 is a nucleotide sequence as shown in SEQ ID NO: 8.

In certain preferred embodiments, the modified EV-D68 is used to treat a tumor in a subject.

In certain preferred embodiments, the tumor includes, but is not limited to, cervical cancer, ovarian cancer, endometrial cancer, lung cancer, liver cancer, kidney cancer, neuroblastoma, glioma, breast cancer, melanoma, prostate cancer, bladder cancer, pancreatic cancer, gastric cancer, colorectal cancer, esophageal cancer, thyroid cancer, laryngeal cancer, osteosarcoma, hematopoietic malignancy (such as lymphoma or leukemia).

In certain preferred embodiments, the tumor is selected from the group consisting of gastric cancer, endometrial cancer, cervical cancer, and thyroid cancer.

In a fifth aspect, the invention provides an isolated nucleic acid molecule comprising a sequence selected from:

(1) the genomic sequence or cDNA sequence of the modified EV-D68 according to the fourth aspect; and (2) a complementary sequence of the genomic sequence or cDNA sequence.

In certain preferred embodiments, the isolated nucleic acid molecule consists of the genomic sequence or cDNA sequence of the modified EV-D68 as described above, or the complementary sequence of the genomic sequence or cDNA sequence.

In certain preferred embodiments, the isolated nucleic acid molecule has the genomic sequence of the modified EV-D68 as described above. In certain preferred embodiments, the isolated nucleic acid molecule is RNA. In certain preferred embodiments, the isolated nucleic acid molecule has the nucleotide sequence as shown in any one of SEQ ID NOs: 12-16.

In certain preferred embodiments, the isolated nucleic acid molecule is a vector (e.g. a cloning vector or an expression vector) comprising a genomic sequence or cDNA sequence of EV-D68 or a modified form thereof as described above, or a complementary sequence of the genomic sequence or cDNA sequence. In certain preferred embodiments, the isolated nucleic acid molecule is a vector (e.g., a cloning vector or an expression vector) comprising a cDNA sequence of EV-D68 or a modified form thereof as described above, or a complementary sequence of the cDNA sequence. In certain preferred embodiments, the isolated nucleic acid molecule is a vector (e.g., a cloning vector or an expression vector) comprising a nucleotide sequence as shown in any one of SEQ ID NOs: 1, 8-11 or a complementary sequence thereof.

In certain preferred embodiments, the isolated nucleic acid molecule comprises a complementary sequence of the genomic sequence of the modified EV-D68 as described above. In certain preferred embodiments, the complementary sequence is complementary to a nucleotide sequence selected from:

(1) a nucleotide sequence as shown in any one of SEQ ID NOs: 13-16; and (2) a nucleotide sequence having a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence as shown in any one of SEQ ID NOs: 13-16.

In certain preferred embodiments, the isolated nucleic acid molecule comprises the complementary sequence of the cDNA sequence of the modified EV-D68 as described above. In certain preferred embodiments, the complementary sequence is complementary to a nucleotide sequence selected from:

(1) a nucleotide sequence as shown in any one of SEQ ID NOs: 8-11; and (2) a nucleotide sequence having a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence as shown in any one of SEQ ID NOs: 8-11.

In certain preferred embodiments, the isolated nucleic acid molecule has a nucleotide sequence as shown in SEQ ID NO: 13, or the isolated nucleic acid molecule is a vector (e.g., a cloning vector or an expression vector) comprising a nucleotide sequence as shown in SEQ ID NO: 8 or a complementary sequence thereof.

In the present invention, the isolated nucleic acid molecule can be delivered by any means known in the art, for example, a naked nucleic acid molecule (e.g., naked RNA) can be directly injected, or a non-viral delivery system can be used. The non-viral delivery system can be obtained from a variety of materials well known in the art, including, but not limited to, the materials described in detail in "Yin H, et al. Nat Rev Genet. 2014 August; 15 (8): 541-55," and "Riley M K, Vermerris W. Nanomaterials (Base1). 2017 Apr. 28; 7(5). Pii: E94.", which are incorporated herein by reference in their entirety, such as liposomes, inorganic nanoparticles (such as gold nanoparticles), polymers (such as PEG), and so on.

In certain preferred embodiments, the isolated nucleic acid molecule is used to treat a tumor in a subject, or to prepare a medicament for treating a tumor in a subject.

In certain preferred embodiments, the tumor includes, but is not limited to, cervical cancer, ovarian cancer, endometrial cancer, lung cancer, liver cancer, kidney cancer, neuroblastoma, glioma, breast cancer, melanoma, prostate cancer, bladder cancer, pancreatic cancer, gastric cancer, colorectal cancer, esophageal cancer, thyroid cancer, laryngeal cancer, osteosarcoma, hematopoietic malignancy (such as lymphoma or leukemia).

In certain preferred embodiments, the subject is a mammal, such as a human.

In another aspect, the present invention also relates to a pharmaceutical composition comprising the modified EV-D68 according to the fourth aspect, or the isolated nucleic acid molecule according to the fifth aspect.

In another aspect, the present invention also relates to use of the modified EV-D68 according to the fourth aspect, or the isolated nucleic acid molecule according to the fifth aspect, in treating a tumor in a subject, or in the manufacture of a medicament for treating a tumor in a subject.

In another aspect, the invention also relates to a method for treating a tumor, comprising a step of administering to a subject in need thereof an effective amount of the modified EV-D68 as described in the fourth aspect, or the isolated nucleic acid molecule according to the fifth aspect Definition of Terms In the present invention, unless otherwise stated, scientific and technical terms used herein have meanings commonly understood by those skilled in the art. In addition, the laboratory procedures of cell culture, biochemistry, cell biology, nucleic acid chemistry and the like used herein are all routine steps widely used in the corresponding fields. Meanwhile, in order to better understand the present invention, definitions and explanations of related terms are provided below.

As used herein, the term "enterovirus D68 (EV-D68)" refers to one kind of Enterovirus D of the genus Enteroviruses of Picornaviridae family, the genome of which is a single-stranded positive-sense RNA, consisting of a 5' non-coding region (5'UTR), an open reading frame (ORF), a 3' non-coding region (3'UTR), and a poly(A) tail; wherein its ORF encodes a precursor polyprotein, which can be hydrolyzed and cleaved by its protease to produce structural proteins VP1 to VP4 and non-structural proteins 2A, 2B, 2C, 3A, 3B, 3C and 3D. In order to more clearly describe the present invention, the nucleic acid sequences in the EV-D68 genome corresponding to the above proteins are called VP1 gene, VP2 gene, VP3 gene, VP4 gene, 2A gene, 2B gene, 2C gene, 3A gene, 3B gene, 3C gene, and 3D gene, respectively. In the present invention, the expression "enterovirus D68 (EV-D68)" refers to a wild-type EV-D68, which can be isolated from sources in nature and has not been intentionally modified artificially, examples of which include, but are not limited to, prototype strains AY426531 (CA62-1) and AY426488 (CA62-3), and various clinical isolates (for example, the clinical isolate described in Example 1 of the present invention). The genomic sequence or cDNA sequence of the wild-type EV-D68 is well known in the art and can be found in various public databases (for example, GenBank database, accession number KM881710).

As used herein, the term "modified form" of a virus refers to a modified virus obtained by modifying a wild-type virus, which retains the desired activity (e.g., oncolytic activity) of the wild-type virus. In the present invention, a "modified form" of EV-D68 includes, but is not limited to, a modified EV-D68 virus, the genome sequence of which has a substitution, insertion, or deletion of one or more nucleotides as compared to that of the wild-type EV-D68, and at least retains the oncolytic activity of EV-D68.

As used herein, the term "oncolytic virus" refers to a virus capable of infecting a tumor cell, replicating in the tumor cell, causing the tumor cell death, lysis, or blocking tumor cell growth. Preferably, the virus has minimal toxic effects on a non-tumor cell.

As used herein, the term "tumor-specific" refers to selectively exhibiting a biological function or activity within a tumor cell. For example, in the present invention, when the term "tumor specificity" is used to describe the killing selectivity of a virus, it means that the virus can selectively kill a tumor cell without killing or substantially killing a non-tumor cell, or the virus is more effective in killing a tumor cell than killing a non-tumor cell.

As used herein, the term "oncolytic activity" primarily includes tumor killing activity. When describing the oncolytic activity of a virus, the oncolytic activity of the virus can typically be measured by indicators such as the virus' ability to infect a tumor cell, ability to replicate in a tumor cell, and/or ability to kill a tumor cell. The oncolytic activity of a virus can be measured using any method known in the art. For example, the ability of a virus to infect a tumor cell can be evaluated by measuring the viral dose required to infect a given percentage of tumor cells (for example, 50% of the cells); the ability to replicate in a tumor cell can be evaluated by measuring the growth of the virus in the tumor cell; the ability to kill a tumor cell can be evaluated by monitoring cytopathic effect (CPE) or measuring tumor cell activity.

As used herein, the expression "cDNA sequence of EV-D68" means the DNA form of the viral genomic RNA sequence, which differs from the RNA sequence only in that the ribonucleotides in the RNA sequence are replaced by corresponding deoxyribonucleotides, for example, uracil ribonucleotides (UMP) are replaced by thymine deoxyribonucleotides (dTMP).

As used herein, the term "exogenous nucleic acid" refers to an artificially introduced nucleotide sequence that is foreign to the original sequence. Exogenous nucleic acid includes, but is not limited to, any gene or nucleotide sequence not found in the viral genome. However, in the present invention, it is particularly preferred that the exogenous nucleic acid is composed of at most 1500, such as at most 1200, and at most 1000 nucleotides. In some cases, preferably, the exogenous nucleic acid encodes a protein or polypeptide having antitumor killing activity, such as a cytokine, or an antitumor protein or polypeptide; or, the exogenous nucleic acid comprises a target sequence of microRNA (miRNA). In the present invention, the microRNA is preferably a microRNA having an expression level in a tumor cell significantly lower than that in a normal cell and/or having obvious tissue specificity. Examples of the microRNA include, but are not limited to, miR-122, miR-192, miR-483, etc., which are specifically expressed in liver tissue; miR-1, miR-133a/b, miR-208, etc., which are specifically expressed in heart; miR-192, miR-196a/b, miR-204, miR-215, etc., which are specifically expressed in kidney tissue; miR-133a/b, miR-206, etc., which are specifically expressed in muscle tissue; miR-124a, miR-125a/b, miR-128a/b, miR-138, etc., which are specifically expressed in brain tissue; and miR-34, miR-122a, miR-26a, which are under-expressed in liver tumor tissue; miR-34, which is 1 under-expressed in kidney tumor tissue; miR-143, miR-133a/b, which are under-expressed in bladder tumor tissue; miR-Let-7, miR-29, which are under-expressed in lung tumor tissue; and so on (see, for example, Ruiz A J and Russell S J. MicroRNAs and oncolytic viruses. [J]. Curr Opin Virol, 2015, 13: 40-48; which is incorporated herein by reference in its entirety).

In the present invention, when the modified EV-D68 comprises the target sequence of microRNA described above, it is regulated by the microRNA in a cell/tissue in which the microRNA is highly expressed or specifically expressed, so that replication of the oncolytic virus is attenuated and even its killing activity is lost, while in a tumor cell/tissue in which the microRNA is under-expressed or even not expressed, the oncolytic virus can normally replicate and thus kill the tumor cell.

As used herein, the term "cytokine" has a meaning well known to those skilled in the art. However, in the present invention, when the oncolytic virus of the present invention is used to treat a tumor, it is particularly preferred that the cytokine is a cytokine that can be used for tumor treatment. Examples of "cytokines" include, but are not limited to, interleukins (e.g., IL-2, IL-12, and IL-15), interferons (e.g., IFNα, IFNβ, IFNγ), tumor necrosis factors (e.g., TNFα), and colony-stimulating factors (e.g., GM-CSF), and any combination thereof (see, for example, Ardolino M, Hsu J, Raulet D H. Cytokine treatment in cancer immunotherapy [J]. Oncotarget, 2015, 6 (23): 19346-19347).

As used herein, the term "antitumor protein or polypeptide" refers to a protein or polypeptide having antineoplastic activity, including but not limited to: (1) proteins or polypeptides having toxicity to cells, capable of inhibiting cell proliferation, or inducing apoptosis, examples thereof include, but are not limited to, thymidine kinase TK (TK/GCV), TRAIL, and FasL (see, for example, Candolfi M, King G D, Muhammad A G, et al. Evaluation of proapototic transgenes to use in combination with Flt3L in an immune-stimulatory gene therapy approach for Glioblastoma multiforme (GBM) [J]. FASEB J, 2008, 22: 1077.13); (2) proteins or polypeptides having immunotherapeutic effects, examples thereof include, but are not limited to, single chain antibody (scFv) against cytotoxic T lymphocyte-associated antigen 4 (anti-CTLA-4), against programmed death receptor 1 (anti-PD-1), and against programmed death ligand 1 (anti-PDL-1) (see, for example, Nolan E, Savas P, Policheni A N, et al. Combined immune checkpoint blockade as a therapeutic strategy for BRCA1-mutated breast cancer [J]. Science Trans Med, 2017, 9: eaal 4922; which is incorporated herein by reference in its entirety); (3) proteins or polypeptides that inhibit tumor angiogenesis, examples thereof include, but are not limited to, single-chain antibody (scFv) against vascular endothelial growth factor (anti-VEGF), VEGF-derived polypeptides (e.g., $_D$(LPR), KSVRGKGKGQKRKRKKSRYK, etc.) and ATN-161 (see, for example, Rosca E V, Koskimaki J E, Rivera C G, et al. Anti-angiogenic peptides for cancer therapeutics [J]. Curr Pharm Biotechnol, 2011, 12 (8): 1101-1116; which is incorporated herein by reference in its entirety).

As used herein, the term "scFv" refers to a single polypeptide chain comprising a heavy chain variable region (VH) and a light chain variable region (VL), wherein the VL and VH are linked by a linker (see, for example, Bird et al., Science 242: 423-426 (1988); Huston et al., Proc. Natl. Acad. Sci. USA 85: 5879-5883 (1988); and Pluckthun, The Pharmacology of Monoclonal Antibodies, No. Volume 113, edited by Roseburg and Moore, Springer-Verlag, New York, pp. 269-315 (1994)). Such scFv molecule may have a general structure: $NH_2$-VL-linker-VH-COOH or $NH_2$-VH-linker-VL-COOH.

As used herein, the term "identity" refers to the match degree between two polypeptides or between two nucleic acids. When two sequences for comparison have the same monomer sub-unit of base or amino acid at a certain site (e.g., each of two DNA molecules has an adenine at a certain site, or each of two proteins/polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by for example using a computer program such as Align program (DNAstar, Inc.) which is based on the method of Needleman, et al. (J. Mol. Biol. 48:443-453, 1970). The percentage of identity between two amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, and with a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and with a gap weight of 16, 14, 12, 10, 8, 6, or 4 and a length weight of 1, 2, 3, 4, 5, or 6.

As used herein, the term "vector" refers to a nucleic acid vehicle into which a polynucleotide can be inserted. When a vector enables expression of a protein encoded by an inserted polynucleotide, the vector is referred to as an expression vector. A vector can be introduced into a host cell by transformation, transduction, or transfection, so that the genetic material elements carried by the vector can be expressed in the host cell. The vector is well known to those skilled in the art and includes, but is not limited to: plasmids; phagemids; cosmids; artificial chromosomes, such as yeast artificial chromosomes (YAC), bacterial artificial chromosomes (BAC) or P1-derived artificial chromosomes (PAC); bacteriophages such as λ-phage or M13 phage and animal viruses. Animal viruses that can be used as vectors include, but are not limited to, retroviruses (including lentiviruses), adenoviruses, adeno-associated viruses, herpesviruses (such as herpes simplex virus), poxviruses, baculoviruses, papillomaviruses, and papovaviruses (such as SV40). A vector may contain a variety of elements that control expression, including, but not limited to, promoter sequences, transcription initiation sequences, enhancer sequences, elements for selection, and reporter genes. In addition, the vector may contain a replication initiation site.

As used herein, the term "internal ribosome entry site (IRES)" refers to a nucleotide sequence located in a messenger RNA (mRNA) sequence that is capable of initiating translation without the need for the 5' cap structure. IRES is usually located in the 5' untranslated region (5'UTR), but may also be located elsewhere in the mRNA.

As used herein, the term "human rhinovirus 2 (HRV2)" refers to a virus of picornaviridae family, the genomic or cDNA sequence of which is well known in the art and can be found in various public databases (e.g., GenBank database, accession number X02316.1).

As used herein, the expression "a nucleic acid molecule comprising a genomic sequence of EV-D68 or a modified form thereof" or "a nucleic acid molecule comprises a genomic sequence of EV-D68 or a modified form thereof" has the meaning commonly understood by those skilled in the art, that is, when the nucleic acid molecule is DNA, the nucleic acid molecule comprises a genomic sequence of EV-D68 or a modified form thereof in form of DNA; when the nucleic acid molecule is RNA, the nucleic acid molecule comprises a genomic sequence of EV-D68 or a modified form thereof.

As used herein, the term "pharmaceutically acceptable carrier and/or excipient" refers to a carrier and/or excipient that is pharmacologically and/or physiologically compatible with the subject and the active ingredient, which is well known in the art (see, for example, Remington's Pharmaceutical Sciences. Edited by Gennaro A R, 19th ed. Pennsylvania: Mack Publishing Company, 1995), and includes, but is not limited to: pH adjusting agents, surfactants, ionic strength enhancers, agents to maintain osmotic pressure, agents to delay absorption, diluents, adjuvants, preservatives, stabilizers, etc. For example, pH adjusting agents include, but are not limited to, phosphate buffered saline. Surfactants include, but are not limited to, cationic, anionic or non-ionic surfactants, such as Tween-80. Ionic strength enhancers include, but are not limited to, sodium chloride. Agents that maintain osmotic pressure include, but are not limited to, sugar, NaCl, and the like. Agents that delay absorption include, but are not limited to, monostearate and gelatin. Diluents include, but are not limited to, water, aqueous buffers (such as buffered saline), alcohols and polyols (such as glycerol), and the like. Adjuvants include, but are not limited to, aluminum adjuvants (such as aluminum hydroxide), Freund's adjuvants (such as complete Freund's adjuvant), and the like. Preservatives include, but are not limited to, various antibacterial and antifungal agents, such as thimerosal, 2-phenoxyethanol, parabens, trichloro-t-butanol, phenol, sorbic acid, and the like. Stabilizers have the meaning commonly understood by those skilled in the art, which can stabilize the desired activity (such as oncolytic activity) of the active ingredients in the drug, including but not limited to sodium glutamate, gelatin, SPGA, sugars (e.g., sorbitol, mannitol, starch, sucrose, lactose, dextran, or glucose), amino acids (e.g., glutamic acid, glycine), proteins (e.g., dried whey, albumin, or casein) or their degradation products (e.g., lactalbumin hydrolysates).

As used herein, the term "treating" refers to treating or curing a disease (e.g., a tumor), delaying the onset of symptoms of a disease (e.g., a tumor), and/or delaying the development of a disease (e.g., a tumor).

As used herein, the term "effective amount" refers to an amount that can effectively achieve the intended purpose. For example, a therapeutically effective amount can be an amount effective or sufficient to treat or cure a disease (e.g., a tumor), delay the onset of symptoms of a disease (e.g., a tumor), and/or delay the development of a disease (e.g., a tumor). Such an effective amount can be easily determined by a person skilled in the art or a doctor, and can be related to the intended purpose (such as treatment), the general health condition, age, gender, weight of the subject, severity, complications, administration route of the disease to be treated. The determination of such an effective amount is well within the capabilities of those skilled in the art.

As used herein, the term "subject" refers to a mammal, such as a primate mammal, such as a human. In certain embodiments, the subject (e.g., a human) has a tumor, or is at risk for having a tumor.

The Beneficial Effects of the Present Invention

Compared with the prior art, the technical solution of the present invention has at least the following beneficial effects:

The inventors of the present application have found for the first time that enterovirus D68 (EV-D68) has broad-spectrum tumor-killing activity. Based on this finding, the present invention further provides an EV-D68-based oncolytic virus, which has a broader-spectrum tumor-killing activity and higher tumor specificity, especially also has a very high killing effect to hematopoietic malignancy (such as lymphoma or leukemia), thus can be used alone for the treatment of tumors, and can also be used as a supplementary method of traditional tumor treatment, or as a treatment in the absence of other treatment methods.

The EV-D68 or a modified form thereof of the present invention has little or no effect on normal cells, and does not induce an immunogenic response against the virus in a subject (for example, a human), and thus can be safely administered to a subject (for example, a human). Therefore, the EV-D68 or a modified form thereof of the present invention has great clinical value.

The embodiments of the present invention will be described in detail below with reference to the drawings and examples, but those skilled in the art will understand that the following drawings and examples are only used to illustrate the present invention, rather than limiting the scope of the present invention. Various objects and advantageous aspects of the present invention will become apparent to those skilled in the art from the following detailed description of drawings and the preferred embodiments.

growth of tumors formed by subcutaneous inoculation of Hela, U118-MG, or Raji cells in SCID mice significantly slowed down and arrested, and the tumors were even lysed and disappeared. In contrast, the tumors of the negative group (CTRL) without treatment of oncolytic virus maintained the normal growth, and their tumor volumes are significantly larger than those in the challenge group.

Figure 6A:
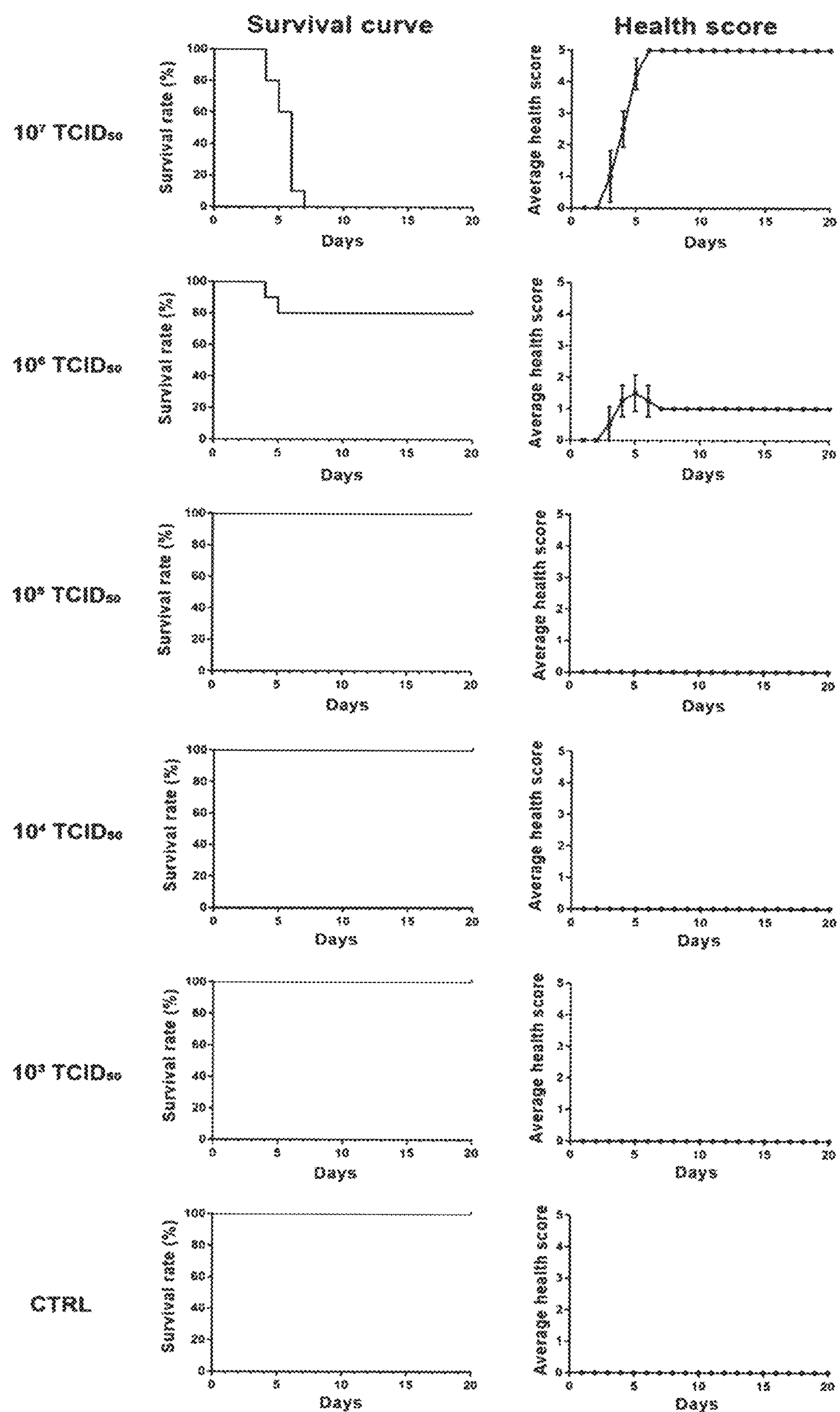
Figure 6B:
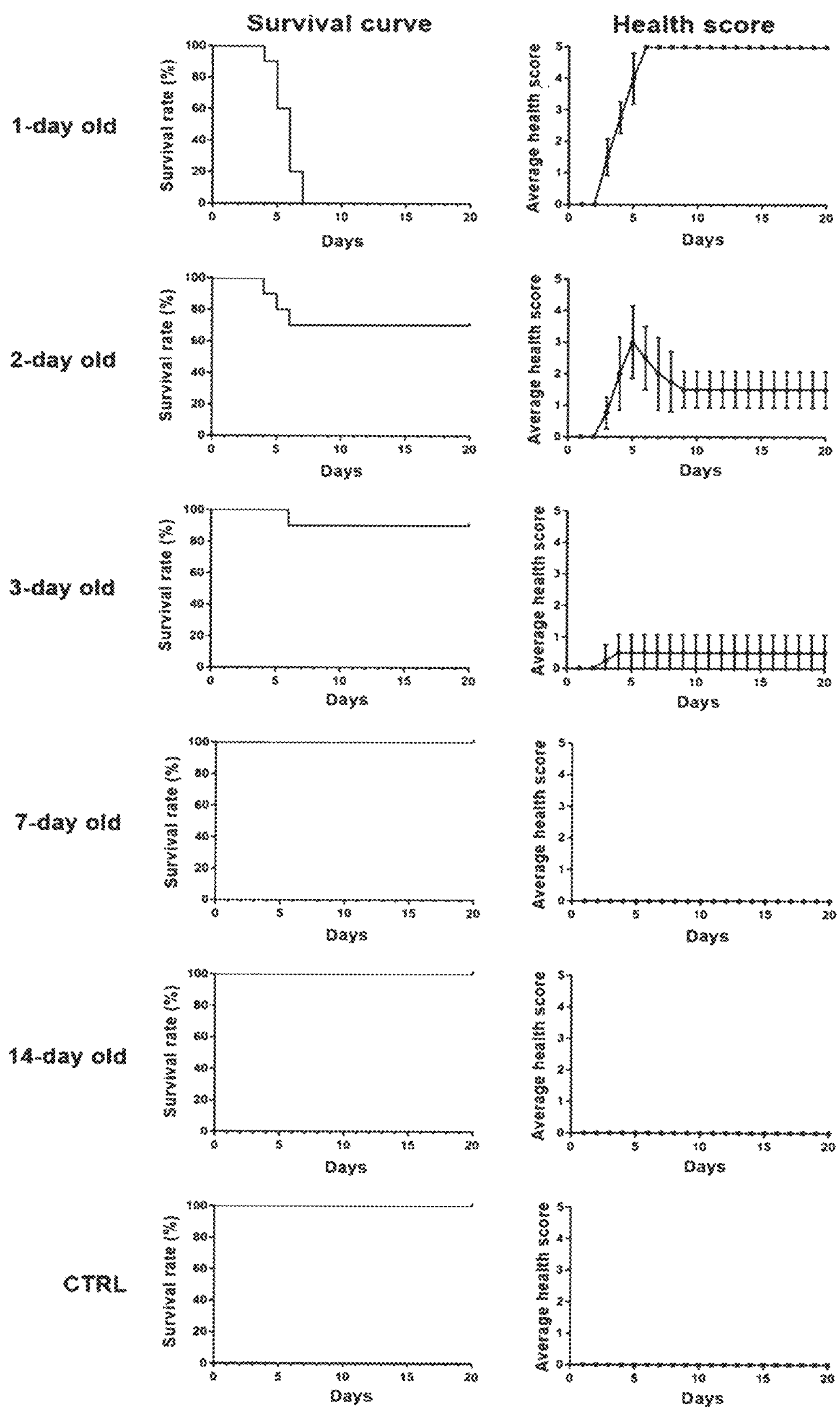

FIG. 6 shows the results of toxicity detection of EV-D68-WT in BALB/c mice in Example 4. FIG. 6A shows the survival rates and health scores of 1-day-old BALB/c mice after challenge with EV-D68 at different doses ($10^3$, $10^4$, $10^5$, $10^6$, and $10^7$ TCID50/mouse) by intraperitoneal injection; FIG. 6B shows the survival rates and health scores of BALB/c mice of different ages (1-day-old, 2-day-old, 3-day-old, 7-day-old and 14-day-old) challenged with a very high dose ($10^7$ TCID50/mouse) by intraperitoneal injection. The overall toxicity of EV-D68 to BALB/c mice was relatively weak, and only high doses caused the death of 1-day-old to 3-day-old BALB/c mice, but had no effect on 4- or more-day-old BALB/c mice, indicating that EV-D68 had good safety in vivo.

SEQUENCE INFORMATION

Information of a part of sequences involved in the present invention is provided in Table 1 as below.

TABLE 1

Sequence description

| SEQ ID NO: | Description |
|---|---|
| 1 | cDNA sequence of wild type EV-D68 (EV-D68-WT) |
| 2 | RNA sequence of the internal ribosome entry site of human rhinovirus 2 (HRV2) |
| 3 | RNA sequence of the target sequence of miR-133 |
| 4 | RNA sequence of the target sequence of miR-206 |
| 5 | RNA sequence of tandem sequence of miR-133 target sequence and miR-206 target sequence |
| 6 | DNA sequence of human granulocyte-macrophage colony-stimulating factor (GM-CSF) gene |
| 7 | DNA sequence of anti-human programmed death receptor 1 single chain antibody (Anti-PD-1 scFv) |
| 8 | cDNA sequence of the modified form of EV-D68 (EV-D68-HRV2) |
| 9 | cDNA sequence of the modified form of EV-D68 (EV-D68-miR133&206T) |
| 10 | cDNA sequence of the modified form of EV-D68 (EV-D68-GM-CSF) |
| 11 | cDNA sequence of the modified form of EV-D68 (EV-D68-Anti-PD1) |
| 12 | Genomic sequence of wild-type EV-D68 (EV-D68-WT) |
| 13 | Genomic sequence of the modified form of EV-D68 (EV-D68-HRV2) |
| 14 | Genomic sequence of the modified form of EV-D68 (EV-D68-miR133 & 206T) |
| 15 | Genomic sequence of the modified form of EV-D68 (EV-D68-GM-CSF) |
| 16 | Genomic sequence of the modified form of EV-D68 (EV-D68-Anti-PD1) |
| 17 | DNA sequence of miR-133 target sequence |
| 18 | DNA sequence of miR-206 target sequence |
| 19 | DNA sequence of tandem sequence of miR-133 target sequence and miR-206 target sequence |
| 20 | DNA sequence of the internal ribosome entry site sequence of human rhinovirus 2 (HRV2) |

Figure 4:
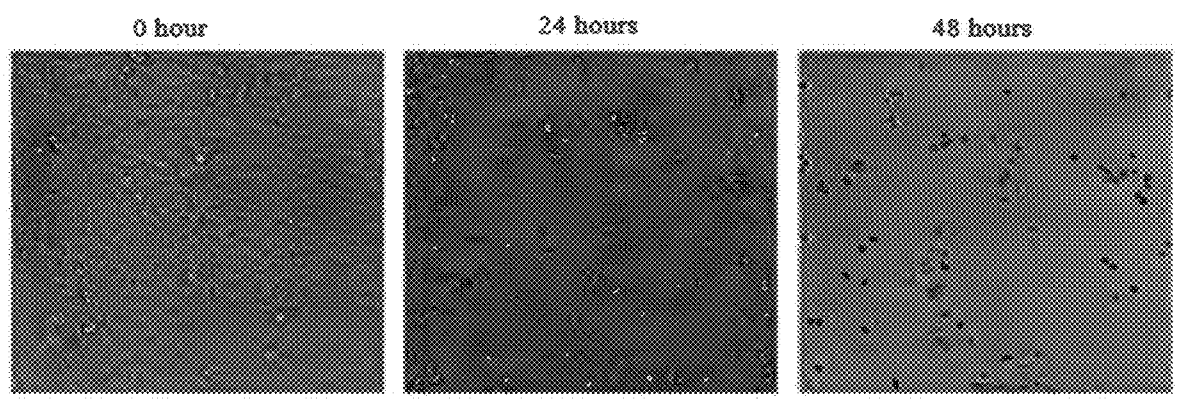

FIG. 4 shows the killing effect of the wild-type EV-D68 virus genomic RNA on human cervical cancer tumor cell line Hela in Example 2. The results showed that Hela cells showed obvious CPE after 24 hours of transfection with EV-D68 genomic RNA, and were almost all lysed to death by 48 hours.

Figure 5A:
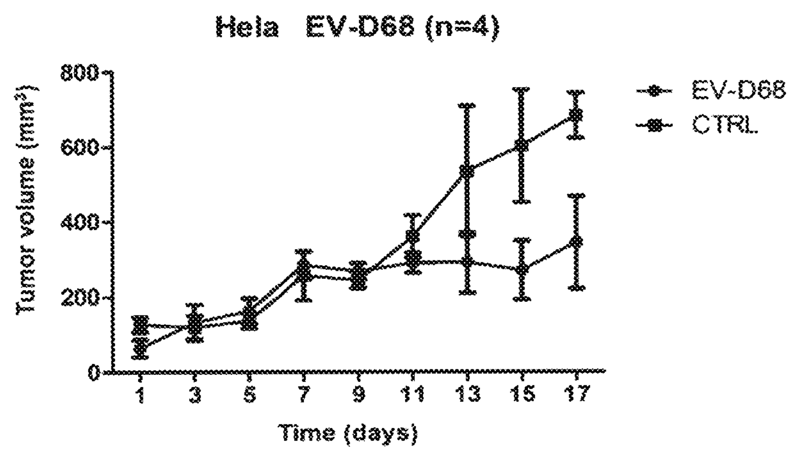
Figure 5B:
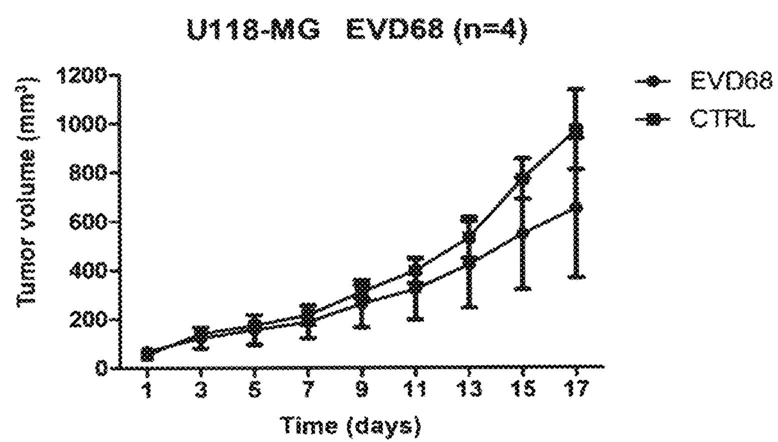
Figure 5C:
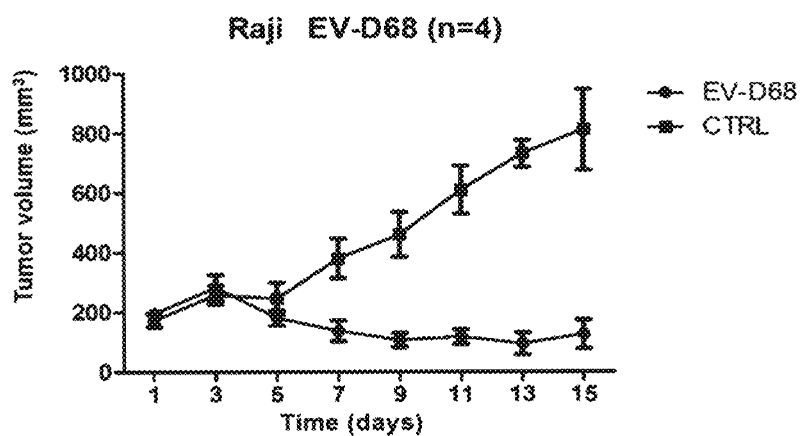

FIGS. 5A to 5C show the results of in vivo antitumor experiment of the wild-type EV-D68 in Example 3 on human cervical cancer cell line Hela (A), human glioma cell line U118-MG (B), and human lymphoma cell line Raji (C). The results showed that, in the challenge experimental group, $10^6$ TCID50 per tumor mass of EV-D68 were injected intratumorally every third day. After 5 treatments in total, the

SPECIFIC MODELS FOR CARRYING OUT THE INVENTION

The present invention is now be described with reference to the following examples which are intended to illustrate the present invention (rather than to limit the present invention).

Unless otherwise specified, the molecular biology experimental methods and immunoassays used in the present invention were carried out substantially by referring to the methods described in J. Sambrook et al., Molecular Cloning: A Laboratory Manual, 2nd Edition, Cold Spring Harbor Laboratory Press, 1989, and F. M. Ausubel et al., Short Protocols in Molecular Biology, 3rd Edition, John Wiley & Sons, Inc., 1995; restriction enzymes were used under conditions recommended by the product manufacturer. If the specific conditions were not indicated in the examples, the conventional conditions or the conditions recommended by the manufacturer were used. If the reagents or instruments used were not specified by the manufacturer, they were all conventional products that were commercially available. Those skilled in the art will understand that the examples describe the present invention by way of examples, and are not intended to limit the scope of protection claimed by the present invention. All publications and other references mentioned herein are incorporated by reference in their entirety.

Example 1: Obtainment and Preparation of EV-1368 and its Modified Form 1.1 Isolation of Enterovirus EV-D68 from Patient Clinical Sample (1) A throat swab of patient was gained from the Center for Disease Control and Prevention of Xiamen City, China; African green monkey kidney cells (Vero cells; ATCC® Number: CCL-81™) were was kept by the National Institute of Diagnostics and Vaccine Development in Infectious Diseases, Xiamen University, China, and cultured in MEM medium containing 10% fetal bovine serum, as well as glutamine, penicillin and streptomycin.

(2) Sample processing: the throat swab of patient was sufficiently agitated in a sample preservation solution to wash off the virus and virus-containing cells adhering to the swab, and then the sample preservation solution was subjected to a high speed centrifugation at 4000 rpm and 4° C. for 30 min;

(3) Inoculation and observation:

A) The Vero cells were plated in a 24-well plate with $1\times10^5$ cells/well. The growth medium (MEM medium, containing 10% fetal bovine serum, as well as glutamine, penicillin and streptomycin) was aspirated, and 1 mL of maintenance medium (MEM medium, containing 2% fetal calf serum, as well as glutamine, penicillin and streptomycin) was added in each well. Then except the negative control wells, each well was inoculated with 50 μL of the sample supernatant, and cultured in an incubator at 37° C., 5% $CO_2$.

B) The cells were observed under a microscope every day for one week, and the occurrence of specific cytopathic effect (CPE) in the inoculated wells was recorded.

C) If the enterovirus-specific cytopathic effect appeared in the cells in the inoculated wells within 7 days, the cells and supernatant were collected and frozen at −80° C.; if no CPE appeared after 7 days, the cells were subjected to blind passage.

D) If CPE appeared within 6 blind passages, the cells and supernatant were collected and frozen at −80° C.; If CPE did not appear after 6 blind passages, the cells were determined as negative.

(4) Isolation and cloning of viruses:

RT-PCR (Piralla et al., J Clin Microbiol 2015, 53 (5): 1725-1726) and enzyme-linked immunospot method based on specific antibody (Yang et al., Clin Vaccine Immunol 2014, 21 (3): 312-320; Hou et al., J Virol Methods 2015, 215-216: 56-60) were used to identify the viruses isolated from the clinical sample, and EV-D68 positive cultures were selected and subjected to at least 3 cloning experiments. The virus clones obtained by the limiting dilution method in each experiment were also identified by RT-PCR and ELISPOT, and the EV-D68 positive clones were selected for the next round of cloning. A single EV-D68 strain with strong growth viability was selected as a candidate oncolytic virus strain.

1.2 Rescued Strain of Enterovirus EV-D68 and its Modified Form Obtained by Infectious Cloning and Reverse Genetics Technology This example used wild-type EV-D68 (SEQ ID NO: 1) as an example to show how to obtain EV-D68 and its modified form for the present invention through reverse genetics technology. The specific method was as follows.

(1) Construction of viral infectious clone: the cDNA sequence of wild-type enterovirus EV-D68 (named EV-D68-WT) was shown in SEQ ID NO: 1, and its genomic RNA sequence was SEQ ID NO: 12; or gene insertion or replacement based on the cDNA (SEQ ID NO: 1) of enterovirus EV-D68 was performed, comprising:

Modified form 1: the internal ribosome entry site sequence of wild-type EV-D68 was replaced with the internal ribosome entry site sequence of human rhinovirus 2 (which has a DNA sequence shown in SEQ ID NO: 20) to obtain the cDNA (SEQ ID NO: 8) of the recombinant virus (named as EV-D68-HRV2), which has a genomic RNA sequence shown as SEQ ID NO: 13;

Modified form 2: the tandem sequence (which has a DNA sequence shown in SEQ ID NO: 19) of miR-133 target sequence (which has a DNA sequence shown in SEQ ID NO: 17) and miR-206 target sequence (which has a DNA sequence shown in SEQ ID NO: 18) was inserted between 7293-7294 bp of the 3' untranslated region of the cDNA (SEQ ID NO: 1) of the wild-type EV-D68, to obtain the cDNA (SEQ ID NO: 9) of the recombinant virus (named EV-D68-miR133&206T), which has a genomic RNA sequence shown as SEQ ID NO: 14;

Modified form 3: the human granulocyte-macrophage colony-stimulating factor (GM-CSF) gene (SEQ ID NO: 6) was inserted between the VP1 gene and 2A gene of the cDNA (SEQ ID NO: 1) of wild-type EV-D68 to obtain the cDNA (SEQ ID NO: 10) of the recombinant virus (named EV-D68-GM-CSF), which has a genomic RNA sequence shown as SEQ ID NO: 15;

Modified form 4: the sequence (SEQ ID NO: 7) encoding the single chain antibody against human programmed death receptor 1 (Anti-PD-1 scFv) was inserted between the VP1 gene and 2A gene of the cDNA (SEQ ID NO: 1) of wild-type EV-D68 to obtain the cDNA (SEQ ID NO: 11) of the recombinant virus (named EV-D68-Anti-PD-1), which has a genomic RNA sequence shown as SEQ ID NO: 16.

Then, the cDNA sequences (SEQ ID NO: 1, 8-11) of the above five oncolytic viruses were sent to the gene synthesis company (Shanghai Biotech Engineering Co., Ltd.) for full gene synthesis, and ligated into the pSVA plasmid (Hou et al. Virus Res 2015, 205: 41-44; Yang et al., Virus Res 2015, 210: 165-168) to obtain the infectious cloning plasmids of enterovirus EV-D68 or modified forms thereof (i.e., EV-D68-WT, EV-D68-HRV2, EV-D68-miR133&206T, EV-D68-GM-CSF and EV-D68-Anti-PD-1).

(2) Plasmid mini-kit and *E. coli*. DH5α competent cells were purchased from Beijing Tiangen Biochemical Technology Co., Ltd.; Hela cells (ATCC® Number: CCL-2™) and human rhabdomyosarcoma cells (RD cells; ATCC® Number: CCL-136™) were kept by National Institute of Diagnostics and Vaccine Development in Infectious Diseases, Xiamen University, China, and were cultured with DMEM and MEM media respectively, in which 10% fetal bovine serum as well as glutamine, penicillin and streptomycin were added; transfection reagents Lipofactamine2000 and Opti-MEM were purchased from Thermo Fisher Scientific Company.

(3) The infectious cloning plasmids containing the cDNA sequences of the above five oncolytic viruses were transformed into *E. coli* DH5α competent cells, the monoclonal strains were picked out and shaken after the outgrowth of clones, and the plasmids were extracted using the plasmid mini-kit, and then sent to the company (Shanghai Biotech Engineering Co., Ltd.) for sequencing analysis.

(4) The infectious cloning plasmids with correct sequence and the helper plasmid pAR3126 were co-transfected into the cells to rescue virus (Hou et al. Virus Res 2015, 205: 41-44; Yang et al. Virus Res 2015, 210: 165-168). Hela cells were first transfected according to the instructions of the transfection reagent; then observed under a microscope. When CPE appeared in Hela cells, the cells and culture supernatant were harvested, and inoculated with RD cells followed by passaging and culturing, thereby obtaining the candidate strain of oncolytic virus.

Example 2: In Vitro Antitumor Experiment of EV-D68 and Modified Form Thereof 2.1 Viruses and Cell Lines as Used (1) Viruses: this example used EV-D68-WT (SEQ ID NO: 12), EV-D68-HRV2 (SEQ ID NO: 13), EV-D68-miR133&206T (SEQ ID NO: 14), EV-D68-GM-CSF (SEQ ID NO: 15) and EV-D68-Anti-PD-1 (SEQ ID NO: 16) as provided in Example 1.

(2) Cell lines: human rhabdomyosarcoma cell RD (ATCC® Number: CCL-136™); human cervical cancer cell lines Hela (ATCC® Number: CCL-2™), SiHa (ATCC® Number: HTB-35™), Caski (ATCC® Number: CRL-1550™) and C-33A (ATCC® Number: HTB-31™); human ovarian cancer cell lines SKOV-3/TR (drug-resistant strain of SKOV-3), SKOV-3 (ATCC® Number: HTB-77™) and Caov3 (ATCC® Number: HTB-75™); human endometrial cancer cell lines Hec-1-A (ATCC® Number: HTB-112™), Hec-1-B (ATCC® Number: HTB-113™) and Ishikawa (ECACC No. 99040201); human lung cancer cell lines SPC-A-1 (CCTCC Deposit Number: GDC050), NCI-H1299 (ATCC® Number: CRL-5803™) NCI-H1417 (ATCC® Number: CRL-5869™), NCI-H1703 (ATCC® Number: CRL-5889™), NCI-H1975 (ATCC® Number: CRL-5908™), A549 (ATCC® Number: CCL-185™), NCI-H661 (ATCC® Number: HTB-183™), EBC-1 (Thermo Fisher Scientific, Catalog #: 11875101), and DMS114 (ATCC® Number: CRL-2066™); human liver cancer cell lines MHCC97H (purchased from the Institute of Liver Cancer, Fudan University), C3A (ATCC® Number: CRL-10741™), Hep3B (ATCC® Number: HB-8064™), HepG2 (ATCC® Number: HB-8065™), SMMC7721 (purchased from the Basic Medical Cell Center of the Institute of Basic Medical Sciences, Chinese Academy of Medical Sciences, number: 3111C0001CCC000087), BEL7402 (CCTCC Deposit Number: GDC035), BEL7404 (purchased from the Cell Resource Center, Shanghai Institutes of Biological Sciences, Chinese Academy of Sciences, number: 3131C0001000700064), Huh7 (CCTCC Deposit Number: GDC134), PLC/PRF/5 (ATCC® Number: CRL8024™) and SK-Hep-1 (ATCC® Number: HTB-52™); human kidney cancer cell lines A-498 (ATCC® Number: HTB-44™), 786-0 (ATCC® Number: CRL-1932™) and Caki-1 (ATCC® Number: HTB-46™); human neuroblastoma cell lines SH-SYSY (ATCC® Number: CRL-2266™) and SK-N-BE (2) (ATCC® Number: CRL-2271™); human glioma cell lines U87-MG (ATCC® Number: HTB-14™) and U118-MG (ATCC® Number: HTB-15™); human breast cancer cell lines MCF-7 (ATCC® Number: HTB-22™), BcaP37 (CCTCC Deposit Number: GDC206), BT-474 (ATCC® Number: HTB-20™), MDA-MB-231 (ATCC® Number: CRM-HTB-26™) and MDA-MB-453 (ATCC® Number: HTB-131™); human melanoma cell lines A-375 (ATCC® Number: CRL-1619™), SK-MEL-1 (ATCC® Number: HTB-67™) and MeWo (ATCC® Number: HTB-65™); human prostate cancer cell lines PC-3 (ATCC® Number: CRL-1435™), LNCap (ATCC® Number: CRL1740™) and DU145 (ATCC® Number: HTB-81™); human bladder cancer cell lines J82 (ATCC® Number: HTB-1™) and 5637 (ATCC® Number: HTB-9™); human pancreatic cancer cell lines Capan-2 (ATCC® Number: HTB-80™), HPAF-2 (ATCC® Number: CRL-1997™), and PANC-1 (ATCC® Number: CRL-1469™); human gastric cancer cell lines AGS (ATCC® Number: CRL-1739™), SGC7901 (CCTCC Deposit Number: GDC150), BGC823 (CCTCC Deposit Number: GDC151), and NCI-N87 (ATCC® Number: CRL-5822™); human colorectal cancer cell lines DLD-1 (ATCC® Number: CCL-221™), SW1116 (ATCC® Number: CCL-233™), SW480 (ATCC® Number: CCL-228™), HCT-116 (ATCC® Number: CCL247™) and HT-29 (ATCC® Number: HTB-38™); human esophageal cancer cell line TE-1 (purchased from the Cell Resource Center, Shanghai Institutes of Biological Sciences, Chinese Academy of Sciences, No. 3131C0001000700089); human thyroid cancer SW-579 (ATCC® Number: HTB-107™) and TT (ATCC® Number: CRL-1803™); human laryngeal cancer Hep-2 (ATCC® Number: CCL-23™); osteosarcoma 143B (ATCC® Number: CRL-8303™) and U2OS (ATCC® Number: HTB-96™); human lymphoma and leukemia cell lines K562 (ATCC® Number: CCL-243™), U937 (ATCC® Number: CRL-1593.2™), THP-1 (ATCC® Number: TIB-202™), Raji (ATCC® Number: CCL-86™), Daudi (ATCC® Number: CCL-213™), Jurkat (ATCC® Number: TIB-152™) and MT-4 (obtained from the National Institutes of Health, USA); human normal cell lines include: human embryo lung fibroblast cell line MRC-5 (ATCC® Number: CCL-171™), human embryonic kidney cell line HEK-293 (ATCC® Number: CRL-1573™) human foreskin fibroblast cell line FIFF-1 (ATCC® Number: SCRC-1041™), human skin keratinocyte cell line HaCat (CCTCC Deposit Number: GDC106), human prostate stromal cell line WPMY-1 (ATCC® Number: CRL-2854™), human umbilical vein endothelial cell line HUVEC (Thermo Fisher Scientific, Catalog #: C01510C), and differentiated human liver progenitor cell line HepaRG (with characteristics of primary hepatocytes; Thermo Fisher Scientific, Catalog #: HPRGC10). The above cells were kept by National Institute of Diagnostics and Vaccine Development in Infectious Diseases, Xiamen University, China. HepaRG cells were cultured in WME medium (added with 1.5% DMSO), AGS and TT were cultured with F-12K medium, SW-579 was cultured with L-15 medium, SH-SY5Y and SK-N-BE (2) were cultured with DMEM:F12 (1:1) medium, RD, C-33A, EBC-1, J82, SK-Hep-1, SK-MEL-1 and DU145 were cultured with MEM medium, K562, U937, THP-1, Raji, Daudi, Jurkat, MT-4, 5637, 786-O, TE-1, Caski, NCI-H1417, NCI-H1703, NCI-H1975, NCI-H661, SGC7901, BGC823, DLD-1, SW1116, Hep-2, and LNCap were cultured with RPMI-1640 medium, other cells were cultured with DMEM medium. All the mediums mentioned above were supplemented with 10% fetal bovine serum, glutamine and penicillin-streptomycin. All the above cells were cultured under the standard conditions of 37° C. and 5% $CO_2$.

2.2 Virus Culture

RD cells were evenly plated on 10 cm cell culture plates, and the culture conditions included MEM medium containing 10% fetal bovine serum and glutamine, penicillin and streptomycin, 37° C., 5% $CO_2$, and saturated humidity. When the cell confluence reached 90% or more, the cell culture medium was replaced with serum-free MEM medium, and each plate was inoculated with $10^7$ TCID50 of EV-D68-WT, EV-D68-HRV2, EV-D68-miR133&206T, EV-D68-GM-CSF or EV-D68-Anti-PD-1, the culture environment was changed to 33° C., 5% $CO_2$, saturated humidity. After 24 hours, the EV-D68 or its modified form proliferated in RD cells and caused CPE in cells. When more than 90% of the cells turned contracted and rounded, showed increased graininess, and became detached and lysed, the cells and culture supernatants thereof were harvested. After freeze-thawing for three cycles, the culture supernatant was collected and centrifuged to remove cell debris, wherein the centrifuge conditions were 4000 rpm, 10 min, 4° C. Finally, the supernatant was filtered with a 0.22 μm disposable filter (Millipore Company) to remove impurities such as cell debris.

2.3 Determination of Virus Titer

The RD cells were plated in a 96-well plate with a cell density of $10^4$ cells/well. After the cells adhered, the virus solution obtained in Example 2.2 was diluted 10-fold with serum-free MEM medium from the first 10-fold dilution. 50 μl of the dilution of virus was added to the wells with cells. After 7 days, the wells where CPE appeared were monitored and recorded, followed by calculation using Karber method, in which the calculation formula was $lg^{TCID50}$=L−D (S−0.5), L: logarithm of the highest dilution, D: difference between the logarithms of dilutions, S: sum of proportions of positive wells. The unit of TCID50 thus calculated was TCID50/50 μl, which should be converted to TCID50/ml.

2.4 In Vitro Antitumor Experiment of Viruses

Human tumor cells and normal cells were inoculated into 96-well plates at $10^4$ cells/well. After the cells adhered, the medium in each well was replaced with the corresponding cell culture medium without serum, and viruses were inoculated at an MOI of 0.1, 1, 10 or 100. Subsequently, CPE of the cells were monitored daily by a microscope.

Figure 1:
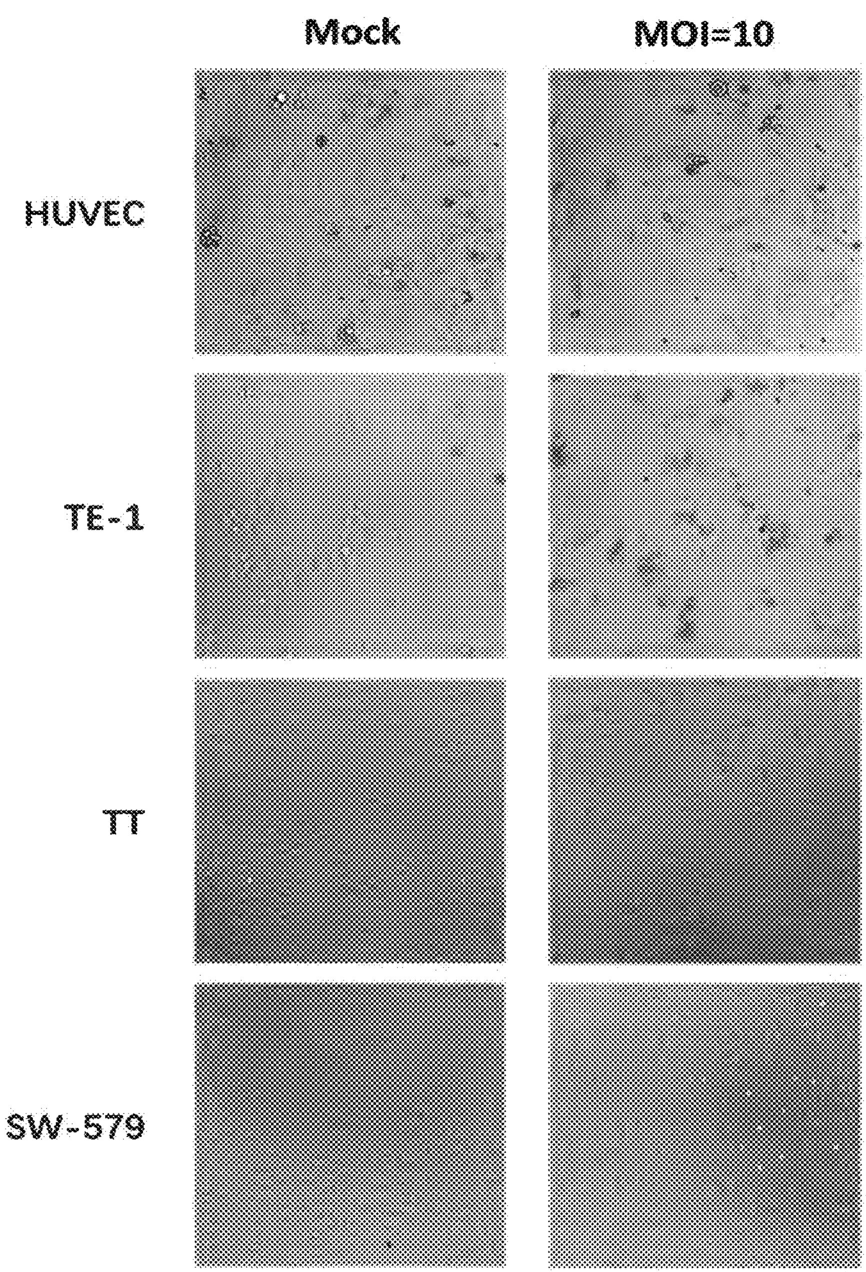
FIG. 1 shows photomicrographs of the in vitro killing tests of the wild-type EV-D68 on human umbilical vein endothelial cell line HUVEC, human esophageal cancer cell line TE-1, human thyroid cancer cell lines SW-579 and TT in Example 2, wherein MOCK represents cells that are not infected with the virus. The results showed that the EV-D68 had a significant oncolytic effect on human tumor cell lines TE-1, SW-579, and TT after 72 hours of infection at a multiplicity of infection (MOI) of 10, but had no effect on HUVEC of human normal cells.

FIG. 1 shows micrographs of the human umbilical vein endothelial cell line HUVEC, the human esophageal cancer cell line TE-1, and the human thyroid cancer cell line SW-579 and TT, which were not infected with viruses (negative control group, Mock) or which were treated with EV-D68-WT at MOI=10 for 72 hours. The results showed that after 72 hours of infection at a multiplicity of infection (MOT) of 10, a significant reduction in the number of the tumor cells, marked shrinking and lysis and the like, were detected in the virus-infected groups; while as compared to the non-tumor cells in the Mock group, the non-tumor cells infected with the viruses showed almost no change in cell morphology. The above results demonstrated that EV-D68 had significant oncolytic effects on human tumor cell lines TE-1, SW-579 and TT, but did not have any effect on non-tumor cells HUVEC.

After 72 hours of virus infection and culture, the cell survival rate was detected using Cell Counting Kit-8 (CCK-8 kit; Shanghai Biyuntian Biotechnology Co., Ltd.) and crystal violet staining method (only for adherent cells), and the specific method was as follows:

(1) Cell survival rate detected by CCK8 method

For adherent cells, the original medium in a 96-well cell culture plate was directly discarded; for suspension cells, the original medium in a 96-well cell culture plate was carefully discarded after centrifugation; and then 100 μl of fresh serum-free medium was added per well. 10 μl of CCK-8 solution was added to each of the wells inoculated with cells, and an equal amount of CCK-8 solution was also added to the blank culture medium as a negative control, followed by incubation at 37° C. in a cell culture incubator for 0.5-3 hours. The absorbance was detected at 450 nm using a microplate reader at 0.5, 1, 2, 3 hours, respectively, and the time point where the absorbance was within a suitable range was selected as a reference for cell survival rate. The CCK-8 test results of EV-D68-WT for each kind of cells were shown in Table 2, where "−" indicated that the cell survival rate after virus treatment was not significantly different from that of the MOCK group; "+" indicated that after virus treatment, the cell number was reduced, the survival rate was still greater than 50% but was significantly different from that of the MOCK group; "++" indicated that the cell survival rate after virus treatment was less than 50%, and was significantly different from that of the MOCK group.

The calculation of cell survival rate was:

$$\text{Cell\_survival\_rate}(\%) = \frac{(\text{reading\_of\_test\_group} - \text{reading\_of\_negative\_group})}{(\text{reading\_of\_positive\_group} - \text{reading\_of\_negaive\_group})} \times 100\%.$$

(2) Cell survival rate detected by crystal violet staining method (only for adherent cells)

Figure 2:
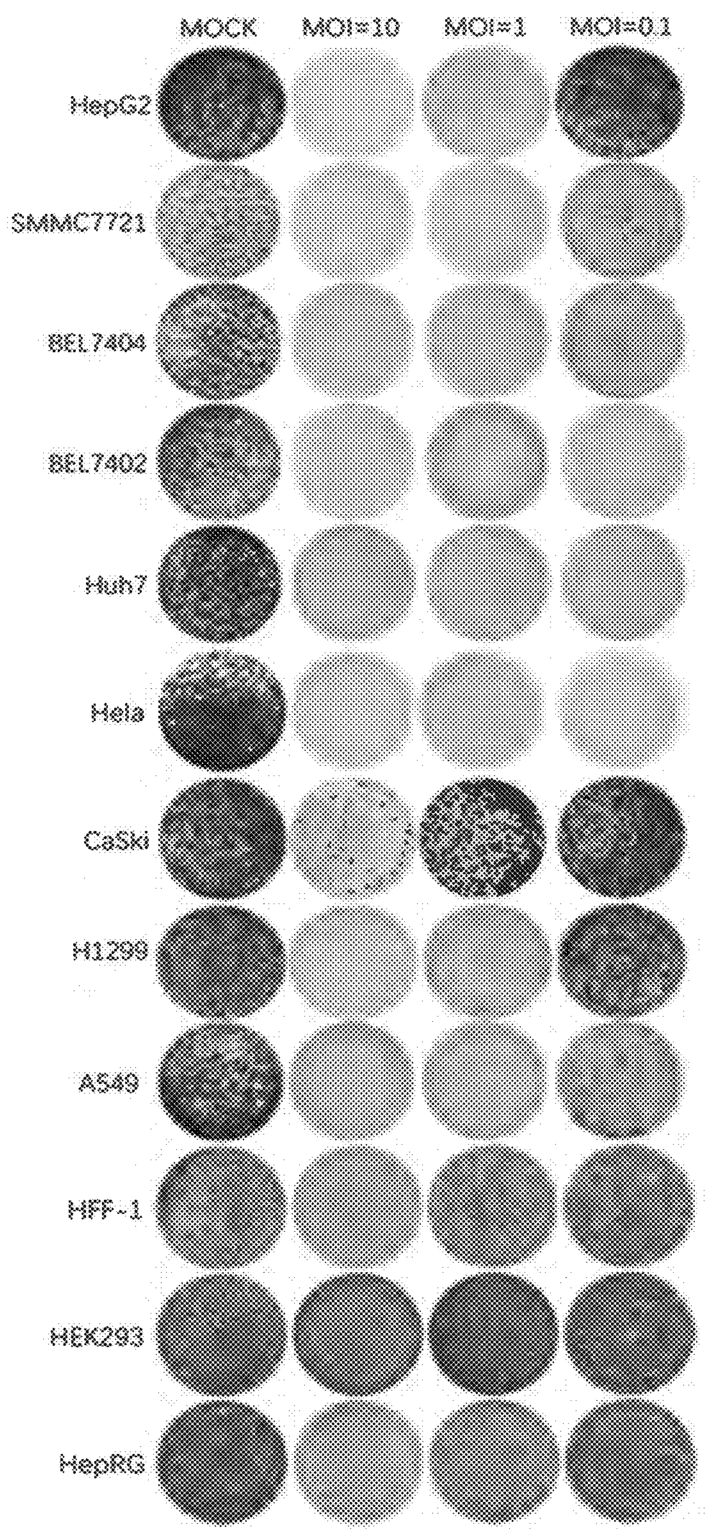
FIG. 2 shows the photos of crystal violet staining of the in vitro killing tests of the wild-type EV-D68 on human liver cancer cell lines HepG2, SMMC7721, BEL7404, BEL7402, and Huh7, human cervical cancer cell lines Hela and Caski, human lung cancer cell lines NCI-H1299 and A549, human foreskin fibroblast cell line human embryonic kidney cell line HEK-293, and differentiated human liver progenitor cell line HepaRG in Example 2, wherein MOCK represents cells that are not infected with the virus. The results showed that the EV-D68 had significant oncolytic effects on human tumor cell lines HepG2, SMMC7721, BEL7404, BEL7402, Huh7, Hela, Caski, NCI-H1299 and A549 after 72 hours of infection at MOIs of 10, 1, and 0.1, but had limited effect on HFF-1, HEK-293 and differentiated HepaRG of human normal cells.

After the cells were infected with viruses for 3 days, the culture supernatant in the 96-well cell culture plate was discarded, 100 μl of methanol was added to each well, followed by fixation in the dark for 15 min. Crystal violet powder (Shanghai Biotech Biotechnology Co., Ltd.) was weighed, and formulated as 2% (w/v) crystal violet methanol solution, which was stored at 4° C. An appropriate amount of 2% crystal violet methanol solution was taken and formulated with PBS solution to prepare 0.2% crystal violet working solution. After fixation for 15 minutes, the methanol fixation solution in the 96-well cell culture plate was discarded, and 100 μl of the crystal violet working solution was added to the plate and staining was performed for 30 min. After the crystal violet staining solution was discarded, PBS solution was used for washing for 3 to 5 times, until the excess staining solution was washed off, and air-drying was performed. ImmunSpot @S5 UV Analyzer (Cellular Technology Limited, USA) was used for photographing. FIG. 2 showed the crystal violet staining results of the human liver cancer cell lines HepG2, SMMC7721, BEL7404, BEL7402 and Huh7, the human cervical cancer cell lines Hela and Caski, the human lung cancer cell lines NCI-H1299 and A549, the human foreskin fibroblast cell line HFF-1, the human embryonic kidney cell line HEK-293, and the differentiated human hepatic progenitor cell line HepaRG in the control group (MOCK) and in the experimental groups (infected for 72 hours with EV-D68-WT at MOIs of 0.1, 1, and 10, respectively). As shown in the results, after 72 hours of infection at MOIs of 10, 1, and 0.1, the tumor cells in the experimental groups were significantly reduced as compared to the control group (MOCK) without addition of virus; while the number of non-tumor cells showed no significant change. The above results indicated that the EV-D68-WT had significant oncolytic effects on human tumor cell lines HepG2, SMMC7721, BEL7404, BEL7402, Huh7, Hela, Caski, NCI-H1299 and A549, but had no significant effect on non-tumor cell lines HFF-1, HEK-293 and the differentiated HepaRG.

TABLE 2

Results of in vitro antitumor experiment of wild-type enterovirus EV-D68

| Cell Line | Multiplicity of infection MOI | | | |
|---|---|---|---|---|
| | 0.1 | 1 | 10 | 100 |
| RD | ++ | ++ | ++ | ++ |
| Hela | ++ | ++ | ++ | ++ |
| SiHa | − | − | ++ | ++ |
| Caski | − | + | ++ | ++ |
| C-33A | − | ++ | ++ | ++ |
| SKOV-3/TR | − | − | − | + |
| SKOV-3 | − | − | ++ | ++ |
| Caov3 | + | ++ | ++ | ++ |
| Hec-1-A | − | − | − | ++ |
| Hec-1-B | − | + | ++ | ++ |
| Ishikawa | − | − | ++ | ++ |
| SPC-A-1 | − | + | ++ | ++ |
| NCI-H1299 | − | ++ | ++ | ++ |
| NCI-H1417 | − | − | − | + |
| NCI-H1703 | − | − | − | + |
| NCI-H1975 | − | ++ | ++ | ++ |
| A549 | + | ++ | ++ | ++ |
| NCI-H661 | − | − | + | ++ |
| EBC-1 | − | − | + | ++ |
| DMS114 | ++ | ++ | ++ | ++ |
| MHCC97H | + | ++ | ++ | ++ |
| C3A | ++ | ++ | ++ | ++ |
| Hep3B | − | + | + | ++ |
| HepG2 | − | ++ | ++ | ++ |
| SMMC7721 | + | ++ | ++ | ++ |
| BEL7402 | ++ | ++ | ++ | ++ |
| BEL7404 | + | ++ | ++ | ++ |
| Huh7 | ++ | ++ | ++ | ++ |
| PLC/PRF/5 | − | + | ++ | ++ |
| SK-Hep-1 | − | − | + | ++ |
| A-498 | + | ++ | ++ | ++ |
| 786-O | − | − | + | ++ |
| Caki-1 | ++ | ++ | ++ | ++ |
| SH-SY5Y | − | + | ++ | ++ |
| SK-N-BE(2) | − | − | − | + |
| U87-MG | + | ++ | ++ | ++ |
| U118-MG | ++ | ++ | ++ | ++ |
| MCF-7 | − | − | − | + |
| BcaP37 | − | ++ | ++ | ++ |
| BT-474 | − | − | − | + |
| MDA-MB-231 | ++ | ++ | ++ | ++ |
| MDA-MB-453 | − | − | + | ++ |
| A-375 | − | + | ++ | ++ |
| SK-MEL-1 | + | ++ | ++ | ++ |
| MeWo | − | + | ++ | ++ |
| PC-3 | ++ | ++ | ++ | ++ |
| LNCap | − | + | ++ | ++ |
| DU145 | ++ | ++ | ++ | ++ |
| J82 | − | + | ++ | ++ |
| 5637 | − | − | − | + |
| Capan-2 | − | − | + | ++ |
| HPAF-2 | − | + | + | ++ |
| PANC-1 | − | ++ | ++ | ++ |
| AGS | − | − | + | ++ |
| SGC7901 | − | − | − | + |
| BGC823 | − | + | + | ++ |
| NCI-N87 | − | + | ++ | ++ |
| DLD-1 | − | − | − | + |
| SW1116 | + | + | ++ | ++ |
| SW480 | − | + | ++ | ++ |
| HCT-116 | − | − | + | ++ |
| HT-29 | + | ++ | ++ | ++ |
| TE-1 | − | + | ++ | ++ |
| SW-579 | − | − | ++ | ++ |
| TT | − | − | ++ | ++ |
| Hep-2 | − | + | ++ | ++ |
| 143B | − | − | − | + |
| U2OS | + | + | ++ | ++ |
| K562 | − | + | + | ++ |

TABLE 2-continued

Results of in vitro antitumor experiment of wild-type enterovirus EV-D68

| Cell Line | Multiplicity of infection MOI | | | |
|---|---|---|---|---|
| | 0.1 | 1 | 10 | 100 |
| U937 | − | − | + | ++ |
| THP-1 | + | ++ | ++ | ++ |
| Raji | ++ | ++ | ++ | ++ |
| Daudi | ++ | ++ | ++ | ++ |
| Jurkat | ++ | ++ | ++ | ++ |
| MT-4 | ++ | ++ | ++ | ++ |
| MRC-5 | − | − | + | ++ |
| HEK-293 | − | − | − | − |
| HFF-1 | − | − | + | + |
| HaCat | − | − | − | − |
| WPMY-1 | − | − | − | − |
| HUVEC | − | − | − | − |
| HepaRG | − | − | − | + |

Note:
"−" indicated that there was no significant difference in cell survival rate between virus treatment group and MOCK group;
"+" indicated that after virus treatment, the number of cells was reduced, the survival rate was greater than 50% but was significantly different from that of MOCK group;
"++" indicated that the cell survival rate after virus treatment was less than 50%, and was significantly different from that of the MOCK group.

It could be known from Table 2 that the wild-type enterovirus EV-D68 had a killing effect on the tested tumor cells, and therefore had a broad-spectrum anti-tumor activity. In particular, the virus had significant killing effects on liver cancer cell lines, glioma cell lines, prostate cancer cell lines, leukemia and lymphoma cell lines. On the other hand, the virus had little or no toxicity to the non-tumor cell lines tested, except that it was significantly toxic to human embryonic lung fibroblast MRC-5 at higher MOIs.

In addition, in vitro antitumor experiments of EV-D68-HRV2, EV-D68-miR133&206T, EV-D68-GM-CSF and EV-D68-Anti-PD-1 showed that the four modified EV-D68s retained the broad-spectrum killing effect of the wild-type enterovirus EV-D68 on the tested tumor cells, and substantially retained the significant killing effect on the tested tumor cells of human hepatocellular carcinoma cell line, prostate cancer cell line, leukemia and lymphoma cell lines, wherein the CCK-8 test results of oncolytic effect of the four modified EV-D68s on cervical cancer cell line Hela, glioma cell line U118-MG, liver cancer cell line Huh7, prostate cancer cell line PC-3, and lymphoma cell line Raji were shown in Table 3.

TABLE 3

Results of in vitro antitumor experiment of EV-D68-HRV2, EV-D68-miR133&206T, EV-D68-GM-CSF and EV-D68-Anti-PD-1

| Cell Lines | | Multiplicity of infection MOI | | | |
|---|---|---|---|---|---|
| | | 0.1 | 1 | 10 | 100 |
| EV-D68-HRV2 | Hela | + | + | ++ | ++ |
| | U118-MG | + | ++ | ++ | ++ |
| | Huh7 | ++ | ++ | ++ | ++ |
| | PC-3 | ++ | ++ | ++ | ++ |
| | Raji | − | + | + | ++ |
| EV-D68-miR133&206T | Hela | ++ | ++ | ++ | ++ |
| | U118-MG | ++ | ++ | ++ | ++ |
| | Huh7 | ++ | ++ | ++ | ++ |
| | PC-3 | ++ | ++ | ++ | ++ |
| | Raji | ++ | ++ | ++ | ++ |

TABLE 3-continued

Results of in vitro antitumor experiment of EV-D68-HRV2, EV-D68-miR133&206T, EV-D68-GM-CSF and EV-D68-Anti-PD-1

| Cell Lines | | Multiplicity of infection MOI | | | |
|---|---|---|---|---|---|
| | | 0.1 | 1 | 10 | 100 |
| EV-D68-GM-CSF | Hela | ++ | ++ | ++ | ++ |
| | U118-MG | ++ | ++ | ++ | ++ |
| | Huh7 | ++ | ++ | ++ | ++ |
| | PC-3 | ++ | ++ | ++ | ++ |
| | Raji | ++ | ++ | ++ | ++ |
| EV-D68-Anti-PD-1 | Hela | ++ | ++ | ++ | ++ |
| | U118-MG | ++ | ++ | ++ | ++ |
| | Huh7 | ++ | ++ | ++ | ++ |
| | PC-3 | ++ | ++ | ++ | ++ |
| | Raji | ++ | ++ | ++ | ++ |

Note:
"–" indicated that there was no significant difference in cell survival rate between virus treatment group and MOCK group;
"+" indicated that after virus treatment, the number of cells was reduced, the survival rate was greater than 50% but was significantly different from that of MOCK group;
"++" indicated that the cell survival rate after virus treatment was less than 50%, and was significantly different from that of the MOCK group.

In addition, the inventors unexpectedly found that EV-D68-HRV2 exhibited significantly improved killing activity on some tumors compared to EV-D68-WT, wherein the CCK-8 test results of the oncolytic activity of the human gastric cancer cell line AGS, the human endometrial cancer cell lines HEC-1-A and Ishikawa, the human cervical cancer cell line C-33A, and the human thyroid cancer cell line SW579 were shown in Table 4.

TABLE 4

Comparison of the results of in vitro oncolytic experiment of EV-D68-WT and EV-D68-HRV2 on some tumor cells

| Cell Line | | MOI | | | |
|---|---|---|---|---|---|
| | | 0.01 | 0.1 | 1 | 10 |
| EV-D68-WT | AGS | – | – | – | + |
| | HEC-1-A | – | – | – | – |
| | Ishikawa | – | – | – | ++ |
| | C-33A | – | – | ++ | ++ |
| | SW579 | – | – | – | ++ |
| EV-D68-HRV2 | AGS | ++ | ++ | ++ | ++ |
| | HEC-1-A | – | + | ++ | ++ |
| | Ishikawa | ++ | ++ | ++ | ++ |
| | C-33A | ++ | ++ | ++ | ++ |
| | SW579 | ++ | ++ | ++ | ++ |

Note:
"–" indicated that there was no significant difference in cell survival rate between virus treatment group and MOCK group;
"+" indicated that after virus treatment, the number of cells was reduced, the survival rate was greater than 50% but was significantly different from that of MOCK group;
"++" indicated that the cell survival rate after virus treatment was less than 50%, and was significantly different from that of the MOCK group.

2.5 Serial Passaging of EV-D68 for Adaptation

In this example, EV-D68 was serially passaged for adaptation in a certain type of tumor cell to obtain a virus strain with enhanced killing activity to the tumor cell.

The wild-type enterovirus EV-D68 was serially passaged for adaptation in the human cervical cancer cell line SiHa, human ovarian cancer cell line SKOV-3, human liver cancer cell line SK-hep-1, human pancreatic cancer cell line Capan-2, human gastric cancer cell line AGS or human colorectal cancer cell line HCT-116 on which the oncolytic effect of EV-D68 was not very significant, and the specific method was as follows:

One kind of the above tumor cells was evenly plated on a 10 cm cell culture plate, and the culture conditions included a corresponding cell culture media containing 10% fetal bovine serum and glutamine, penicillin and streptomycin, 37° C., 5% $CO_2$, and saturated humidity. When the cell confluence reached 90% or more, the cell culture medium was replaced with serum-free cell culture medium, each plate was inoculated with $10^7$ TCID50 of EV-D68, the culture environment was changed to 33° C., 5% $CO_2$, saturated humidity. When EV-D68 proliferated in tumor cells and caused CPE in the cells (after infection for up to 3 days), the cells and their culture supernatant were harvested. After freeze-thawing for three cycles, centrifugation was performed at 4° C., 4000 rpm for 10 min. The centrifugation supernatant was taken and added onto new tumor cells with a cell confluence of more than 90% to complete one round of virus passage. The passage was repeated for more than 10 times, and a part of the virus solution was taken for virus titer detection in RD cells in each round of passage, and the specific method referred to Example 2.3. Generally, the virus replication ability would increase with the generation, and when a relatively high infectious titer was reached and the virus replication was stable in the tumor cell, the adapted strain of EV-D68 for the tumor cell was obtained.

Subsequently, by the in vitro antitumor experimental method described in Example 2.4, the human tumor cell SiHa, SKOV-3, SK-hep-1, Capan-2, AGS, or HCT-116 was inoculated to a 96-well plate at $10^4$ cells/well. After the cells adhered, the medium in each well was replaced with the corresponding culture medium free of serum, followed by incubation at 37° C. for 30 min, and then the serially passaged EV-D68 virus strains (viral titers of which were detected on RD cells) adapted for each of the above kinds of cells at MOIs of 0.1, 1, 10, and 100 were inoculated. Subsequently, CPE of the cells were monitored daily by a microscope, and the cell survival rate was detected using CCK-8 method 72 hours after the infection and culture of viruses.

The results were shown in Table 5, in which after serial passaging of the wild-type enterovirus EV-D68 in a certain kind of tumor cells on which EV-D68 had poor oncolytic effect, the killing activity thereof on the tumor cells was significantly enhanced, indicating that the serial passaging method could be used to obtain an EV-D68 adapted strain with enhanced oncolytic effect on the tumor cells.

TABLE 5

Results of in vitro killing experiment of EV-D68 on a tumor cell after serial passaging for adaptation in the tumor cell

| Cell Line | 0.1 | 1 | 10 | 100 |
|---|---|---|---|---|
| SiHa | + | ++ | ++ | ++ |
| SKOV-3 | – | ++ | ++ | ++ |
| SK-hep-1 | – | ++ | ++ | ++ |
| Capan-2 | – | + | ++ | ++ |
| AGS | + | + | ++ | ++ |
| HCT-116 | – | + | ++ | ++ |

Note:
"–" indicated that there was no significant difference in cell survival rate between virus treatment group and MOCK group;
"+" indicated that after virus treatment, the number of cells was reduced, the survival rate was greater than 50% but was significantly different from that of MOCK group;
"++" indicated that the cell survival rate after virus treatment was less than 50%, and was significantly different from that of the MOCK group.

2.6 Evaluation of Oncolytic Effect of Genomic RNA of EV-D68

In this example, a large amount of infectious live viruses of EV-D68 could be produced by transfecting the purified genomic RNA of EV-D68 into a certain kind of tumor cells, and thus kill the tumor cells.

Figure 3:
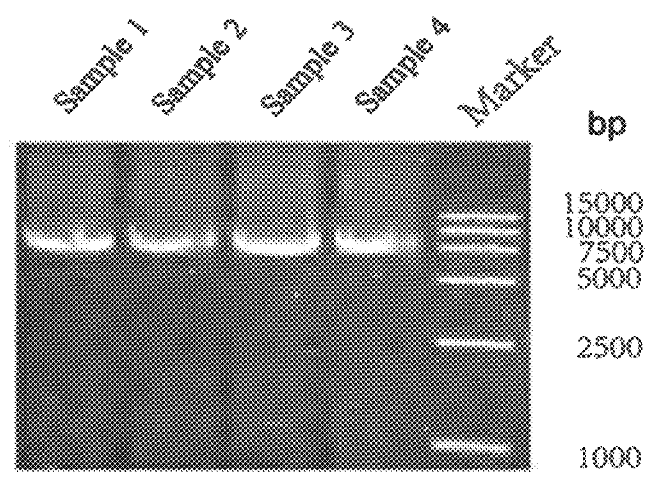
FIG. 3 shows an electrophoresis image of four samples of wild-type EV-D68 virus genomic RNA of the same batch obtained by the in vitro transcription method in Example 2.

The viral genomic RNA was first obtained by in vitro transcription, and this method could be found in, for example, Hadac E M, Kelly E J and Russell S J. Mol Ther, 2011, 19(6): 1041-1047. Specifically, the infectious cloning plasmid of wild-type EV-D68 obtained in Example 1 was linearized, and the linearized plasmid was used as a template for in vitro transcription using MEGAscript™ T7 Transcription Kit (Thermo Fisher Scientific, AM1333) so as to produce a large amount of viral RNA. And the obtained viral RNA was purified using MEGAclear™ Transcription Clean-Up Kit (Thermo Fisher Scientific, AM1908) for next use. The RNA electropherograms of 4 parallel samples were shown in FIG. 3.

Subsequently, according to the method of the in vitro antitumor experiment described in Example 2.4, the human cervical cancer tumor cell line Hela was inoculated to a 24-well plate at $10^5$ cells/well. After the cells adhered, the medium in each well was replaced with a corresponding cell culture medium free of serum, followed by incubation at 37° C. for 30 min. Then Hela cells were transfected with purified virus RNA at 1 μg per well using transfection reagent Lipofectamine® 2000 (Thermo Fisher Scientific, 11668019), and the negative control group was transfected with irrelevant RNA nucleic acid molecules. Subsequently, CPE of the cells were monitored daily by a microscope.

The results showed that CPE began to appear in the Hela cells transfected with genomic RNA of EV-D68 about 8 hours after transfection, and then the cytopathy gradually increased. After 48 hours, the survival rate was measured using the CCK8 method, the Hela cells had almost all died and lysed. And the micrographs of Hela cells at 0, 24 and 48 hours after infection were shown in FIG. 4. The culture supernatant was inoculated into new Hela cells and CPE was quickly produced. The results indicated that the direct administration with the nucleic acid of EV-D68 also had good killing activity and could be used to treat tumors.

Example 3: In Vivo Antitumor Experiments of Enterovirus EV-D68 and its Modified Forms 3.1 Viruses, Cell Lines and Experimental Animals (1) Viruses: the EV-D68-WT (SEQ ID NO: 12), EV-D68-HRV2 (SEQ ID NO: 13), EV-D68-miR133&206T (SEQ ID NO: 14), EV-D68-GM-CSF (SEQ ID NO: 15) and EV-D68-Anti-PD-1 (SEQ ID NO: 16) provided in Example 1 were used in this example. The methods of virus culture and virus titer measurement could be seen in Examples 2.2 and 2.3, respectively.

(2) Cell lines: human cervical cancer cell line Hela (ATCC® Number: CCL-2™), glioma cell line U118-MG (ATCC® Number: HTB-15™), and lymphoma cell line Raji (ATCC® Number: CCL-86™). Except that Raji was cultured with RPMI-1640 medium, the other Hela and U118-MG were all cultured with DMEM medium. These mediums were all supplemented with 10% fetal bovine serum, glutamine and penicillin-streptomycin. All the above cells were cultured under the standard conditions of 37° C. and 5% $CO_2$.

(3) Experimental animals: female C.B17 SCID mice aged 6-8 weeks were from Shanghai Slark Experimental Animal Co., Ltd.; the mice were raised under SPF conditions, according to the protocol approved by the Experimental Animal Center and Ethics Committee of Xiamen University.

3.2 In Vivo Antitumor Experiments of the Virus

The tumor cells used for subcutaneous tumor formation in SCID mice were digested with 0.01% trypsin, and then resuspended into a single-cell suspension using a cell culture medium containing 10% fetal bovine serum. The cell density of the suspension was counted. The cells were precipitated by centrifugation under 1000 g for 3 min, and then the cells were resuspended with an appropriate volume of PBS to reach a concentration of about $10^6$-$10^7$ cells/100 μl PBS. The tumor cells were subcutaneously inoculated in the back of SCID mice at $10^6$-$10^7$ cells/100 μl PBS/site with a syringe. When the tumor cells grew into a tumor mass of about 100 $mm^3$ under the skin of SCID mice after about 14-21 days, the tumor-bearing SCID mice were randomly divided into experimental groups (administrated with EV-D68-WT, EV-D68-HRV2, EV-D68-miR133&206T, EV-D68-GM-CSF or EV-D68-Anti-PD-1) and negative control group, with 4 mice (n=4) in each group. Oncolytic virus (EV-D68-WT, EV-D68-HRV2, EV-D68-miR133&2061, EV-D68-GM-CSF or EV-D68-Anti-PD-1) at $10^6$ TCID50/100 μl serum-free medium/tumor mass or equivalent amount of serum-free medium were intratumorally injected every two days, for a total of 5 treatments. The tumor size was measured with a vernier caliper and recorded every two days, and the method for calculating the tumor size was:

$$\text{Tumor size (mm}^3\text{)} = \text{tumor length value} \times (\text{tumor width value})^2/2.$$

The treatment results of EV-D68-WT for the above three tumors were shown in FIGS. 5A-5C. The results showed that after the challenge of EV-D68-WT, the growth of the three tested tumors of Hela (A), U118-MG (B) and Raji (C) gradually slowed down and arrested, and the tumors were even lysed and disappeared; by contrast, the tumors of the negative group (CTRL) maintained the normal growth, and their tumor sizes were significantly larger than those of the experimental groups.

Table 6 showed the results obtained after a treatment of the Raji tumor model with EV-D68-WT, EV-D68-HRV2, EV-D68-miR133&206T, EV-D68-GM-CSF or EV-D68-Anti-PD-1 for 10 days. The results showed that the tumor volumes were significantly reduced after treatment with EV-D68-WT, EV-D68-HRV2, EV-D68-miR133&206T, EV-D68-GM-CSF, and EV-D68-Anti-PD as compared with the negative control group that was not treated with oncolytic virus, wherein similar reductions in tumor volume were detected after treatment with 4 oncolytic viruses EV-D68-WT, EV-D68-miR133&206T, EV-D68-GM-CSF and EV-D68-Anti-PD-1. The above results indicated that all of EV-D68-WT, EV-D68-HRV2, EV-D68-miR133&206T, EV-D68-GM-CSF and EV-D68-Anti-PD-1 showed remarkable and favorable antitumor activity in vivo.

TABLE 6

Results of in vivo anti-tumor experiments of EV-D68-WT, EV-D68-HRV2, EV-D68-miR133&206T, EV-D68-GM-CSF and EV-D68-Anti-PD-1 on human lymphoma cell line Raji

| Oncolytic virus | In vivo oncolytic effect on Raji after 10 days of treatment |
|---|---|
| EV-D68-WT | ++ |
| EV-D68-HRV2 | + |
| EV-D68-miR133&206T | ++ |
| EV-D68-GM-CSF | ++ |
| EV-D68-Anti-PD-1 | ++ |

Note:
"+" indicated that after treatment, the tumor volume reducedand was greater than 50% of the negative control group, but was significantly different from that of the negative control group;
"++" indicated that the tumor volume reduced to less than 50% of the negative control group after treatment, and was significantly different from that of the negative control group.

Example 4: Safety Evaluation of Oncolytic Virus 4.1 Viruses and Laboratory Animals Used (1) Virus: the EV-D68-WT (SEQ ID NO: 12) provided in Example 1 was used in this example. The methods for virus culture and virus titer measurement could refer to Examples 2.2 and 2.3, respectively.

(2) Experimental animals: BALB/c pregnant mice were from Shanghai Slark Experimental Animal Co., Ltd.; according to the protocol approved by the Experimental Animal Center and Ethics Committee of Xiamen University, the mice were raised under clean conditions, and then the 1-day-old, 2-day-old, 3-day-old, 7-day-old and 14-day-old mice produced by the BALB/c pregnant mice were used for in vivo virulence evaluation of EV-D68.

4.2 Evaluation of the Safety of the Virus in Mice (1) BALB/c suckling mice aged 1 day were selected for challenge with EV-D68-WT by intraperitoneal injection, and the titer doses for challenge were $10^3$, $10^4$, $10^5$, $10^6$, or $10^7$ TCID50/mouse. Then the survival rates and health scores for the BALB/c mice challenged with different doses were recorded daily, wherein the evaluation criteria of the health score were: score of 5, represents dying or died; score of 4 represents severe limb paralysis; score of 3 represents weakness or mild deformity of limb; score of 2 represents wasting; score of 1 represents lethargy, piloerection, and trembling; and score of 0 represents healthy.

The results were shown in FIG. 6A. Within 20 days after challenge, all mice in the group with extremely high-dose of $10^7$ TCID50 became ill and died within 1 week; 80% of the mice in the group with high-dose of $10^6$ TCID50 eventually survived and only few mice became ill and died; in addition, no morbidity and death occurred in the mice of the challenge groups with other doses.

(2) The 1-day-old, 2-day-old, 3-day-old, 7-day-old and 14-day-old BALB/c mice were injected with EV-D68-WT at an extremely high dose of $10^7$ TCID50/mouse, and then the survival rates and health scores for the BALB/c with different ages in days were recorded daily, wherein the evaluation criteria of the health score were the same as above.

The results were shown in FIG. 6B. Within 20 days after challenge, the 1-day-old mice all died within 1 week; the 2-day-old mice resisted in a certain extent to EV-D68 toxicity, and eventually had a survival rate of 70%, but with a relatively high incidence of disease and relatively severe symptoms; the 3-day-old mice were already not vulnerable to EV-D68, and eventually had a survival rate of 90%, and with a low incidence of disease and mild symptoms; the 4- or more-day-old mice were fully tolerant to the high doses of EV-D68, and no morbidity and death occurred.

The above results showed that the EV-D68-WT was less toxic to mice, and was only lethal to the 1- to 3-day-old BALB/c mice at an extremely high dose of $10^7$ TCID50/mouse, and had no effect on the 4- or more-day-old mice, thereby indicating good safety in vivo.

Although specific embodiments of the present invention have been described in detail, those skilled in the art will understand that according to all the teachings that have been published, various modifications and changes can be made to the detail, and these changes are all within the protection scope of the present invention. The protection scope of the present invention is given by the appended claims and any equivalents thereof.

What is claimed is:

1. A method of treating a lymphoma, the method comprising administering by intratumoral injection, to a subject in need thereof, an effective amount of a modified EV-D68, an isolated nucleic acid molecule, or a medicament comprising the modified EV-D68, or the isolated nucleic acid molecule, wherein the isolated nucleic acid molecule comprises a sequence selected from the group consisting of:

(1) a genomic sequence or cDNA sequence of the modified EV-D68; and (2) a complementary sequence of the genomic sequence or cDNA sequence;

wherein, as compared to a genome of the wild-type EV-D68, a genome of the modified EV-D68 has a substitution of the internal ribosome entry site (IRES) sequence in a 5' untranslated region (5'UTR) with an exogenous IRES sequence from human rhinovirus 2 (HRV2); and the modified EV-D68 has the genomic sequence as set forth in SEQ ID NO: 13 or has the cDNA sequence as set forth in SEQ ID NO: 8;

and wherein the subject is a human.

2. The method of claim 1, wherein:

(1) the isolated nucleic acid molecule consists of the genomic sequence of the the modified EV-D68; or (2) the isolated nucleic acid molecule is a vector comprising the cDNA sequence of the modified EV-D68, or the complementary sequence of the cDNA sequence.

3. The method of claim 1, wherein the modified EV-D68, or the isolated nucleic acid molecule is administered in combination with an additional pharmaceutically active agent having antitumor activity.

4. A modified EV-D68, a genome of which has a substitution of the internal ribosome entry site (IRES) sequence in a 5' untranslated region (5'UTR) with an exogenous IRES sequence from human rhinovirus 2 (HRV2) as compared to a genome of a wild-type EV-D68; and the modified EV-D68 has the genomic sequence as set forth in SEQ ID NO: 13 or has the cDNA sequence as set forth in SEQ ID NO: 8.

5. An isolated nucleic acid molecule, comprising a sequence selected from the group consisting of:

(1) the genomic sequence or cDNA sequence of the modified EV-D68 of claim 4; and (2) the complementary sequence of the genomic sequence or cDNA sequence.

6. The isolated nucleic acid molecule of claim 5, wherein:

(1) the isolated nucleic acid molecule consists of the genomic sequence of the EV-D68 or the modified EV-D68; or (2) the isolated nucleic acid molecule is a vector comprising the cDNA sequence of the EV-D68 or the modified EV-D68, or the complementary sequence of the cDNA sequence.

* * * * *